(12) United States Patent
Diev et al.

(10) Patent No.: US 11,683,979 B2
(45) Date of Patent: Jun. 20, 2023

(54) ELECTROACTIVE MATERIALS

(71) Applicant: LG Chem Ltd., Seoul (KR)

(72) Inventors: Viacheslav V. Diev, Wilmington, DE (US); John David Allen, New Castle, DE (US); Kerwin D. Dobbs, Wilmington, DE (US); Weiying Gao, Landenberg, PA (US); Michael Henry Howard, Jr., Montchain, DE (US); Michael R. Moseley, New Castle, DE (US); Weishi Wu, Landenberg, PA (US)

(73) Assignee: LG Chem, Ltd.

( * ) Notice: Subject to any disclaimer, the term of this patent is extended or adjusted under 35 U.S.C. 154(b) by 33 days.

(21) Appl. No.: 15/543,306

(22) PCT Filed: Jan. 20, 2016

(86) PCT No.: PCT/US2016/014086
§ 371 (c)(1),
(2) Date: Jul. 13, 2017

(87) PCT Pub. No.: WO2016/126423
PCT Pub. Date: Aug. 11, 2016

(65) Prior Publication Data
US 2018/0062082 A1 Mar. 1, 2018

Related U.S. Application Data

(60) Provisional application No. 62/111,139, filed on Feb. 3, 2015, provisional application No. 62/111,137, filed on Feb. 3, 2015, provisional application No. 62/111,135, filed on Feb. 3, 2015.

(51) Int. Cl.
| | | |
|---|---|---|
| *H01L 51/00* | (2006.01) |
| *C07D 311/78* | (2006.01) |
| *C09K 11/06* | (2006.01) |
| *C09B 57/00* | (2006.01) |
| *C07C 13/66* | (2006.01) |
| *C07C 211/61* | (2006.01) |
| *C07D 307/77* | (2006.01) |
| *C07D 209/80* | (2006.01) |
| *C07D 221/18* | (2006.01) |
| *C07F 7/08* | (2006.01) |
| *C07D 471/06* | (2006.01) |
| *C07D 345/00* | (2006.01) |
| *C07D 335/04* | (2006.01) |
| *C07D 307/78* | (2006.01) |
| *C07D 471/04* | (2006.01) |
| *H01L 51/50* | (2006.01) |
| *H01L 51/52* | (2006.01) |

(52) U.S. Cl.
CPC .......... *H01L 51/0054* (2013.01); *C07C 13/66* (2013.01); *C07C 211/61* (2013.01);
(Continued)

(58) Field of Classification Search
CPC ............... C09K 11/06; C09K 11/1025; C09K 2211/1025; H01L 51/0043; H01L 51/0032;
(Continued)

(56) References Cited

U.S. PATENT DOCUMENTS

| | | | |
|---|---|---|---|
| 4,216,101 A | * | 8/1980 | Davis ...................... C08K 5/23 252/581 |
| 6,670,645 B2 | | 12/2003 | Grushin et al. |
| 7,351,358 B2 | | 4/2008 | Hsu et al. |
| 8,465,848 B2 | | 6/2013 | Smith |

(Continued)

FOREIGN PATENT DOCUMENTS

| | | |
|---|---|---|
| CN | 103589420 A | 2/2014 |
| CN | 103589421 A | 2/2014 |

(Continued)

OTHER PUBLICATIONS

Lee et al., Machine Translation of KR 2014-0096002 A, (2014), pp. 1-54. (Year: 2014).*

(Continued)

*Primary Examiner* — Dylan C Kershner
(74) *Attorney, Agent, or Firm* — Lerner David LLP

(57) ABSTRACT

There is disclosed a compound Formula I

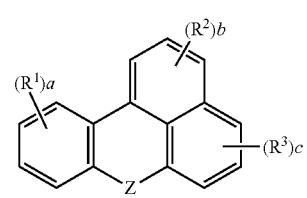

(I)

In Formula I:
Z is $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, or $TeO_2$;
$R^1$-$R^3$ are the same or different at each occurrence and are D, aryl, heteroaryl, alkyl, amino, silyl, germyl, deuterated aryl, deuterated heteroaryl, deuterated alkyl, deuterated amino, deuterated silyl, or deuterated germyl, where two groups selected from $R^1$, $R^2$, and $R^3$ can be joined together to form a fused ring;
$R^4$-$R^5$ are the same or different at each occurrence and are H, D, aryl, heteroaryl, alkyl, amino, silyl, germyl, deuterated aryl, deuterated heteroaryl, deuterated alkyl, deuterated amino, deuterated silyl, or deuterated germyl;
$R^{4a}$ is alkyl, silyl, germyl, aryl, or a deuterated analog thereof;
a is an integer from 0-4;
b and c are the same or different and are an integer from 0-3.

6 Claims, 2 Drawing Sheets

(52) U.S. Cl.
CPC ......... *C07D 209/80* (2013.01); *C07D 221/18* (2013.01); *C07D 307/77* (2013.01); *C07D 307/78* (2013.01); *C07D 311/78* (2013.01); *C07D 335/04* (2013.01); *C07D 345/00* (2013.01); *C07D 471/04* (2013.01); *C07D 471/06* (2013.01); *C07F 7/081* (2013.01); *C07F 7/0816* (2013.01); *C09B 57/00* (2013.01); *C09B 57/001* (2013.01); *C09B 57/008* (2013.01); *C09K 11/06* (2013.01); *H01L 51/0032* (2013.01); *H01L 51/0034* (2013.01); *H01L 51/0035* (2013.01); *H01L 51/0043* (2013.01); *H01L 51/0059* (2013.01); *H01L 51/0061* (2013.01); *H01L 51/0071* (2013.01); *H01L 51/0072* (2013.01); *H01L 51/0073* (2013.01); *H01L 51/0074* (2013.01); *H01L 51/0085* (2013.01); *H01L 51/0094* (2013.01); *H01L 51/5048* (2013.01); *H01L 51/5068* (2013.01); *H01L 51/5221* (2013.01); *C07C 2603/54* (2017.05); *C09K 2211/1011* (2013.01); *C09K 2211/1025* (2013.01); *H01L 51/5012* (2013.01)

(58) Field of Classification Search
CPC . H01L 51/0034; H01L 1/0054; H01L 1/0032; H01L 1/0034; H01L 1/0043; H01L 1/0085; H01L 1/5048; H01L 1/5068; H01L 1/5221; C07D 307/78; C07D 311/78; C07D 471/04; C09B 57/008
See application file for complete search history.

(56) References Cited

U.S. PATENT DOCUMENTS

| | | | | |
|---|---|---|---|---|
| 2003/0011306 | A1* | 1/2003 | Bechtel | H01L 27/32 313/509 |
| 2004/0076853 | A1* | 4/2004 | Jarikov | C09K 11/06 428/690 |
| 2004/0102577 | A1 | 5/2004 | Hsu et al. | |
| 2004/0127637 | A1 | 7/2004 | Hsu et al. | |
| 2005/0184287 | A1 | 8/2005 | Herron et al. | |
| 2005/0205860 | A1 | 9/2005 | Hsu et al. | |
| 2006/0235060 | A1* | 10/2006 | Yoshida | C07D 263/60 514/366 |
| 2008/0100208 | A1* | 5/2008 | Shin | C07C 13/62 313/504 |
| 2009/0303418 | A1* | 12/2009 | Yang | G02B 5/201 349/69 |
| 2010/0176382 | A1* | 7/2010 | Park | H01L 51/5271 257/40 |
| 2010/0252817 | A1* | 10/2010 | Kim | C07C 15/20 257/40 |
| 2011/0024780 | A1* | 2/2011 | Park | H01L 51/5237 257/98 |
| 2012/0021143 | A1* | 1/2012 | Hiratsuka | C09K 19/60 428/1.31 |
| 2013/0082251 | A1 | 4/2013 | Park et al. | |
| 2013/0299809 | A1* | 11/2013 | Wang | H01L 51/5206 257/40 |
| 2013/0299811 | A1* | 11/2013 | Seki | H01L 51/0054 257/40 |
| 2014/0361266 | A1* | 12/2014 | Jung | H01L 51/0061 257/40 |
| 2015/0048321 | A1* | 2/2015 | Kim | H01L 51/0052 257/40 |
| 2015/0048323 | A1* | 2/2015 | Kim | H01L 51/0061 257/40 |
| 2015/0194609 | A1* | 7/2015 | Nishide | C07D 405/14 257/40 |
| 2015/0357586 | A1* | 12/2015 | Horiuchi | C09K 11/06 257/40 |
| 2015/0372244 | A1* | 12/2015 | Abe | H01L 51/0058 257/40 |
| 2016/0087216 | A1* | 3/2016 | Kim | H01L 51/0055 257/40 |
| 2016/0118593 | A1* | 4/2016 | Kim | C07D 409/12 548/440 |
| 2016/0133857 | A1* | 5/2016 | Kim | H01L 51/0073 257/40 |
| 2016/0172594 | A1* | 6/2016 | Kim | H01L 51/008 257/40 |
| 2016/0190448 | A1* | 6/2016 | Kim | H01L 51/008 257/40 |
| 2016/0190449 | A1* | 6/2016 | Jun | H01L 51/008 257/40 |
| 2016/0190481 | A1* | 6/2016 | Han | C07F 7/0816 257/40 |
| 2017/0012205 | A1* | 1/2017 | Jung | C07F 7/081 |
| 2017/0092701 | A1* | 3/2017 | Uchida | H01L 27/3211 |
| 2017/0125688 | A1* | 5/2017 | Kim | H01L 51/0061 |
| 2017/0229654 | A1* | 8/2017 | Gao | H01L 51/0035 |
| 2017/0338423 | A9* | 11/2017 | Meng | C07D 495/04 |

FOREIGN PATENT DOCUMENTS

| | | | |
|---|---|---|---|
| CN | 103804408 A | | 5/2014 |
| CN | 103805166 A | | 5/2014 |
| CN | 103805169 A | | 5/2014 |
| JP | 2009-152383 | * | 7/2009 |
| JP | 2010034458 A | * | 2/2010 |
| JP | 2010087410 A | * | 4/2010 |
| JP | 2010135405 A | * | 6/2010 |
| KR | 10-2011-0104765 A | | 9/2011 |
| KR | 10-2011-0112098 A | | 10/2011 |
| KR | 20120081539 A | * | 7/2012 |
| KR | 20140096002 A | * | 8/2014 |
| WO | 2003/008424 A1 | | 1/2003 |
| WO | 2003/040257 A1 | | 5/2003 |
| WO | 2003/063555 A1 | | 7/2003 |
| WO | 2003/091688 A2 | | 11/2003 |
| WO | 2004/016710 A1 | | 2/2004 |
| WO | 2005/052027 A1 | | 6/2005 |
| WO | 2007/145979 A3 | | 4/2008 |
| WO | WO-2010104047 A1 * | 9/2010 | ............... C07F 5/00 |
| WO | 2011/115378 A1 | | 9/2011 |
| WO | 2011/126224 A1 | | 10/2011 |

OTHER PUBLICATIONS

Nakamura et al., Machine Translation of WO 2010/104047 A1, (2010), pp. 1-19. (Year: 2010).*

Orchin et al., "Aromatic Cyclodehydrogenation. X. Studies on Ring Oxygen Compounds. Dinaphtho[1,2,1',2']-furan," Journal of the American Chemical Society, 1951, vol. 73, pp. 1877-1878. (Year: 1951).*

Han et al., Machine translation of KR 2012/0081539 A (2012) pp. 1-81. (Year: 2012).*

Vyskocil, "2,8'-Disubstituted-1,1'-Binaphthyls: A New Pattern in Chiral Ligands," Chemistry a European Journal (2002), vol. 8 No. 20 , pp. 4633-4648. (Year: 2002).*

Han et al., Machine translation of KR-20120081539-A (2012) pp. 1-79. (Year: 2012).*

Clar et al., "3-Benzopicene and naphtho(2': 3'-1 : 2)chrysene," J. Chem. Soc. (1957) pp. 4163-4166. (Year: 1957).*

Nakatsuka, machine translation of JP-2010034458-A (2010) pp. 1-13. (Year: 2010).*

Nakatsuka, machine translation of JP-2010087410-A (2010) pp. 1-14. (Year: 2010).*

Romero-Nieto et al., "Paving the Way to Novel Phosphorus-Based Architectures: A Noncatalyzed Protocol to Access Six-Membered Heterocycles", Angewandte Communications, vol. 54 (2015) pp. 15872-15875. (Year: 2015).*

Panico, "ms-Diphenylanthracenic thio ethers", Ann. chim. (Paris), vol. 10 (1955)—attached CAS record attached relied upon. (Year: 1955).*

(56) References Cited

OTHER PUBLICATIONS

Grisorio, "First disubstituted dibenzothiophene-5,5-dioxide monodispersed molecular materials for efficient blue-electroluminescence", Journal of Materials Chemistry, Dec. 14, 2009, vol. 20, pp. 1012-1018. (Year: 2009).*
Barbarella, "From Easily Oxidized to Easily Reduced Thiophene-Based Materials", 1998, vol. 10, pp. 551-554. (Year: 1998).*
Nakamura et al., machine translation of WO 2010/104407 (2010) pp. 1-19. (Year: 2010).*
Dral et al., "Doped Polycyclic Aromatic Hydrocarbons as Building Blocks for Nanoelectronics: A Theoretical Study", The Journal of Organic Chemistry, vol. 78 (2013) pp. 1894-1902. (Year: 2013).*
Wang et al., "Synthesis of Sulfur-Bridged Polycycles via Pd-Catalyzed Dehydrogenative Cyclization" Organic Letters (2014) vol. 16, pp. 4574-4577. (Year: 2014).*
Nakatsuka, machine translation of JP 2010-135405 (2010) pp. 1-15. (Year: 2010).*
Wang, Y., Kirk-Othmer Encyclopedia of Chemical Technology, Fourth Edition, 1996, vol. 18, pp. 837-860 (Book Not Included).
PCT International Search Report for Application No. PCT/US2016/014086; ISA/KR; dated Oct. 31, 2016.
International Preliminary Report on Patentability, PCT/US2016/014086, Athina Nicktas-Etienne, Authorized Officer, IB, dated Aug. 17, 2017.
Gustafsson, G. et al. "Flexible light-emitting diodes made from soluble conducting polymers" Letters to Nature, vol. 357, Jun. 11, 1992, pp. 477-479.
CRC Handbook of Chemistry and Physics, 81st Edition, 2000-2001 (Book Not Included).
Chinese Search Report for Application No. 201680008101.0 dated Jul. 28, 2021, 2 pages.

\* cited by examiner

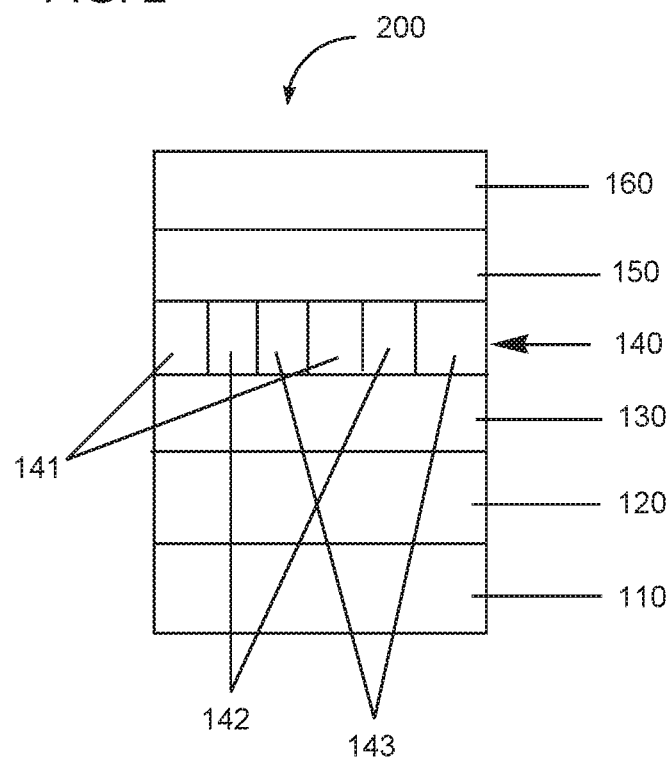

ELECTROACTIVE MATERIALS

BACKGROUND INFORMATION

Field of the Disclosure

The present disclosure relates to novel electroactive compounds. The disclosure further relates to electronic devices having at least one layer comprising such an electroactive compound.

Description of the Related Art

In organic electronic devices, such as organic light emitting diodes ("OLED"), that make up OLED displays, one or more organic electroactive layers are sandwiched between two electrical contact layers. In an OLED at least one organic electroactive layer emits light through the light-transmitting electrical contact layer upon application of a voltage across the electrical contact layers.

It is well known to use organic electroluminescent compounds as the light-emitting component in light-emitting diodes, Simple organic molecules, conjugated polymers, and organometallic complexes have been used.

Devices that use electroluminescent materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode, There is a continuing need for electroactive materials for use in electronic devices.

SUMMARY

There is provided a an electroactive material which is a compound having Formula I

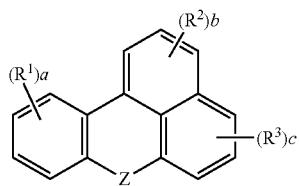

(I)

wherein;
- Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;
- $R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;
- $R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
- $R^{4a}$ is selected from the group consisting of alkyl, silyl, germyl, aryl, and deuterated analogs thereof;
- a is an integer from 0-4; and
- b, and c are the same or different and are an integer from 0-3.

There is also provided an electroactive material which is a compound having Formula II-a, Formula II-b, or Formula II-c

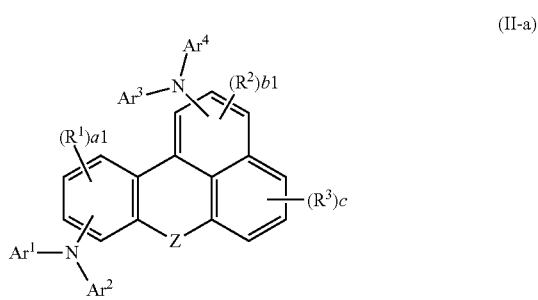

(II-a)

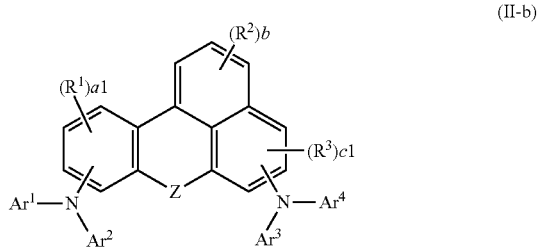

(II-b)

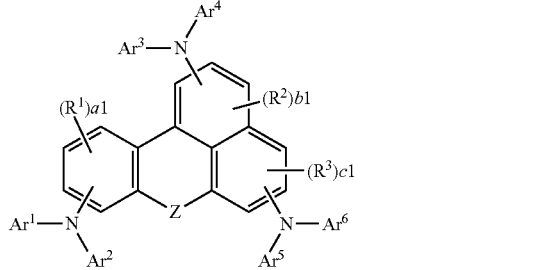

(II-c)

wherein:
- Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;
- $Ar^1$-$Ar^6$ are the same or different and are selected from the group consisting of aryl groups, heteroaryl groups, and deuterated analogs thereof;
- $R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;
- $R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
- $R^{4a}$ is selected from the group consisting of alkyl, silyl, germyl, aryl, and deuterated analogs thereof;
- a1, b, and c are the same or different and are an integer from 0-3; and b1 and c1 are the same or different and are an integer from 0-2.

There is also provided an electroactive material which is a compound having Formula III-a, Formula III-b, or Formula III-c

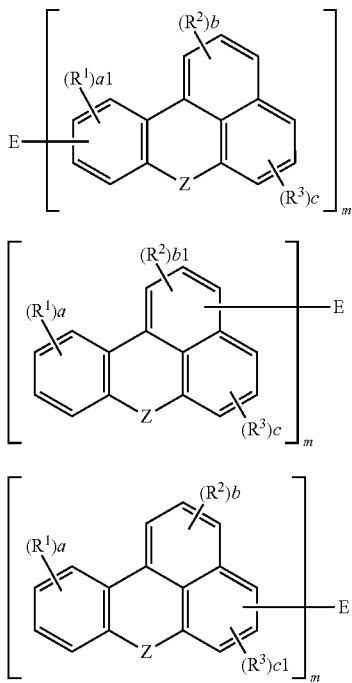

wherein:
- E is selected from the group consisting of aryl, heteroaryl, and deuterated analogs thereof;
- Z is selected from the group consisting of CR$^4$R$^5$, C=CR$^4$R$^5$, SiR$^4$R$^5$, GeR$^4$R$^5$, NR$^{4a}$, PR$^{4a}$, P(O)R$^{4a}$, O, S, SO, SO$_2$, Se; SeO, SeO$_2$, Te, TeO, and TeO$_2$;
- R$^1$-R$^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from R$^1$, R$^2$, and R$^3$ can be joined together to form a fused ring;
- R$^4$-R$^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
- R$^{4a}$ is selected from the group consisting of alkyl, silyl, germyl, aryl, and deuterated analogs thereof;
- a is an integer from 0-4;
- a1, b, and c are the same or different and are an integer from 0-3;
- b1 and c1 are the same or different and are an integer from 0-2; and
- m is 2 or 3.

There is also provided an electroactive material which is a compound having Formula IV-a, Formula IV-b, or Formula IV-c

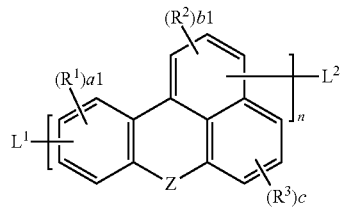

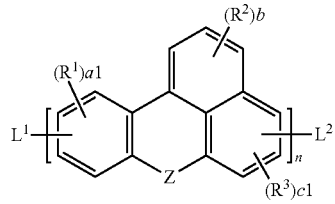

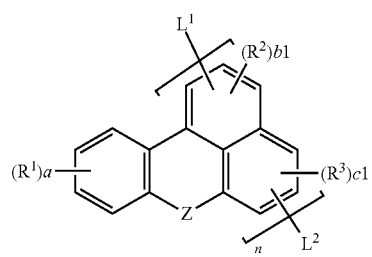

wherein:
- Z is selected from the group consisting of CR$^4$R$^5$, C=CR$^4$R$^5$, SiR$^4$R$^5$, GeR$^4$R$^5$, NR$^{4a}$, PR$^{4a}$, P(O)R$^{4a}$, O, S, SO, SO$_2$, Se; SeO, SeO$_2$, Te, TeO, and TeO$_2$;
- L$^1$ and L$^2$ are the same or different and are selected from the group consisting of H, D, halogen, aryl, arylamino, crosslinkable groups, deuterated aryl, deuterated arylamino, and deuterated crosslinkable groups;
- R$^1$-R$^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from R$^1$, R$^2$, and R$^3$ can be joined together to form a fused ring;
- R$^4$-R$^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
- R$^{4a}$ is selected from the group consisting of alkyl, silyl, germyl, aryl, and deuterated analogs thereof;
- a is an integer from 0-4;
- a1, b, and c are the same or different and are an integer from 0-3;
- b1 and c1 are the same or different and are an integer from 0-2; and
- n is an integer greater than 0.

The is also provided an electroactive material which is a copolymer having at least one monomeric unit having Formula V-a, Formula V-b, or Formula V-c

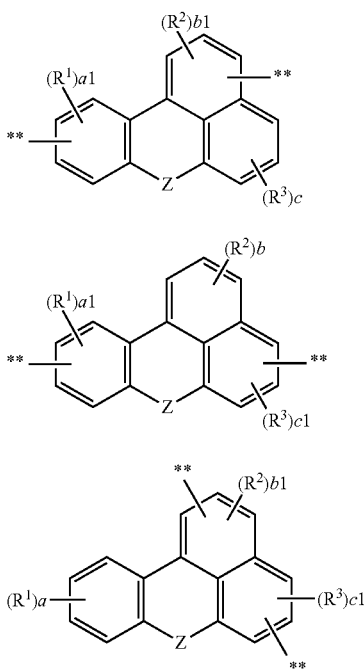

wherein:
- Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;
- $R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;
- $R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
- $R^{4a}$ is selected from the group consisting of alkyl, silyl, germyl, aryl, and deuterated analogs thereof;
- a is an integer from 0-4;
- a1, b, and c are the same or different and are an integer from 0-3;
- b1 and c1 are the same or different and are an integer from 0-2; and
- ** indicates the point of attachment in the copolymer.

There is also provided an electronic device having at least one layer comprising a compound having any of the above formulae, The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

FIG. 2 includes an illustration of another example of an organic electronic device.

Figure 1:
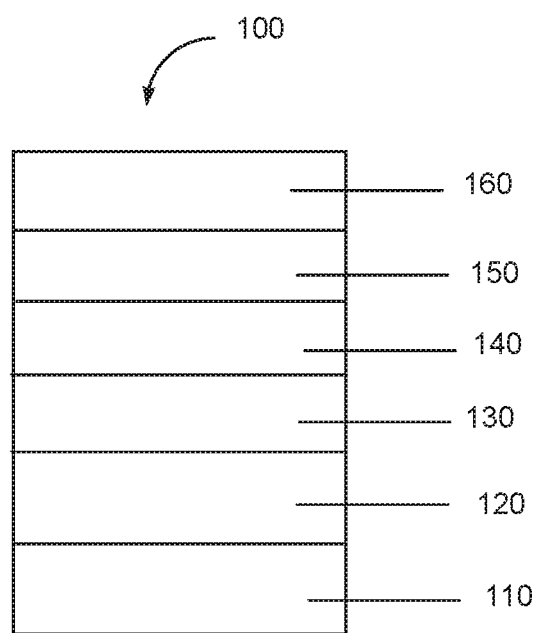
FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

There is provided a compound having Formula I, as described in detail below.

There is further provided a compound having Formula II-a, as described in detail below.

There is further provided a compound having Formula II-b, as described in detail below.

There is further provided a compound having Formula II-c, as described in detail below.

There is further provided a compound having Formula III-a, as described in detail below.

There is further provided a compound having Formula III-b, as described in detail below.

There is further provided a compound having Formula III-c, as described in detail below.

There is further provided a compound having Formula IV-a, as described in detail below.

There is further provided a compound having Formula IV-b, as described in detail below, There is further provided a compound having Formula IV-c, as described in detail below.

There is further provided a copolymer having at least one monomeric unit having Formula V-a, as described in detail below.

There is further provided a copolymer having at least one monomeric unit having Formula V-b, as described in detail below.

There is further provided a copolymer having at least one monomeric unit having Formula V-c, as described in detail below.

There is further provided an electronic device having at least one layer comprising a compound or copolymer having any of the above formulae.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Compound of Formula I, the Compound of Formula II-a, Formula II-v, or Formula II-c, the Compound of Formula III-a, Formula III-b, or Formula the Compound of Formula IV-a, Formula IV-b or Formula IV-c, the Copolymer Having at Least One Monomeric Unit Having Formula V-a, Formula V-b, or Formula V-c, the Electronic Device, and finally Examples.

1. Definitions and Clarification of Terms

Before addressing details of embodiments described below, some terms are defined or clarified.

As used herein, the term "alkyl" includes branched and straight-chain saturated aliphatic hydrocarbon groups. Unless otherwise indicated, the term is also intended to include cyclic groups. Examples of alkyl groups include methyl, ethyl, propyl, isopropyl, isobutyl, secbutyl, tert-butyl, pentyl, isopentyl, neopentyl, cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms. The term is intended to include heteroalkyl groups. Heteroalkyl groups may have from 1-20 carbon atoms.

The term "aromatic compound" is intended to mean an organic compound comprising at least one unsaturated cyclic group having 4n+2 delocalized pi electrons. The term is intended to encompass both aromatic compounds having only carbon and hydrogen atoms in the cyclic group ("hydrocarbon aromatics"), and heteroaromatic compounds wherein one or more of the carbon atoms within the cyclic group has been replaced by another atom, such as nitrogen, oxygen, sulfur, or the like.

The term "aryl" or "aryl group" means a moiety derived from an aromatic compound. A group "derived from" a compound, indicates the radical formed by removal of one or more H or D. The aryl group may be a single ring (monocyclic) or multiple rings (bicyclic, or more) fused together or linked covalently. Examples of aryl moieties include, but are not limited to, phenyl, 1-naphthyl, 2-naphthyl, dihydronaphthyl, tetrahydronaphthyl, biphenyl. anthryl, phenanthryl, fluorenyl, indanyl, biphenylenyl, acenaphthenyl, acenaphthylenyl, and the like. In some embodiments, aryl groups have 6 to 60 ring carbon atoms; in some embodiments, 6 to 30 ring carbon atoms. The term is intended to include heteroaryl groups. Heteroaryl groups may have from 4-50 ring carbon atoms; in some embodiments, 4-30 ring carbon atoms.

The term "alkoxy" is intended to mean the group —OR, where R is alkyl.

The term "aryloxy" is intended to mean the group —OR, where R is aryl.

Unless otherwise indicated, all groups can be substituted or unsubstituted. An optionally substituted group, such as, but not limited to, alkyl or aryl, may be substituted with one or more substituents which may be the same or different. Suitable substituents include D, alkyl, aryl, nitro, cyano, —N(R')(R'), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, silyl, siloxy, siloxane, thioalkoxy, —S(O)$_2$—, —C(=O)—N(R')(R"), (R')(R")N-alkyl, (R')(R")N-alkoxyalkyl, (R')(R") N-alkylaryloxyalkyl, —S(O)$_s$-aryl (where s=0-2) or —S(O)$_s$-heteroaryl (where s=0-2). Each R' and R" is independently an optionally substituted alkyl, cycloalkyl, or aryl group, R' and R", together with the nitrogen atom to which they are bound, can form a ring system in certain embodiments. Substituents may also be crosslinking groups. Any of the preceding groups with available hydrogens, may also be deuterated.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The term "crosslinkable group" or "crosslinking group" is intended to mean a group on a compound or polymer chain than can link to another compound or polymer chain via thermal treatment, use of an initiator, or exposure to radiation, where the link is a covalent bond. In some embodiments, the radiation is UV or visible. Examples of crosslinkable groups include, but are not limited to vinyl, acrylate, perfluorovinylether, 1-benzo-3,4-cyclobutane, o-quinodimethane groups, siloxane, cyanate groups, cyclic ethers (epoxides), cycloalkenes, and acetylenic groups.

The term "deuterated" is intended to mean that at least one hydrogen ("H") has been replaced by deuterium ("D"). The term "deuterated analog" refers to a structural analog of a compound or group in which one or more available hydrogens have been replaced with deuterium. In a deuterated compound or deuterated analog, the deuterium is present in at least 100 times the natural abundance level.

The term "electroactive" as it refers to a layer or a material, is intended to indicate a layer or material which electronically facilitates the operation of the device. Examples of electroactive materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The term "germyl" refers to the group $R_3Ge$—, where R is the same or different at each occurrence and is H, D, C1-20 alkyl, deuterated alkyl, fluoroalkyl, aryl, or deuterated aryl.

The prefix "fluoro" is intended to indicate that one or more hydrogens in a group has been replaced with fluorine.

The prefix "hetero" indicates that one or more carbon atoms has been replaced with a different atom. In some embodiments, the heteroatom is O, N, S, or combinations thereof.

The term "liquid composition" is intended to mean a liquid medium in which a material is dissolved to form a solution, a liquid medium in which a material is dispersed to form a dispersion, or a liquid medium in which a material is suspended to form a suspension or an emulsion.

The term "photoactive" refers to a material or layer that emits light when activated by an applied voltage (such as in a light emitting diode or chemical cell), that emits light after the absorption of photons (such as in down-converting phosphor devices), or that responds to radiant energy and generates a signal with or without an applied bias voltage (such as in a photodetector or a photovoltaic cell).

The term "siloxane" refers to the group $R_3SiOR_2Si$—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

The term "siloxy" refers to the group R₃SiO—, where R is the same or different at each occurrence and is H, D, C1-20 alkyl, deuterated alkyl, fluoroalkyl, aryl, or deuterated aryl.

The term "silyl" refers to the group R₃Si—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

In this specification, unless explicitly stated otherwise or indicated to the contrary by the context of usage, chemical and structural formulae may be depicted using the line-angle formula convention. In a line-angle formula, bonds are represented by lines, and carbon atoms are assumed to be present wherever two lines meet or a line begins or ends. Nitrogen, oxygen, halogens, and other heteroatoms are shown; but hydrogen atoms are not usually drawn when bonded to carbon. Each sp³ carbon atom is assumed to have enough bonded hydrogen atoms in order to give it a total of four bonds; each sp² carbon, three bonds; each sp carbon, two bonds. Thus, for example, toluene is depicted as

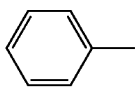

In a structure where a substituent bond passes through one or more rings as shown below,

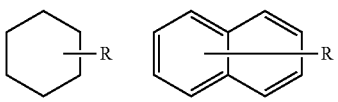

it is meant that the substituent R may be bonded at any available position on the one or more rings.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). Exemplary adjacent R groups are shown below:

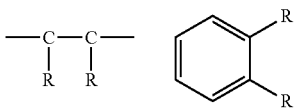

In the compounds described herein, the positions on the fused ring core are numbered as follows:

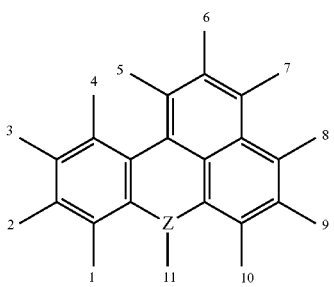

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics,* 81st Edition (2000-2001).

In this specification, unless explicitly stated otherwise or indicated to the contrary by the context of usage, chemical and structural formulae may be depicted using the line-angle formula convention. In a line-angle formula, bonds are represented by lines, and carbon atoms are assumed to be present wherever two lines meet or a line begins or ends. Nitrogen, oxygen, halogens, and other heteroatoms are shown; but hydrogen atoms are not usually drawn when bonded to carbon. Each sp³ atom is assumed to have enough bonded hydrogen atoms in order to give it a total of four bonds; each sp² carbon, three bonds; each sp carbon, two bonds. The depictions of formulae herein are examples of the use of the line-angle formula convention.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Compound of Formula I

In some embodiments, the electroactive compound has Formula I

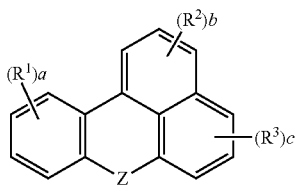

wherein:
Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;

$R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;

$R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;

$R^{4a}$ is selected from the group consisting of alkyl, silyl, germyl, aryl, and deuterated analogs thereof;

a is an integer from 0-4; and b, and c are the same or different and are an integer from 0-3.

In some embodiments, the compound having Formula I is deuterated. In some embodiments, the compound is at least 10% deuterated. By "% deuterated" or "% deuteration" is meant the ratio of deuterons to the sum of protons plus deuterons, expressed as a percentage. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula I, there are no amino groups.

In some embodiments of Formula I, there are at least two amino groups. The amino groups can be attached directly to the core group as $R^1$, $R^2$, or $R^3$, or the amino groups can be substituents on $R^1$, $R^2$, or $R^3$.

In some embodiments of Formula I, Z is selected from the group consisting of $CR^4R^5$, $C=CR^4R^5$, $SiR^4R^5$, $NR^{4a}$, O and S.

In some embodiments of Formula I, Z is selected from the group consisting of $CR^4R^5$, $C=CR^4R^5$, $SiR^4R^5$, and $GeR^4R^5$.

In some embodiments of Formula I, Z is $CR^4R^5$.
In some embodiments of Formula I, Z is $C=CR^4R^5$.
In some embodiments of Formula I, Z is $SiR^4R^5$.
In some embodiments of Formula I, Z is $GeR^4R^5$.
In some embodiments of Formula I, Z is $NR^{4a}$.
In some embodiments of Formula I, Z is selected from the group consisting of $PR^{4a}$ and $P(O)R^{4a}$.
In some embodiments of Formula I, Z is selected from the group consisting of O, S, SO, $SO_2$, Se, and Te,
In some embodiments of Formula I, Z is O.

In some embodiments of Formula I, Z is S.
In some embodiments of Formula I, Z is SO.
In some embodiments of Formula I, Z is $SO_2$.
In some embodiments of Formula I, Z is Se.

In some embodiments of Formula I, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic, In some embodiments of Formula I, at least one $R^2$ is present at position 7, as defined above, and at least one $R^3$ is present at position 8, as defined above.

In some embodiments of Formula I, $R^2$ at position 7 and $R^3$ at position 8 are joined together to form a fused ring group. In some embodiments, the fused ring group comprises a single fused ring. In some embodiments, the fused ring group comprises more than one fused ring.

In some embodiments, the fused ring group is a hydrocarbon aromatic. In some embodiments, the fused ring group is a heteroaromatic. In some embodiments, the fused ring group is non-aromatic.

In some embodiments, the fused ring group has 5-15 ring carbons; in some embodiments, 6-10 ring carbons.

In some embodiments, the fused ring group is unsubstituted.

In some embodiments, the fused ring group is substituted. In some embodiments, the substituents are selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula I, a=0.
In some embodiments of Formula I, a=1.
In some embodiments of Formula I, a=2.
In some embodiments of Formula I, a=3.
In some embodiments of Formula I, a=4.
In some embodiments of Formula I, a>0.
In some embodiments of Formula I, a>0 and at least one $R^1$=D.

In some embodiments of Formula I, a>0 and at least one $R^1$ is an alkyl or deuterated alkyl having 1-20 carbons; in some embodiments, 1-12 carbons; in some embodiments, 3-8 carbons.

In some embodiments of Formula I, a>0 and at least one $R^1$ is a hydrocarbon aryl group having 6-36 ring carbons. The hydrocarbon aryl group can include one or more single ring groups bonded together, one or more fused rings, or combinations thereof.

In some embodiments of Formula I, a>0 and at least one $R^1$ has no heteroaromatic groups.

In some embodiments of Formula I, a>0 and at least one $R^1$ is an amino or deuterated amino group.

In some embodiments of Formula I, a>0 and at least one $R^1$ has Formula a

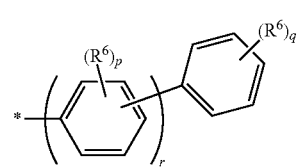

Formula a wherein:
R⁶ is the same or different at each occurrence and is selected from the group consisting of D, alkyl, alkoxy, siloxane, silyl, diarylamino, carbazolyl, deuterated alkyl, deuterated alkoxy, deuterated siloxane, deuterated silyl, deuterated diarylamino, and deuterated carbazolyl, where adjacent R⁶ groups can be joined together to form an fused aromatic ring or a deuterated fused aromatic ring;
p is the same or different at each occurrence and is an integer from 0-4;
q is an integer from 0-5;
r is an integer from 1 to 5; and
* indicates the point of attachment.

In some embodiments of Formula I, a>0 and at least one R¹ has Formula b

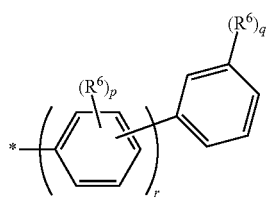

Formula b where R⁶, p, q, r and * are as in Formula a. In some embodiments of Formula I, a>0 and at least one R¹ is selected from the group consisting of phenyl, naphthyl, Formula a, and deuterated analogs thereof.

In some embodiments of Formula I, a>0 and at least one R¹ has one or more substituents selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula I, a>0 and at least one R¹ is an aryl group having one or more substituents selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula I, a=2 and R¹ groups at positions 1 and 2 are joined to form a 6-membered fused aromatic ring.

In some embodiments of Formula I, a=2 and R¹ groups at positions 2 and 3 are joined to form a 6-membered fused aromatic ring.

In some embodiments of Formula I, a=2 and R¹ groups at positions 3 and 4 are joined to form a 6-membered fused aromatic ring.

In some embodiments of Formula I, b=0.
In some embodiments of Formula I, b=1.
In some embodiments of Formula I, b=2.
In some embodiments of Formula I, b=3.
In some embodiments of Formula I, b>0.

All of the above-described embodiments for R¹ apply equally to R².

In some embodiments of Formula I, b=2 and R² groups at positions 5 and 6 are joined to form a 6-membered fused aromatic ring.

In some embodiments of Formula I, b=2 and R² groups at positions 6 and 7 are joined to form a 6-membered fused aromatic ring.

In some embodiments of Formula I, c=0.
In some embodiments of Formula I, c=1.
In some embodiments of Formula I, c=2.
In some embodiments of Formula I, c=3.
In some embodiments of Formula I, c>0.

All of the above-described embodiments for R¹ apply equally to R³.

In some embodiments of Formula I, c=2 and R³ groups at positions 8 and 9 are joined to form a 6-membered fused aromatic ring In some embodiments of Formula I, c=2 and R³ groups at positions 9 and 10 are joined to form a 6-membered fused aromatic ring.

In some embodiments of Formula I, a=b=c=1 and R¹, R², and R³ are amino or deuterated amino groups.

In some embodiments of Formula I, $R^4=R^5$.

In some embodiments of Formula I, $R^4 \neq R^5$.

In some embodiments of Formula I, R⁴ is selected from H and D.

In some embodiments of Formula I, R⁴ is selected from the group consisting of alkyl and deuterated alkyl having 1-12 carbons; in some embodiments, 3-8 carbons; in some embodiments 1-4 carbons.

In some embodiments of Formula I, R⁴ is selected from the group consisting of aryl and deuterated aryl.

In some embodiments of Formula I, R⁴ is selected from the group consisting of phenyl and deuterated phenyl.

In some embodiments of Formula I, R⁵ is selected from the group consisting of alkyl and deuterated alkyl having 1-12 carbons; in some embodiments, 3-8 carbons; in some embodiments 1-4 carbons.

In some embodiments of Formula I, R⁵ is selected from the group consisting of aryl and deuterated aryl.

In some embodiments of Formula I, R⁵ is selected from the group consisting of phenyl and deuterated phenyl.

In some embodiments of Formula I, R⁴ and R⁵ are joined together to form a 5- or 6-membered aliphatic ring.

In some embodiments of Formula I, R⁴ and R⁵ are phenyl groups which are joined together to form a spiro group.

In some embodiments of Formula I, $R^{4a}$ is an alkyl or deuterated alkyl having 1-20 carbons; in some embodiments, 1-12 carbons; in some embodiments, 3-8 carbons.

In some embodiments of Formula I, $R^{4a}$ is a hydrocarbon aryl group having 6-36 ring carbons. The hydrocarbon aryl group can include one or more single ring groups bonded together, one or more fused rings, or combinations thereof.

In some embodiments of Formula I, $R^{4a}$ has no heteroaromatic groups.

In some embodiments of Formula I, $R^{4a}$ has Formula a, as defined above.

In some embodiments of Formula I, $R^{4a}$ has Formula b, as defined above.

In some embodiments of Formula I, $R^{4a}$ is selected from the group consisting of phenyl, naphthyl, Formula a, and deuterated analogs thereof.

In some embodiments of Formula I, the compound has Formula I-a

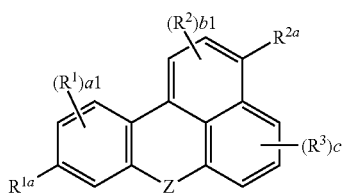

(I-a)

wherein:
- Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;
- $R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;
- $R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
- $R^{1a}$ and $R^{2a}$ are the same or different at each occurrence and are selected from the group consisting of D, aryl, heteroaryl, alkyl, amino, silyl, deuterated aryl, deuterated heteroaryl, deuterated alkyl, deuterated amino, and deuterated silyl;
- $R^{4a}$ is selected from the group consisting of alkyl, silyl, germyl, aryl, and deuterated analogs thereof;
- a1 and b1 are the same or different and are an integer from 0-2; and
- c is an integer from 0-3.

In some embodiments of Formula I-a, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic.

In some embodiments of Formula I-a, $R^{1a}$ is an alkyl or deuterated alkyl having 1-20 carbons; in some embodiments, 1-12 carbons; in some embodiments, 3-8 carbons.

In some embodiments of Formula I-a, $R^{1a}$ is a hydrocarbon aryl group having 6-36 ring carbons. The hydrocarbon aryl group can include one or more single ring groups bonded together, one or more fused rings, or combinations thereof.

In some embodiments of Formula I-a, $R^{1a}$ has no heteroaromatic groups.

In some embodiments of Formula I-a, $R^{1a}$ is an amino or deuterated amino group.

In some embodiments of Formula I-a; $R^{1a}$ has Formula a, as defined above.

In some embodiments of Formula I-a, $R^{1a}$ has Formula b, as defined above,

In some embodiments of Formula I-a, $R^{1a}$ is selected from the group consisting of phenyl, naphthyl, Formula a, and deuterated analogs thereof.

In some embodiments of Formula I-a, $R^{1a}$ has one or more substituents selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula I-a, $R^{2a}$ is an alkyl or deuterated alkyl having 1-20 carbons; in some embodiments, 1-12 carbons; in some embodiments, 3-8 carbons.

In some embodiments of Formula I-a, $R^{2a}$ is a hydrocarbon aryl group having 6-36 ring carbons. The hydrocarbon aryl group can include one or more single ring groups bonded together, one or more fused rings, or combinations thereof.

In some embodiments of Formula I-a, $R^{2a}$ has no heteroaromatic groups.

In some embodiments of Formula I-a, $R^{2a}$ is an amino or deuterated amino group.

In some embodiments of Formula I-a, $R^{2a}$ has Formula a, as defined above.

In some embodiments of Formula I-a, $R^{2a}$ has Formula b, as defined above.

In some embodiments of Formula I-a, $R^{2a}$ is selected from the group consisting of phenyl, naphthyl, Formula a, and deuterated analogs thereof.

In some embodiments of Formula I-a, $R^{2a}$ has one or more substituents selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula I-a, a1=0.
In some embodiments of Formula I-a, a1=1.
In some embodiments of Formula I-a, a1=2.
In some embodiments of Formula I-a, a1=3.
In some embodiments of Formula I-a, a1>0 and the embodiments for $R^1$ described above for Formula I, apply equally to Formula I-a.
In some embodiments of Formula I-a, b1=0.
In some embodiments of Formula I-a, b1=1.
In some embodiments of Formula I-a, b1=2.
In some embodiments of Formula I-a, b1>0 and the embodiments for $R^2$ described above for Formula I, apply equally to Formula I-a.

The embodiments for Z, $R^3$, $R^4$, $R^{4a}$, $R^5$, and c described above for Formula I, apply equally to Formula I-a.

In some embodiments of Formula I, Z is $CR^4R^5$, a>0 and at least one $R^3$ is at position 10. In some embodiments, $R^5$ and $R^3$ are joined together to form a fused aromatic or heteroaromatic ring.

In some embodiments of Formula I, the compound has Formula I-b

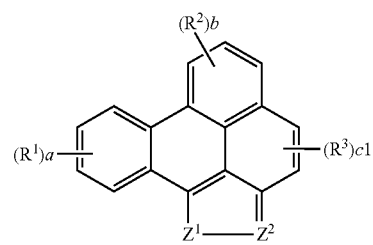

(I-b)

wherein:
- $Z^1$ is selected from the group consisting of $NR^{4a}$, $PR^{4a}$, $P(O)R^{4a}$, O, S, SO, $SO_2$, Se; SeO, $SeO_2$, Te, TeO, and $TeO_2$;

$Z^2$ is selected from the group consisting of $CR^4$ and N;

$R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;

$R^4$ is selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;

$R^{4a}$ is selected from the group consisting of alkyl, silyl, germyl, aryl, and deuterated analogs thereof;

a is an integer from 0-4;

b is an integer from 0-3; and c1 is an integer from 0-2.

In some embodiments of Formula I-b, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic.

In some embodiments of Formula I-b, $Z^1$ is $NR^{4a}$.

In some embodiments of Formula I-b, $Z^1$ is selected from the group consisting of $PR^{4a}$ and $P(O)R^{4a}$.

In some embodiments of Formula I-b, $Z^1$ is selected from the group consisting of O, S, SO, $SO_2$, Se, and Te, In some embodiments of Formula I-b, $Z^1$ is O.

In some embodiments of Formula I-b, $Z^1$ is S.

In some embodiments of Formula I-b, $Z^1$ is SO.

In some embodiments of Formula I-b, $Z^1$ is $SO_2$.

In some embodiments of Formula I-b, $Z^1$ is Se.

In some embodiments of Formula I-b, $Z^2$ is N.

In some embodiments of Formula I-b, $Z^2$ is $CR^4$.

In some embodiments of Formula I-b, c1=0.

In some embodiments of Formula I-b, c1=1.

In some embodiments of Formula I-b, c1=2.

In some embodiments of Formula I-b, c1>0.

The embodiments for $R^1$, $R^2$, $R^3$, $R^4$, $R^{4a}$, $R^5$, a, and b described above for Formula I, apply equally to Formula I-b.

In some embodiments of Formula I, Z is $NR^{4a}$, a>0 and at least one $R^3$ is at position 10. In some embodiments, $R^{4a}$ and $R^3$ are joined together to form a fused aromatic or heteroaromatic ring.

In some embodiments of Formula I, the compound has Formula I-c

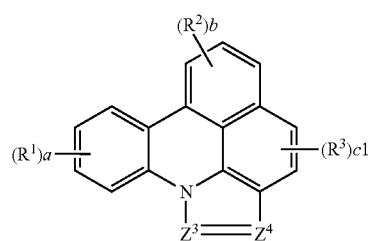

(I-c)

wherein:

$Z^3$ and $Z^4$ are the same or different and are selected from the group consisting of $CR^{5a}$ and N;

$R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;

$R^{5a}$ is the same or different at each occurrence and is selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl, where adjacent $R^{5a}$ groups can be joined to form a fused aromatic or heteroaromatic ring;

a is an integer from 0-4;

b is an integer from 0-3; and c1 is an integer from 0-2.

In some embodiments of Formula I-c, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic.

In some embodiments of Formula I-c, $Z^3$=$Z^4$.

In some embodiments of Formula I-c, $Z^3$≠$Z^4$.

In some embodiments of Formula I-c, $Z^3$ is N.

In some embodiments of Formula I-c, $Z^3$ is $CR^{5a}$.

In some embodiments of Formula I-c, $Z^4$ is N.

In some embodiments of Formula I-c, $Z^4$ is $CR^{5a}$.

In some embodiments of Formula I-c, $R^{5a}$ is selected from H and D.

In some embodiments of Formula I-c, $R^{5a}$ is selected from the group consisting of alkyl and deuterated alkyl having 1-12 carbons; in some embodiments, 3-8 carbons; in some embodiments 1-4 carbons.

In some embodiments of Formula I-c, $R^{5a}$ is selected from the group consisting of aryl and deuterated aryl.

In some embodiments of Formula I-c, $R^{5a}$ is selected from the group consisting of phenyl and deuterated phenyl.

The embodiments for $R^1$, $R^2$, $R^3$, a, and c1 described above for Formula I-b, apply equally to Formula I-c.

Any of the above embodiments for Formula I can be combined with one or more of the other embodiments, so long as they are not mutually exclusive. For example, the embodiment in which a=2 can be combined with the embodiment in which at least one $R^1$ is naphthyl and the embodiment in which at least one $R^1$ has formula a. And, for example, the embodiment in which the compound has Formula I-b, can be combined with the embodiment in which $Z^1$ is $NR^{4a}$ and $R^{4a}$ is aryl. The same is true for the other non-mutually-exclusive embodiments discussed above. The skilled person would understand which embodiments were mutually exclusive and would thus readily be able to determine the combinations of embodiments that are contemplated by the present application.

The compounds of Formula I can be made using any technique that will yield a C—C or C—N bond. A variety of such techniques are known, such as Suzuki, Yamamoto, Stille, and Pd- or Ni-catalyzed C—N couplings.

Compounds having Formula I wherein Z is $CR^4R^5$ and $R^4$ and $R^5$ are alkyl can be prepared by the method shown below in which the dibromobenzanthracene intermediate (4) is made in three steps from commercially available benzanthrene (1).

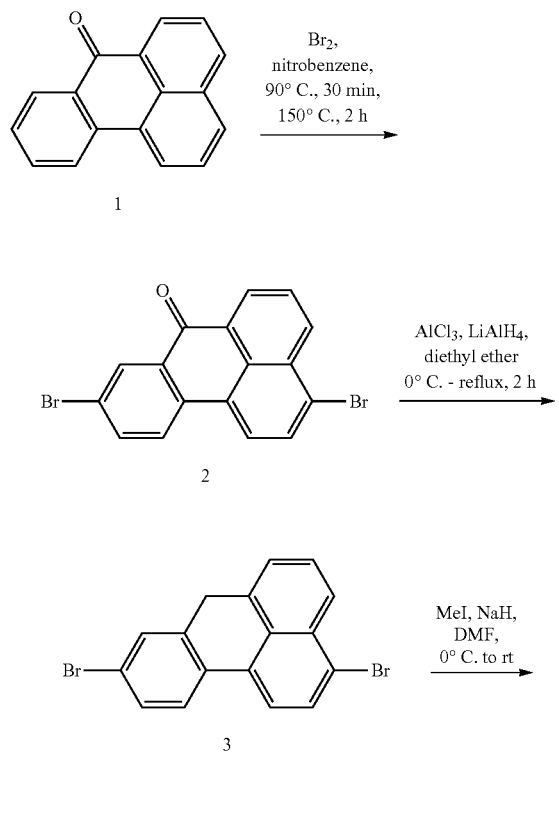

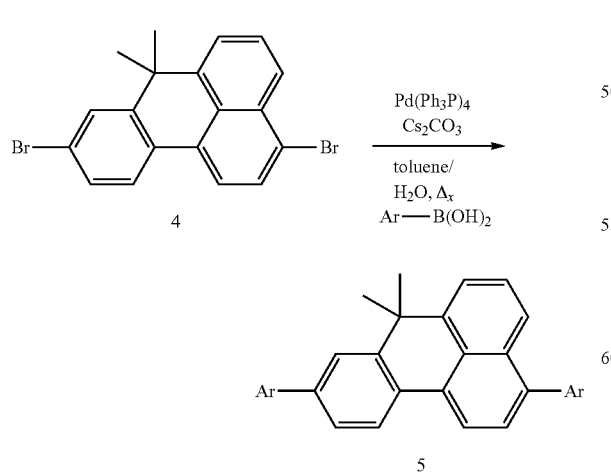

Compounds having Formula I wherein Z is CR⁴R⁵ and R¹ and R² are aryl can be prepared by the palladium-catalyzed cross-coupling of a halogenated benzanthracene such as (4) with appropriate arylboronic acids or arylboronate esters.

Compounds having Formula I wherein Z is CR⁴R⁵ and R¹ and R² are arylamine substituents can be prepared by the palladium-catalyzed amination of a halogenated benzanthracene such as (4) with appropriate aromatic amines.

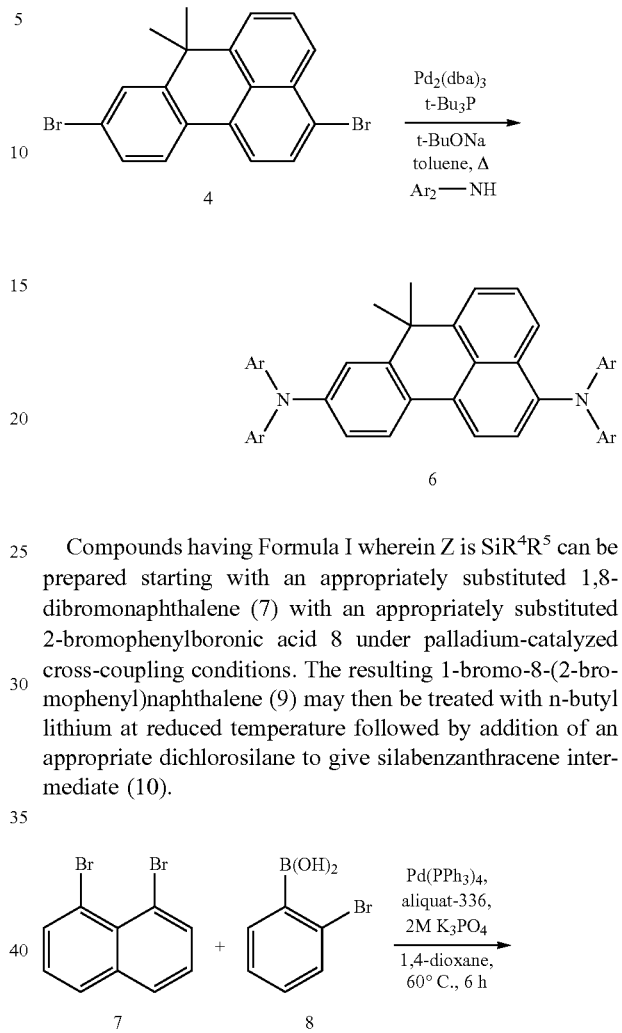

Compounds having Formula I wherein Z is SiR⁴R⁵ can be prepared starting with an appropriately substituted 1,8-dibromonaphthalene (7) with an appropriately substituted 2-bromophenylboronic acid 8 under palladium-catalyzed cross-coupling conditions. The resulting 1-bromo-8-(2-bromophenyl)naphthalene (9) may then be treated with n-butyl lithium at reduced temperature followed by addition of an appropriate dichlorosilane to give silabenzanthracene intermediate (10).

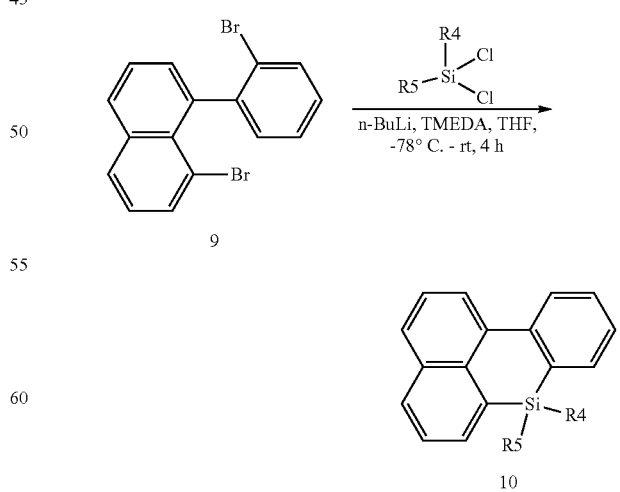

The compounds having Formula I wherein Z is SiR⁴R⁵ and R⁴ and R⁵ are each alkyl can be prepared by reaction of silabenzanthracene intermediate (10) with excess bis(pinacolato)diboron (11), an iridium (I) precatalyst and a bipyridyl ligand to give a separable mixture of two tris-borylated regioisomers (12) and (13).

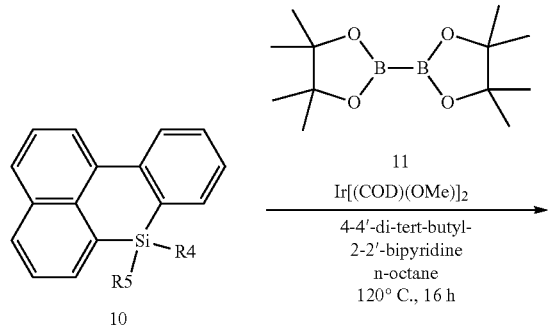

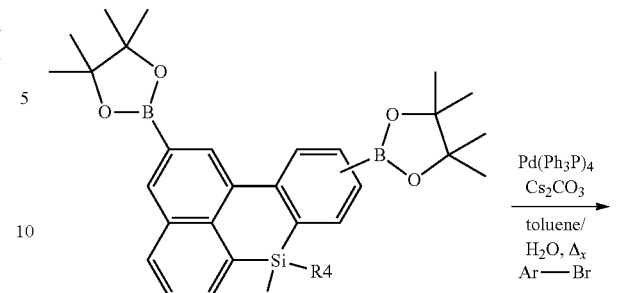

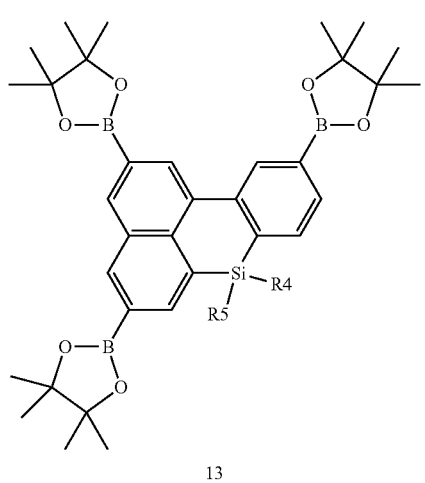

The compounds having Formula I wherein Z is $SiR^4R^5$ and $R^1$, $R^2$ and $R^3$ are aryl can be prepared by the palladium-catalyzed cross-coupling of suitable borylated silabenzanthracenes such as (12) and (13) with appropriate aryl halides.

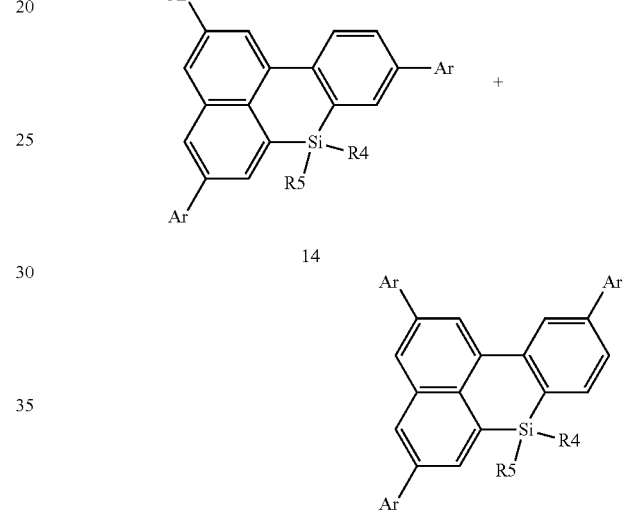

The tris-borylated isomers (12) and (13) can then be bromodeborylated by treatment with copper(II) bromide in aqueous methanol/tetrahydrofuran to give the tribromo regioisomers (16) and (17).

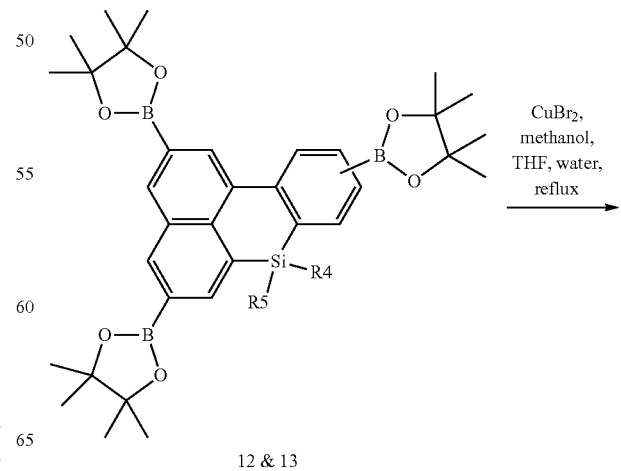

-continued

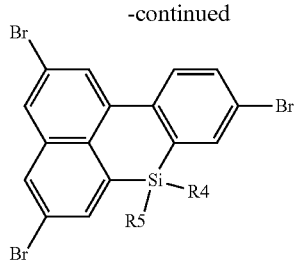

16

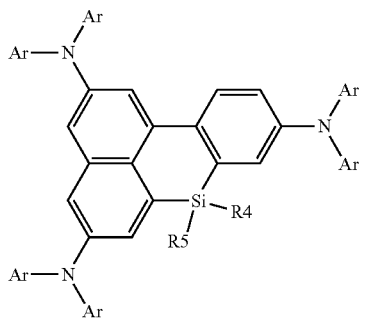

18

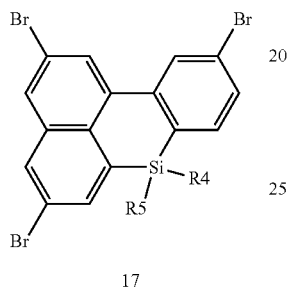

17

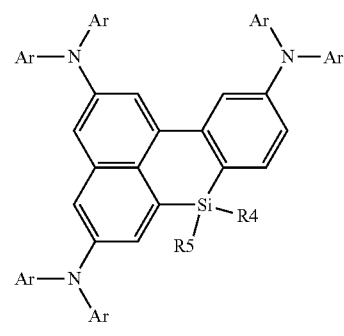

19

The compounds having Formula I wherein Z is SiR⁴R⁵ and $R^1$, $R^2$ and $R^3$ are arylamine substituents can be prepared by the palladium-catalyzed amination of suitable halogenated silabenzanthracenes such as (16) and (17) with appropriate aromatic amines.

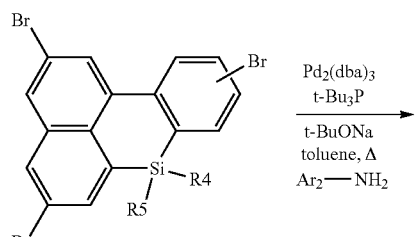

16 & 17

Deuterated compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum dichloride.

Exemplary preparations are given in the Examples.

Some non-limiting examples of compounds having Formula I are shown below.

Compound I-1

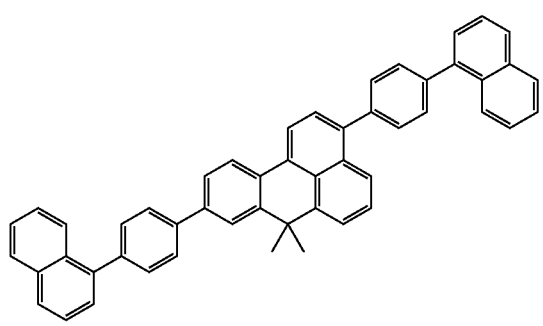

Compound I-2

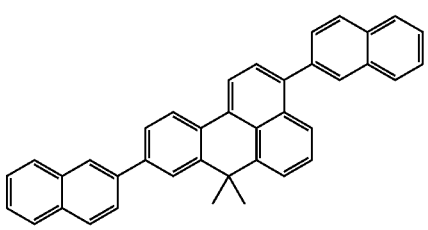

-continued
Compound I-3
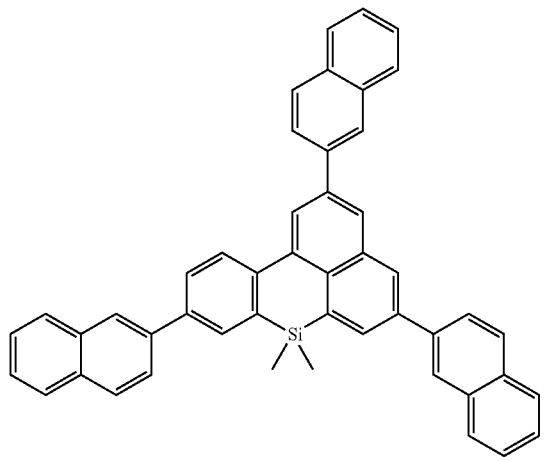
Compound I-4
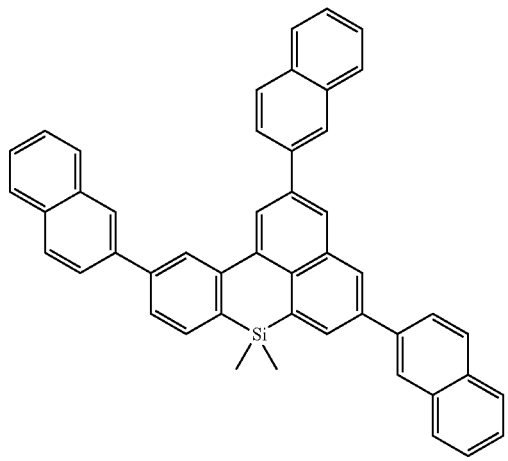
Compound I-5
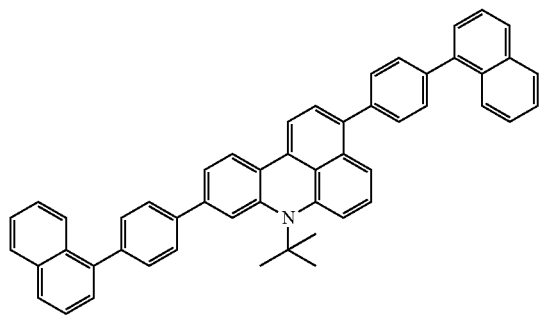
Compound I-6
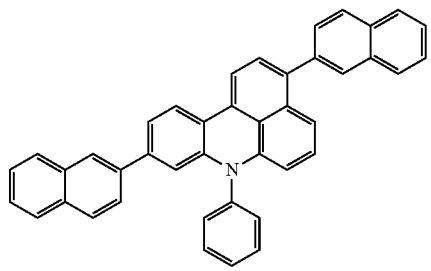
Compound I-7
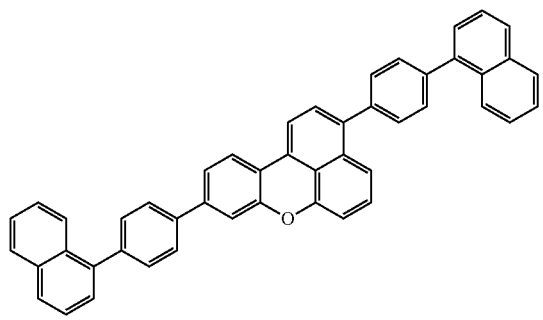
Compound I-8
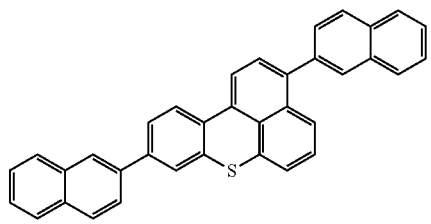
Compound I-9
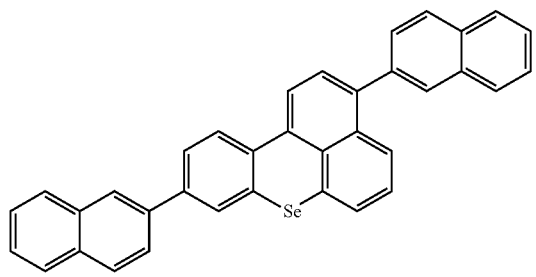
Compound I-10
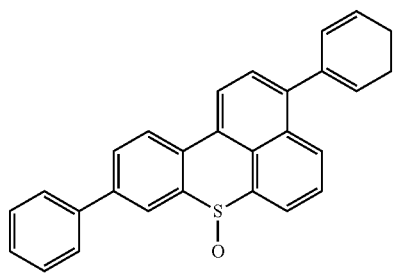

-continued
Compound I-11
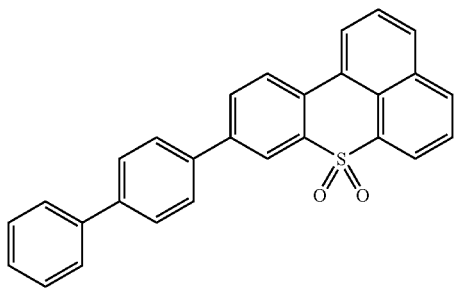
Compound I-12
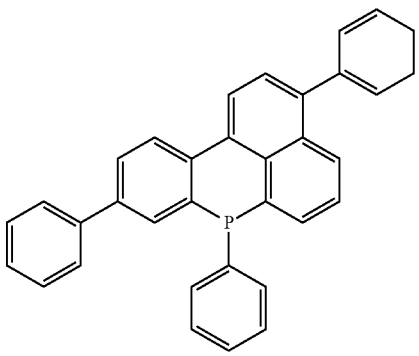
Compound I-13
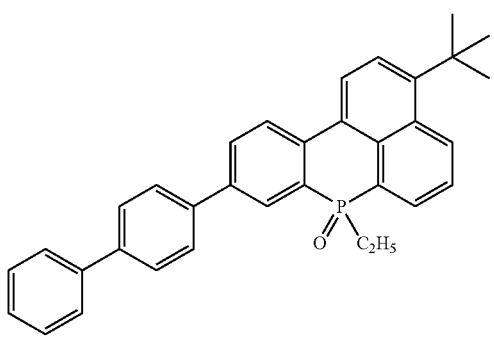
Compound I-14
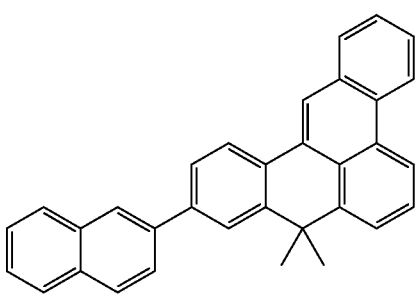
Compound I-15
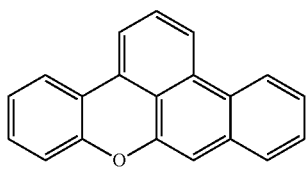
Compound I-16
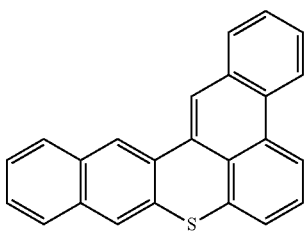
Compound I-17
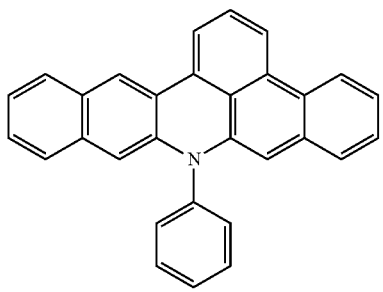
Compound I-18
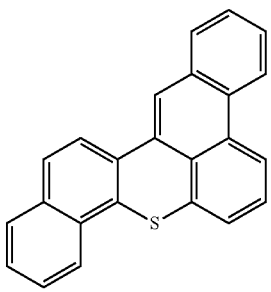

-continued
Compound I-19
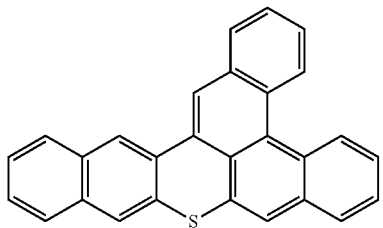
Compound I-20
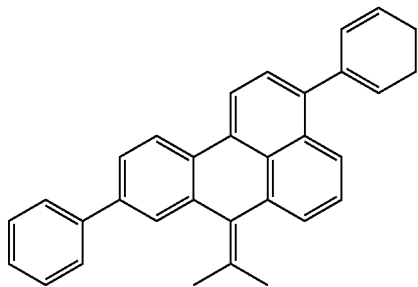
Compound I-21
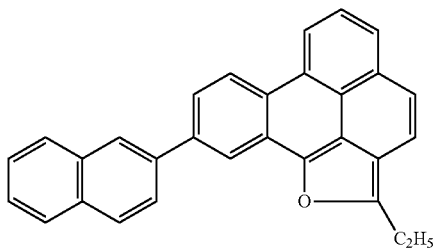
Compound I-22
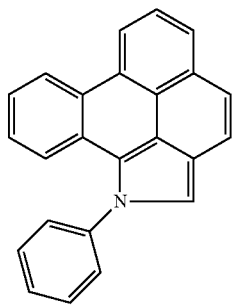
Compound I-23
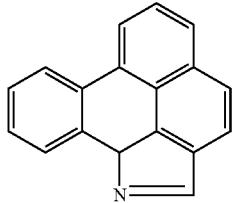
Compound I-24
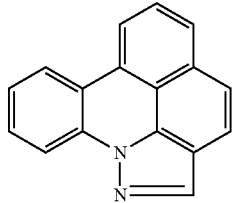
Compound I-25
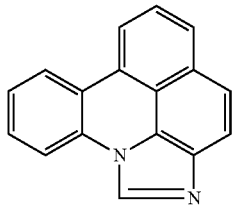
Compound I-26
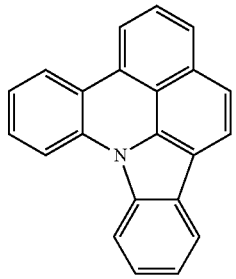
Compound I-27
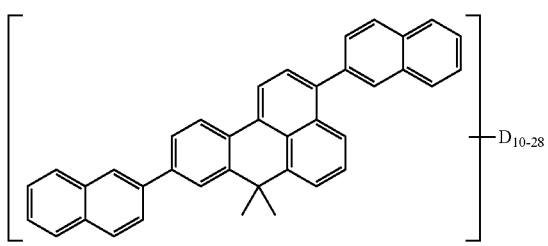

Compound I-28
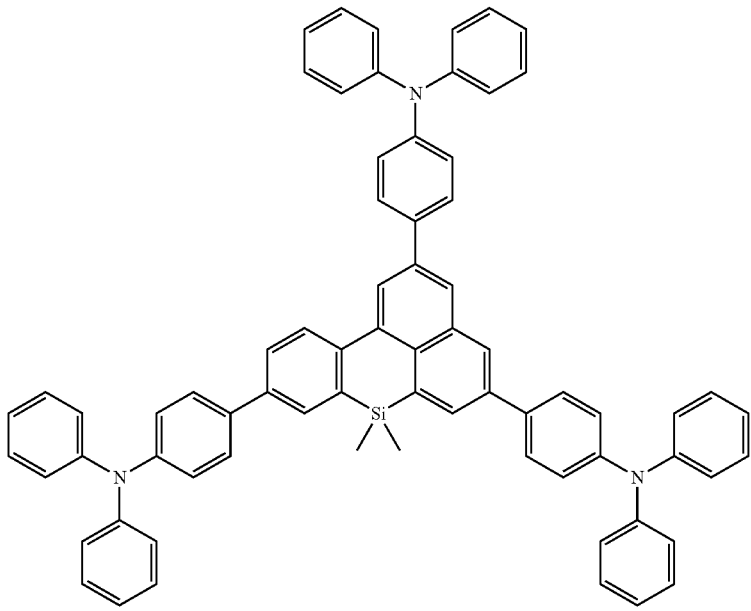
Compound I-29
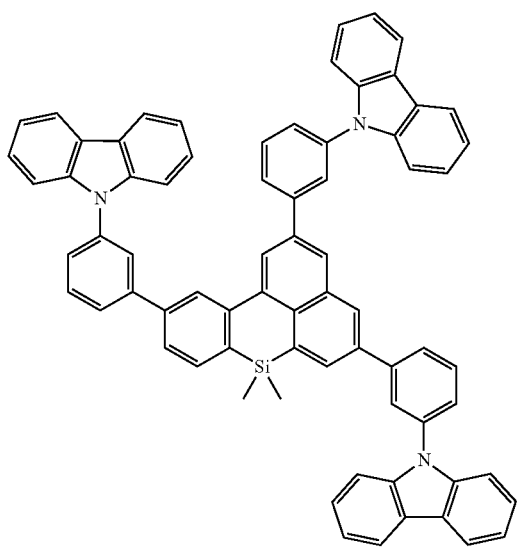
Compound I-30
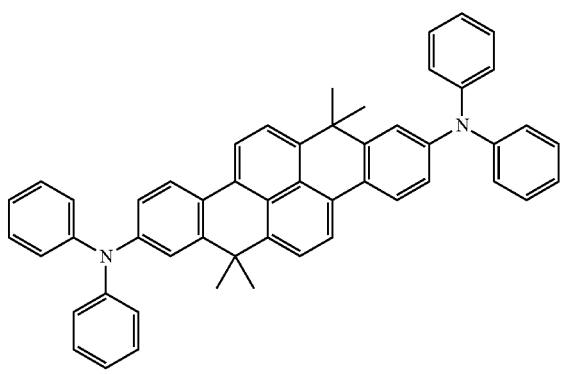
Compound I-31
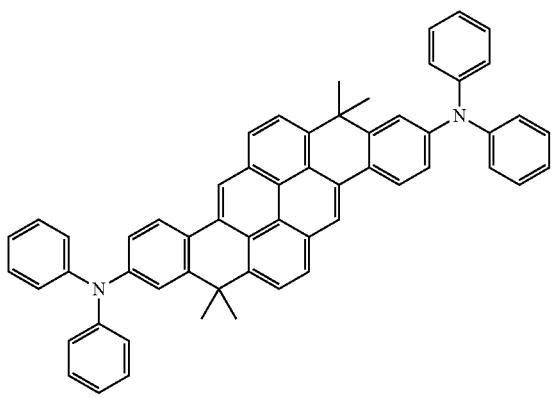

The compounds can be formed into layers for electronic devices. The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous liquid deposition techniques, include but are not limited to, spin coating, gravure coating, curtain coating, dip coating, slot-die coating, spray coating, and continuous nozzle coating. Discontinuous liquid deposition techniques include, but are not limited to, ink jet printing, gravure printing, and screen printing.

In some embodiments, the new compounds having Formula I can be used as hole transport materials in devices.

In some embodiments, the new compounds having Formula I are electroluminescent and can be used as emissive materials in devices. In some embodiments, the compounds are blue light-emitting. The term "blue light-emitting" is intended to mean a material capable of emitting radiation that has an emission maximum at a wavelength in a range of approximately 400-500 nm. In some embodiments, the emission maximum is at a wavelength in a range of approximately 445-490 nm.

In some embodiments, the compounds having Formula I have a photoluminescence y-coordinate of less than 0.15, according to the C.I.E. chromaticity scale (Commission Internationale de L'Eclairage, 1931); in some embodiments, less than 0.10; in some embodiments, less than 0.090.

In some embodiments, electroluminescent devices including the compounds of Formula I as emissive materials have deep blue color. In some embodiments, the blue emission has an x-coordinate less than 0.15 and a y-coordinate less than 0.10, according to the C.I.E. chromaticity scale; in some embodiments, the y-coordinate is less than 0.090.

In some embodiments, the new compounds having Formula I can be used as hosts for electroluminescent materials.

In some embodiments, the new compounds having Formula I can be used as electron transport materials in devices.

3. Compound Having Formula II-a, Formula II-b, or Formula II-c

In some embodiments, the compound having Formula II-a, Formula II-b, or Formula II-c is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated, In some embodiments, the electroactive compound has Formula II-a

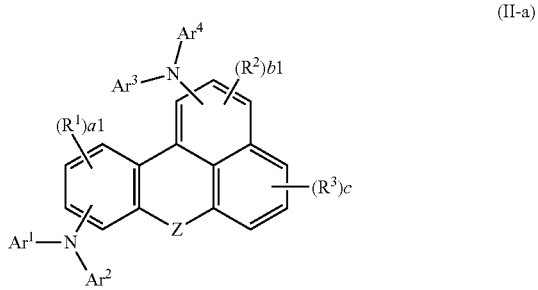

(II-a)

wherein:

Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;

$Ar^1$-$Ar^4$ are the same or different and are selected from the group consisting of aryl groups, heteroaryl groups, and deuterated analogs thereof;

$R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;

$R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;

$R^{4a}$ is selected from the group consisting of alkyl, silyl, germyl, aryl, and deuterated analogs thereof;

a1 and c are the same or different and are an integer from 0-3; and b1 is an integer from 0-2.

In some embodiments of Formula II-a, adjacent $R^1$ or adjacent $R^2$ or adjacent $R^3$ groups can be joined together to form a fused ring, In some embodiments, the fused ring is aromatic. In some embodiments, the fused ring is a hydrocarbon aromatic, In some embodiments, the fused ring is a heteroaromatic.

In some embodiments of Formula II-a, at least one $R^2$ is present at position 7, as defined above, and at least one $R^3$ is present at position 8, as defined above.

In some embodiments of Formula II-a, $R^2$ at position 7 and $R^3$ at position 8 are joined together to form a fused ring group. In some embodiments, the fused ring group comprises a single fused ring. In some embodiments, the fused ring group comprises more than one fused ring.

In some embodiments, the fused ring group is a hydrocarbon aromatic. In some embodiments, the fused ring group is a heteroaromatic. In some embodiments, the fused ring group is non-aromatic.

In some embodiments, the fused ring group has 5-15 ring carbons; in some embodiments, 6-10 ring carbons.

In some embodiments, the fused ring group is unsubstituted.

In some embodiments, the fused ring group is substituted. In some embodiments, the substituents are selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula II-a, an amino nitrogen is bonded to position 1 on the fused ring core, as defined above.

In some embodiments of Formula II-a, an amino nitrogen is bonded to position 2 on the fused ring core, as defined above.

In some embodiments of Formula II-a, an amino nitrogen is bonded to position 3 on the fused ring core, as defined above.

In some embodiments of Formula II-a, an amino nitrogen is bonded to position 4 on the fused ring core, as defined above.

In some embodiments of Formula II-a, an amino nitrogen is bonded to position 5 on the fused ring core, as defined above.

In some embodiments of Formula II-a, an amino nitrogen is bonded to position 6 on the fused ring core, as defined above.

In some embodiments of Formula II-a, an amino nitrogen is bonded to position 7 on the fused ring core, as defined above.

In some embodiments of Formula II-a, $Ar^1=Ar^2$.
In some embodiments of Formula II-a, $Ar^1 \neq Ar^2$.
In some embodiments of Formula II-a, $Ar^3=Ar^4$.
In some embodiments of Formula II-a, $Ar^3 \neq Ar^4$.
In some embodiments of Formula II-a, $Ar^1=Ar^3$.
In some embodiments of Formula II-a, $Ar^2=Ar^4$.

In some embodiments of Formula II-a, $Ar^1$ is a hydrocarbon aryl group having 6-36 ring carbons. The hydrocarbon more single ring groups bonded together, one or more fused rings, or combinations thereof.

In some embodiments of Formula II-a, $Ar^1$ has no heteroaromatic groups.

In some embodiments of Formula II-a, $Ar^1$ has Formula a, as defined above.

In some embodiments of Formula II-a, $Ar^1$ has Formula b, as defined above.

In some embodiments of Formula II-a, $Ar^1$ is selected from the group consisting of phenyl, naphthyl, Formula a, and deuterated analogs thereof.

In some embodiments of Formula II-a, $Ar^1$ has one or more substituents selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

All of the above-described embodiments for $Ar^1$, apply equally to $Ar^2$, $Ar^3$, and $Ar^4$.

In some embodiments of Formula II-a, a1=0.
In some embodiments of Formula II-a, a1=1.
In some embodiments of Formula II-a, a1=2.
In some embodiments of Formula II-a, a1=3.

In some embodiments of Formula I-a, a1>0 and the embodiments for $R^1$ described above for Formula I, apply equally to Formula II-a.

In some embodiments of Formula II-a, b1=0.
In some embodiments of Formula II-a, b1=1.
In some embodiments of Formula II-a, b1=2.

In some embodiments of Formula II-a, b1>0 and the embodiments for $R^2$ described above for Formula I, apply equally to Formula I-a.

In some embodiments of Formula I-a, a1+b1+c≥1.

The embodiments for Z, $R^3$, $R^4$, $R^{4a}$, $R^5$, and c described above for Formula I, apply equally to Formula II-a.

In some embodiments, the electroactive compound has Formula II-b

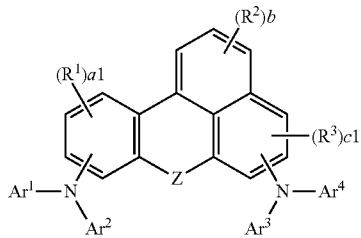

(II-b)

wherein:
Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;

$Ar^1$-$Ar^4$ are the same or different and are selected from the group consisting of aryl groups, heteroaryl groups, and deuterated analogs thereof;

$R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;

$R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;

$R^{4a}$ is selected from the group consisting of alkyl, silyl, germyl, aryl, and deuterated analogs thereof;

a1 and b are the same or different and are an integer from 0-3; and c1 is an integer from 0-2.

In some embodiments of Formula II-b, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic.

In some embodiments of Formula II-b, at least one $R^2$ is present at position 7, as defined above, and at least one $R^3$ is present at position 8, as defined above.

In some embodiments of Formula II-b, $R^2$ at position 7 and $R^3$ at position 8 are joined together to form a fused ring group. In some embodiments, the fused ring group comprises a single fused ring. In some embodiments, the fused ring group comprises more than one fused ring.

In some embodiments, the fused ring group is a hydrocarbon aromatic. In some embodiments, the fused ring group is a heteroaromatic, In some embodiments, the fused ring group is non-aromatic.

In some embodiments, the fused ring group has 5-15 ring carbons; in some embodiments, 6-10 ring carbons.

In some embodiments, the fused ring group is unsubstituted.

In some embodiments, the fused ring group is substituted, In some embodiments, the substituents are selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula II-b, an amino nitrogen is bonded to position 1 on the fused ring core, as defined above.

In some embodiments of Formula an amino nitrogen is bonded to position 2 on the fused ring core, as defined above.

In some embodiments of Formula II-b, an amino nitrogen is bonded to position 3 on the fused ring core, as defined above.

In some embodiments of Formula II-b, an amino nitrogen is bonded to position 4 on the fused ring core, as defined above.

In some embodiments of Formula an amino nitrogen is bonded to position 8 on the fused ring core, as defined above.

In some embodiments of Formula II-b, an amino nitrogen is bonded to position 9 on the fused ring core, as defined above.

In some embodiments of Formula II-b, an amino nitrogen is bonded to position 10 on the fused ring core, as defined above.

In some embodiments of Formula II-b, b>0 and and the embodiments for $R^2$ described above for Formula I, apply equally to Formula II-b.

In some embodiments of Formula II-b, c1=0.
In some embodiments of Formula II-b, c1=1.
In some embodiments of Formula II-b, c1=2.

In some embodiments of Formula II-b, c1>0 and and the embodiments for $R^3$ described above for Formula I, apply equally to Formula II-b.

In some embodiments of Formula II-b, a1+b+c1≥1.

The embodiments for Z, $Ar^1$, $Ar^2$, $Ar^3$, $A^4$, $R^1$, $R^2$, $R^4$, $R^{4a}$, $R^5$, and a1 described above for Formula II-a, apply equally to Formula II-b.

In some embodiments, the electroactive compound has Formula II-c

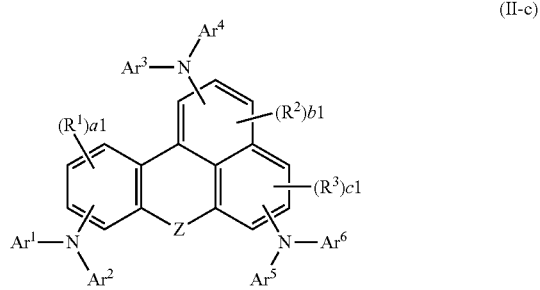

(II-c)

wherein:
Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;
$Ar^1$-$Ar^6$ are the same or different and are selected from the group consisting of aryl groups, heteroaryl groups, and deuterated analogs thereof;
$R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;
$R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
$R^{4a}$ is selected from the group consisting of alkyl, silyl, germyl, aryl, and deuterated analogs thereof;
a1 is an integer from 0-3; and
b1 and c1 are the same or different and are an integer from 0-2.

In some embodiments of Formula II-c, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic.

In some embodiments of Formula II-c, at least one $R^2$ is present at position 7, as defined above, and at least one $R^3$ is present at position 8, as defined above.

In some embodiments of Formula II-c, $R^2$ at position 7 and $R^3$ at position 8 are joined together to form a fused ring group. In some embodiments, the fused ring group comprises a single fused ring. In some embodiments, the fused ring group comprises more than one fused ring.

In some embodiments, the fused ring group is a hydrocarbon aromatic. In some embodiments, the fused ring group is a heteroaromatic, In some embodiments, the fused ring group is non-aromatic.

In some embodiments, the fused ring group has 5-15 ring carbons; in some embodiments, 6-10 ring carbons.

In some embodiments, the fused ring group is unsubstituted.

In some embodiments, the fused ring group is substituted. In some embodiments, the substituents are selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula II-c, an amino nitrogen is bonded to position 1 on the fused ring core, as defined above.

In some embodiments of Formula II-c, an amino nitrogen is bonded to position 2 on the fused ring core, as defined above.

In some embodiments of Formula II-c, an amino nitrogen is bonded to position 3 on the fused ring core, as defined above.

In some embodiments of Formula II-c, an amino nitrogen is bonded to position 4 on the fused ring core, as defined above.

In some embodiments of Formula II-c, an amino nitrogen is bonded to position 5 on the fused ring core, as defined above.

In some embodiments of Formula II-c, an amino nitrogen is bonded to position 6 on the fused ring core, as defined above.

In some embodiments of Formula II-c, an amino nitrogen is bonded to position 7 on the fused ring core, as defined above.

In some embodiments of Formula II-c, an amino nitrogen is bonded to position 8 on the fused ring core, as defined above.

In some embodiments of Formula II-c, an amino nitrogen is bonded to position 9 on the fused ring core, as defined above.

In some embodiments of Formula II-c, an amino nitrogen is bonded to position 10 on the fused ring core, as defined above.

The embodiments for Z, $Ar^1$, $Ar^2$, $Ar^3$, $Ar^4$, $R^1$, $R^2$, $R^4$, $R^{4a}$, $R^5$, a1, and b1 described above for Formula II-a, apply equally to Formula II-c.

The embodiments for c1 described above for Formula II-b, apply equally to Formula II-c.

In some embodiments, the compound of Formula II-a has Formula II-a1

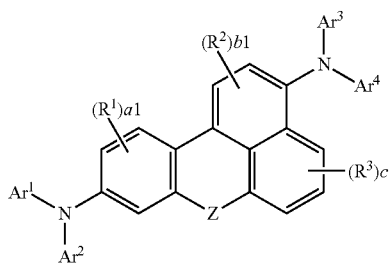

(II-a1)

wherein:
- Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;
- $Ar^1$-$Ar^4$ are the same or different and are selected from the group consisting of aryl groups, heteroaryl groups, and deuterated analogs thereof;
- $R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;
- $R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
- $R^{4a}$ is selected from the group consisting of alkyl, silyl, germyl, aryl, and deuterated analogs thereof;
- a1 and c are the same or different and are an integer from 0-3; and
- b1 is an integer from 0-2.

In some embodiments of Formula II-a1, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic.

The embodiments for Z, $Ar^1$, $Ar^2$, $Ar^3$, $A^4$, $R^1$, $R^2$, $R^3$, $R^4$, $R^{4a}$, $R^5$, a1, b1, and c described above for Formula II-a, apply equally to Formula II-a1.

Any of the above embodiments for Formula II-a, Formula II-b, or Formula II-c can be combined with one or more of the other embodiments, so long as they are not mutually exclusive. For example, the embodiment in which Z is $CR^4R^5$ can be combined with the embodiment in which $Ar^1$ is naphthyl and the embodiment in which $Ar^2$ has formula a. The same is true for the other non-mutually-exclusive embodiments discussed above. The skilled person would understand which embodiments were mutually exclusive and would thus readily be able to determine the combinations of embodiments that are contemplated by the present application.

The compounds of Formula II-a, Formula II-a, or Formula II-c can be made using any technique that will yield a C—C or C—N bond. A variety of such techniques are known, such as Suzuki, Yamamoto, Stille, and Pd- or Ni-catalyzed C—N couplings. Synthetic methods similar to those used in the preparation of compounds of Formula I above may be used to produce compounds of Formula II-a and Formula II-b.

Deuterated compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum dichloride.

Exemplary preparations are given in the Examples.

Some non-limiting examples of compounds having Formula II-a, II-b, or II-c are shown below.

Compound II-1

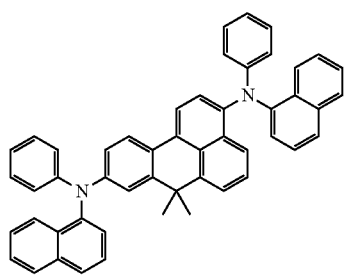

Compound II-2

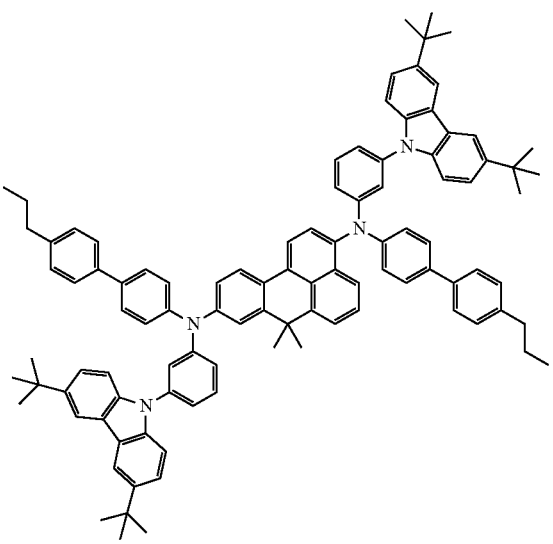

-continued
Compound II-3
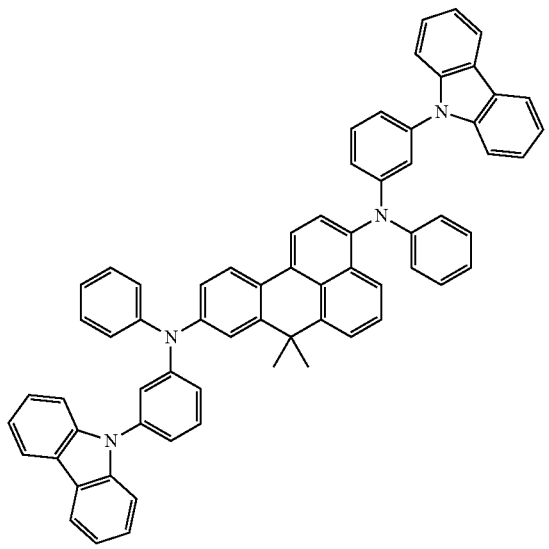
Compound II-4
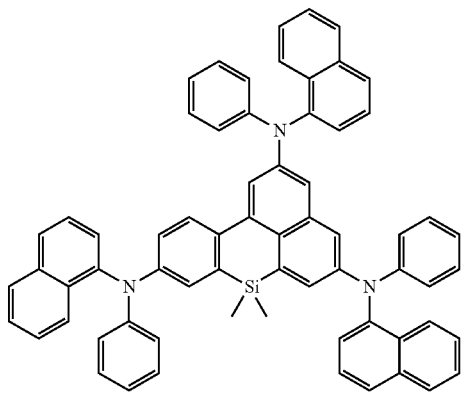
Compound II-5
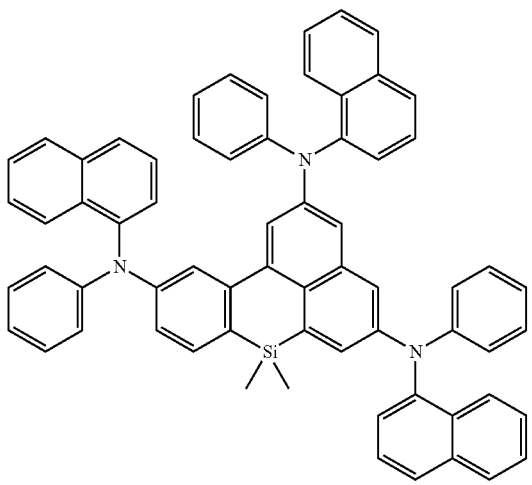
Compound II-6
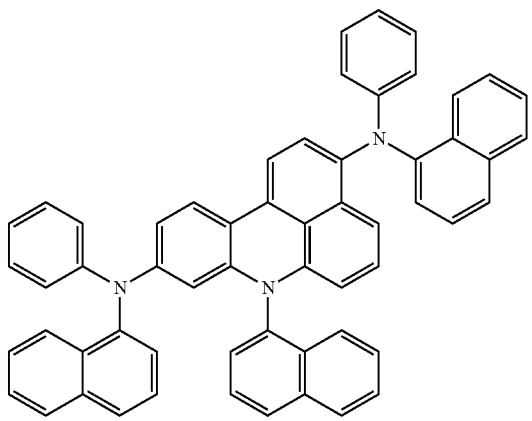
Compound II-7
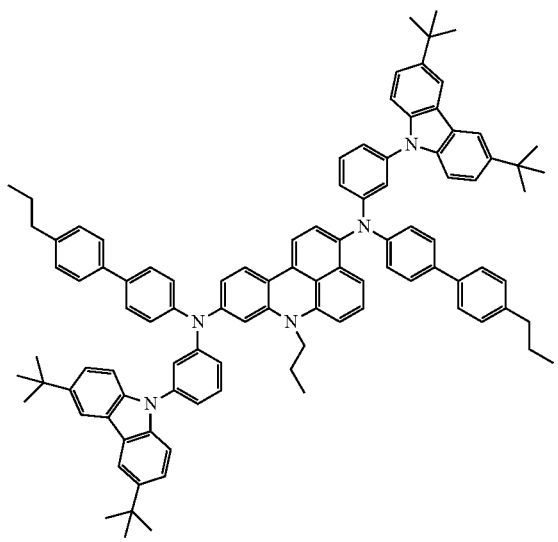
Compound II-8
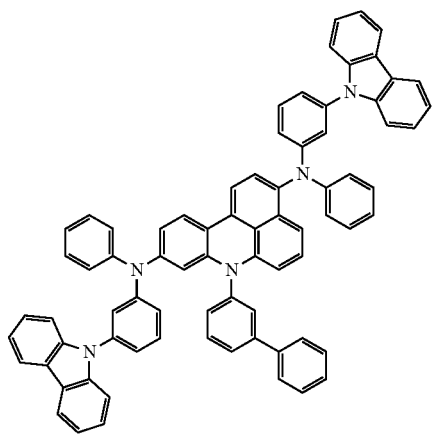

-continued
Compound II-9
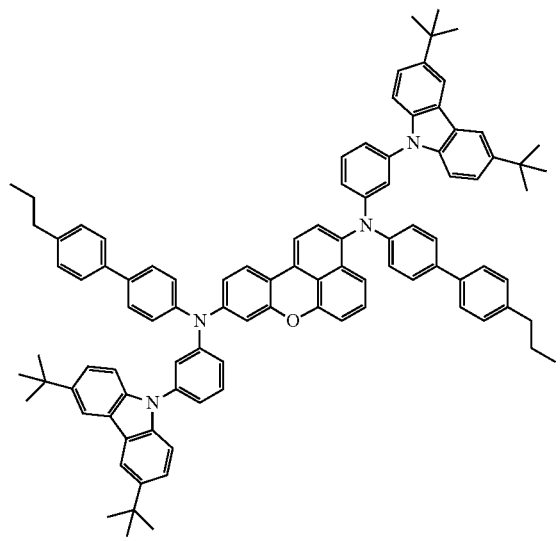
Compound II-10
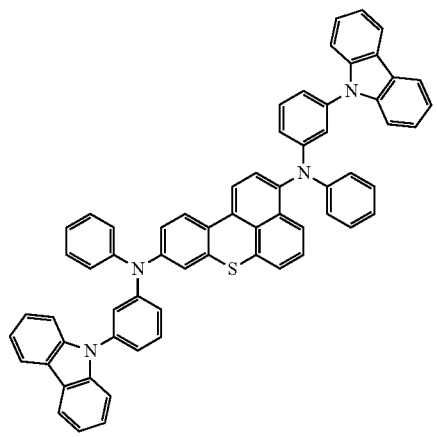
Compound II-11
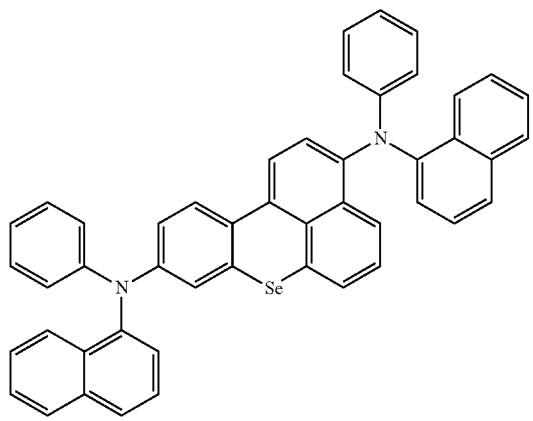
Compound II-12
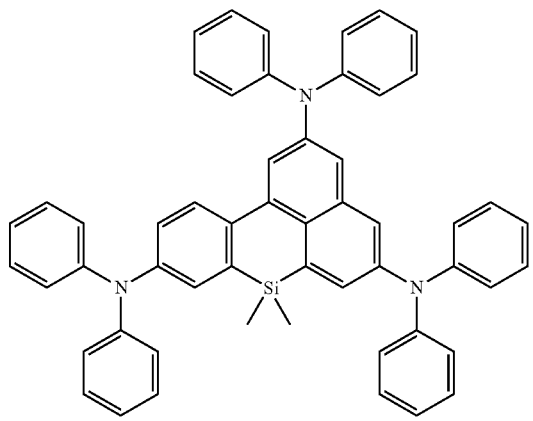
Compound II-13
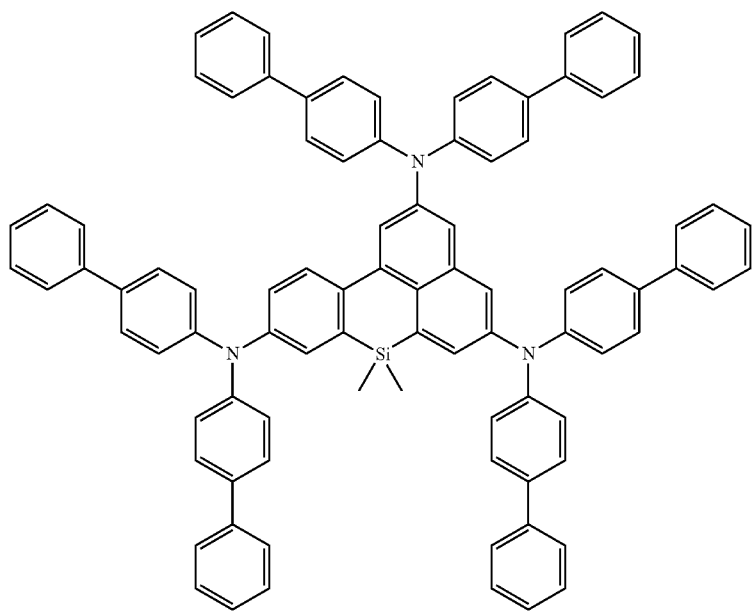

-continued

Compound II-14

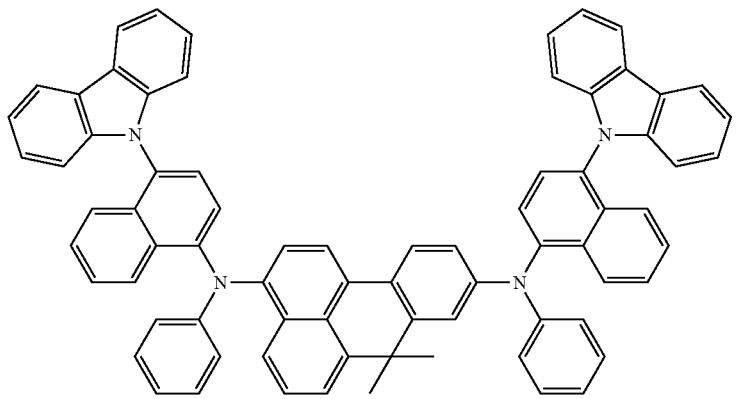

Compound II-15

Compound II-16

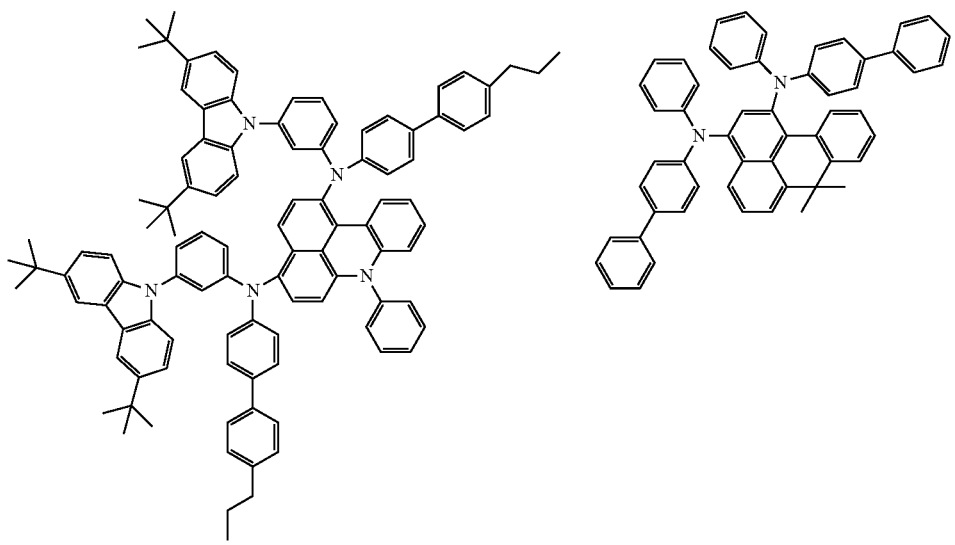

The compounds can be formed into layers for electronic devices, as described above.

In some embodiments, the new compounds having Formula II-a, Formula II-b, or Formula II-c can be used as hole transport materials in devices.

In some embodiments, the new compounds having Formula II-a, Formula II-b, or Formula II-c are electroluminescent and can be used as emissive materials in devices. In some embodiments, the compounds are blue light-emitting.

In some embodiments, the compounds having Formula II-a, Formula II-b, or Formula II-c have a photoluminescence y-coordinate of less than 0.15, according to the C.I.E. chromaticity scale; in some embodiments, less than 0.10; in some embodiments, less than 0.090.

In some embodiments, electroluminescent devices including the compounds of Formula II-a, Formula II-b, or Formula II-c as emissive materials have deep blue color. In some embodiments, the blue emission has an x-coordinate less than 0.15 and a y-coordinate less than 0.10, according to the C.I.E. chromaticity scale; in some embodiments, the y-coordinate is less than 0.090.

In some embodiments, the new compounds having Formula II-a, Formula II-b, or Formula II-c can be used as hosts for electroluminescent materials.

In some embodiments, the new compounds having Formula II-a, Formula II-b, or Formula II-c can be used as electron transport materials in devices.

4. Compound Having Formula III-a, Formula III-b, or Formula III-c

In some embodiments, the compound having Formula III-a, Formula III-b, or Formula III-c is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula III-a, Formula III-b, and Formula III-c there are no amino groups.

In some embodiments of Formula III-a, Formula III-b, and Formula III-c, there are at least two amino groups. The amino groups can be attached directly to the core group as $R^1$, $R^2$, or $R^3$, or the amino groups can be substituents on $R^1$, $R^2$, or $R^3$.

In some embodiments, the electroactive compound has Formula III-a

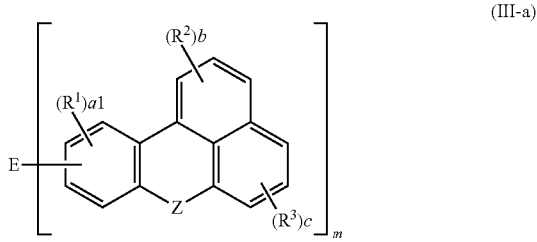

(III-a)

wherein:
E is selected from the group consisting of aryl, heteroaryl, and deuterated analogs thereof;
Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;
$R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;
$R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
$R^{4a}$ is selected from the group consisting of alkyl, silyl, germyl, aryl, and deuterated analogs thereof;
a1, b, and c are the same or different and are an integer from 0-3; and
m is 2 or 3.

In some embodiments of Formula III-a, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic.

In some embodiments of Formula III-a, at least one $R^2$ is present at position 7, as defined above, and at least one $R^3$ is present at position 8, as defined above.

In some embodiments of Formula III-a, $R^2$ at position 7 and $R^3$ at position 8 are joined together to form a fused ring group. In some embodiments, the fused ring group comprises a single fused ring. In some embodiments, the fused ring group comprises more than one fused ring.

In some embodiments, the fused ring group is a hydrocarbon aromatic. In some embodiments, the fused ring group is a heteroaromatic. In some embodiments, the fused ring group is non-aromatic.

In some embodiments, the fused ring group has 5-15 ring carbons; in some embodiments, 6-10 ring carbons.

In some embodiments, the fused ring group is unsubstituted.

In some embodiments, the fused ring group is substituted. In some embodiments, the substituents are selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula III-a, E is bonded to position 1 on the fused ring core, as defined above.

In some embodiments of Formula III-a, E is bonded to position 2 on the fused ring core, as defined above.

In some embodiments of Formula III-a, E is bonded to position 3 on the fused ring core, as defined above.

In some embodiments of Formula III-a, E is bonded to position 4 on the fused ring core, as defined above.

In some embodiments of Formula III-a, E is a hydrocarbon aryl group having 6-36 ring carbons. The hydrocarbon aryl group can include one or more single ring groups bonded together, one or more fused rings, or combinations thereof.

In some embodiments of Formula III-a, E is a hydrocarbon aryl having no fused rings.

In some embodiments of Formula III-a, E is a derivative of a compound selected from the group consisting of benzene, biphenyl, terphenyl, substituted derivatives thereof, and deuterated analogs thereof.

In some embodiments of Formula III-a, E is a hydrocarbon aryl having one or more fused rings.

In some embodiments of Formula III-a, E is a derivative of a compound selected from the group consisting of naphthalene, anthracene, phenanthrene, pyrene, chrysene, coronene, fluorene, benzofluorene, substituted derivatives thereof, and deuterated analogs thereof.

In some embodiments of Formula III-a, E is a heteroaryl or deuterated heteroaryl having 3-36 ring carbons. The heteroaryl group can include one or more single ring groups bonded together, one or more fused rings, or combinations thereof. There heteroaryl group can include hydrocarbon aryl rings.

In some embodiments of Formula III-a, E is an N-heteroaryl or deuterated N-heteroaryl having at least one ring atom which is N.

In some embodiments, the N-heteroaryl is derived from a compound selected from the group consisting of pyrrole, pyridine, pyrimidine, carbazole, imidazole, benzimidazole, imidazolobenzimidazole, triazole, benzotriazole, triazolopyridine, indole, indoloindole, indolocarbazole, phenanthroline, quinoline, isoquinoline, quinoxaline, substituted derivatives thereof, and deuterated analogs thereof.

In some embodiments of Formula III-a, E is an S-heteroaryl having at least one ring atom which is S.

In some embodiments, the S-heteroaryl is derived from a compound selected form the group consisting of thiophene, benzothiophene, dibenzothiophene, substituted derivatives thereof, and deuterated analogs thereof.

In some embodiments of Formula III-a, E is an O-heteroaryl having at least one ring atom that is O.

In some embodiments, the O-heteroaryl is derived from a compound selected from the group consisting of furan, benzofuran, dibenzofuran, substituted derivatives thereof, and deuterated analogs thereof.

In some embodiments of Formula III-a, E is an N,O-heteroaryl having at least one ring atom that is N and at least one ring atom that is O.

In some embodiments, the N,O-heteroaryl is derived from a compound selected from the group consisting of oxazole, benzoxazole, oxazine, phenoxazine, substituted derivaties thereof, and deuterated analogs thereof.

In some embodiments of Formula III-a, E is an N,S-heteroaryl having at least one ring atom that is N and at least one ring atom that is S.

In some embodiments, the N,S-heteroaryl is derived from a compound selected from the group consisting of thiazole, benzothiazole, substituted derivatives thereof, and deuterated analogs thereof.

In some embodiments of Formula E is a derivative of a compound selected from the group consisting of benzene, naphthalene, anthracene, fluorene, carbazole, dibenzothiophene, dibenzofuran, substituted derivatives thereof, and deuterated analogs thereof.

In some embodiments of Formula III-a, E has one or more substituents selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula III-a, m=2.

In some embodiments of Formula III-a, m=3.

The embodiments for Z, $R^2$, $R^3$, $R^4$, $R^{4a}$, $R^5$, b, and c described above for Formula I, apply equally to Formula III-a.

The embodiments for $R^1$ and a1 described above for Formula I-a, apply equally to Formula III-a.

In some embodiments, the electroactive compound has Formula III-b

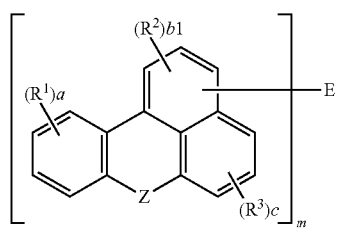

(III-b)

wherein:
- E is selected from the group consisting of aryl, heteroaryl, and deuterated analogs thereof;
- Z is selected from the group consisting of $CR^4R^5$, $C=CR^4R^5$, $SiR^4R^5$, $GeR^4R^5$, $NR^{4a}$; $PR^{4a}$, $P(O)R^{4a}$, O, S, SO, $SO_2$, Se; SeO, $SeO_2$, Te, TeO, and $TeO_2$;
- $R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;
- $R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
- $R^{4a}$ is selected from the group consisting of alkyl, silyl, germyl, aryl, and deuterated analogs thereof;
- a is an integer from 0-4;
- b1 is an integer from 0-2;
- c is an integer from 0-3; and
- m is 2 or 3.

In some embodiments of Formula III-b, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic.

In some embodiments of Formula III-b, at least one $R^2$ is present at position 7, as defined above, and at least one $R^3$ is present at position 8, as defined above.

In some embodiments of Formula III-b, $R^2$ at position 7 and $R^3$ at position 8 are joined together to form a fused ring group. In some embodiments, the fused ring group comprises a single fused ring. In some embodiments, the fused ring group comprises more than one fused ring.

In some embodiments, the fused ring group is a hydrocarbon aromatic. In some embodiments, the fused ring group is a heteroaromatic. In some embodiments, the fused ring group is non-aromatic.

In some embodiments, the fused ring group has 5-15 ring carbons; in some embodiments, 6-10 ring carbons.

In some embodiments, the fused ring group is unsubstituted.

In some embodiments, the fused ring group is substituted. In some embodiments, the substituents are selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula III-b, E is bonded to position 5 on the fused ring core, as defined above.

In some embodiments of Formula III-b, E is bonded to position 6 on the fused ring core, as defined above.

In some embodiments of Formula III-b, E is bonded to position 7 on the fused ring core, as defined above.

The embodiments for E described above for Formula III-a apply equally to Formula III-b.

The embodiments for Z, $R^1$, $R^3$, $R^4$, $R^{4a}$, $R^5$, a, and c described above for Formula I, apply equally to Formula III-a.

The embodiments for $R^2$ and b1 described above for Formula I-a, apply equally to Formula III-a.

In some embodiments, the electroactive compound has Formula III-c

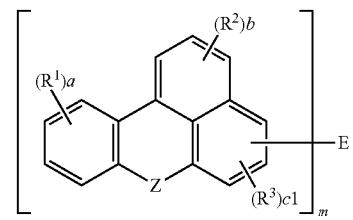

(III-c)

wherein:
- E is selected from the group consisting of aryl, heteroaryl, and deuterated analogs thereof;
- Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;
- $R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;
- $R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;

R$^{4a}$ is selected from the group consisting of alkyl, silyl, germyl, aryl, and deuterated analogs thereof;

a is an integer from 0-4;

b is an integer from 0-3;

c1 is an integer from 0-2; and m is 2 or 3.

In some embodiments of Formula III-c, adjacent R$^1$ or adjacent R$^2$ or adjacent R$^3$ groups can be joined together to form a fused ring. In some embodiments, the fused ring is aromatic. In some embodiments, the fused ring is a hydrocarbon aromatic. In some embodiments, the fused ring is a heteroaromatic.

In some embodiments of Formula III-c, at least one R$^2$ is present at position 7, as defined above, and at least one R$^3$ is present at position 8, as defined above.

In some embodiments of Formula III-c, R$^2$ at position 7 and R$^3$ at position 8 are joined together to form a fused ring group. In some embodiments, the fused ring group comprises a single fused ring. In some embodiments, the fused ring group comprises more than one fused ring.

In some embodiments, the fused ring group is a hydrocarbon aromatic. In some embodiments, the fused ring group is a heteroaromatic, In some embodiments, the fused ring group is non-aromatic.

In some embodiments, the fused ring group has 5-15 ring carbons; in some embodiments, 6-10 ring carbons.

In some embodiments, the fused ring group is unsubstituted.

In some embodiments, the fused ring group is substituted, In some embodiments, the substituents are selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula III-c, E is bonded to position 8 on the fused ring core, as defined above.

In some embodiments of Formula III-c, E is bonded to position 9 on the fused ring core, as defined above.

In some embodiments of Formula III-c, E is bonded to position 10 on the fused ring core, as defined above.

The embodiments for E and m described above for Formula III-a apply equally to Formula III-c.

The embodiments for Z, R$^1$, R$^2$, R$^4$, R$^{4a}$, R$^5$, a, and b described above for Formula I, apply equally to Formula III-a.

The embodiments for R$^3$ and c1 described above for Formula II-b, apply equally to Formula III-a.

Any of the above embodiments for Formula III-a, Formula III-b, or Formula III-c can be combined with one or more of the other embodiments, so long as they are not mutually exclusive. For example, the embodiment in which E=phenyl can be combined with the embodiment in which R$^4$=R$^5$. The same is true for the other non-mutually-exclusive embodiments discussed above. The skilled person would understand which embodiments were mutually exclusive and would thus readily be able to determine the combinations of embodiments that are contemplated by the present application.

The compounds of Formula III-a, Formula III-b, or Formula III-c can be made using any technique that will yield a C—C or C—N bond. A variety of such techniques are known, such as Suzuki, Yamamoto, Stille, and Pd- or Ni-catalyzed C—N couplings. Synthetic methods similar to those used in the preparation of compounds of Formula I above may be used to produce compounds of Formula III-a, Formula III-b, and Formula III-c.

Deuterated compounds can be prepared in a similar manner using deuterated precursor materials or, more generally, by treating the non-deuterated compound with deuterated solvent, such as d6-benzene, in the presence of a Lewis acid HID exchange catalyst, such as aluminum trichloride or ethyl aluminum dichloride.

Exemplary preparations are given in the Examples.

Some non-limiting examples of compounds having Formula III-a, Formula III-b, or Formula III-c are shown below.

Compound III-1

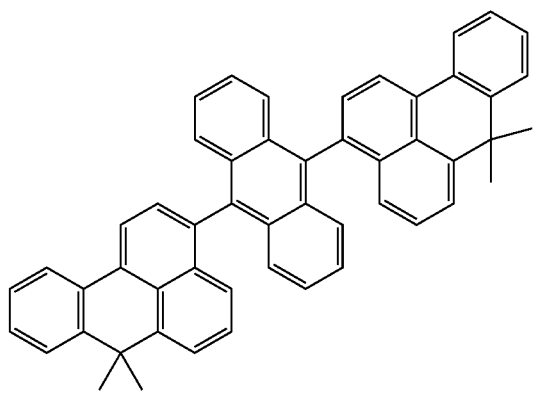

Compound III-2

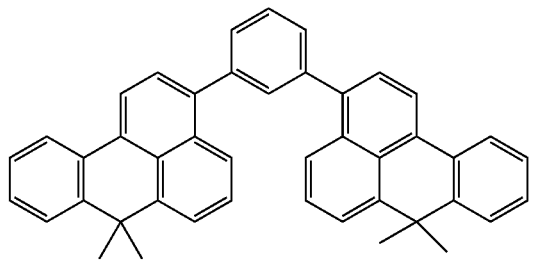

Compound III-3

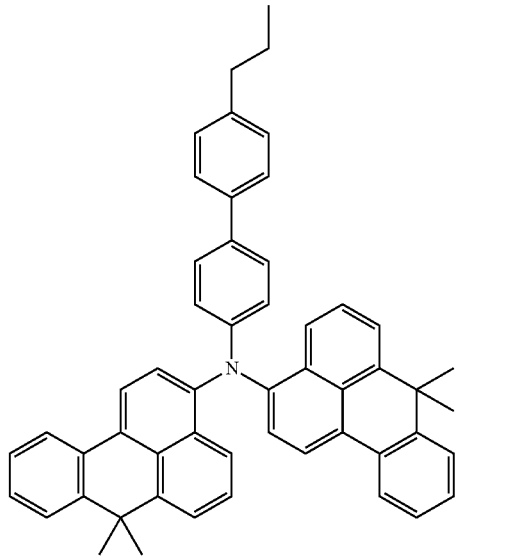

-continued
Compound III-4
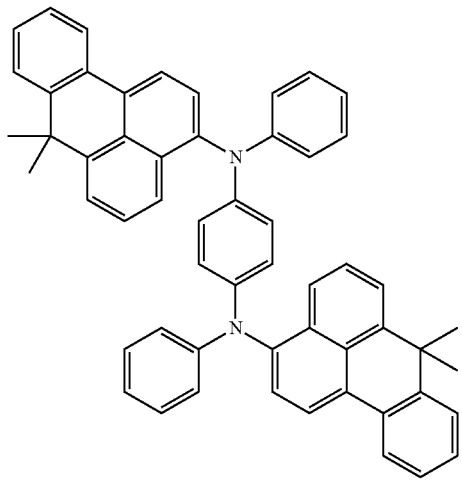
Compound III-5
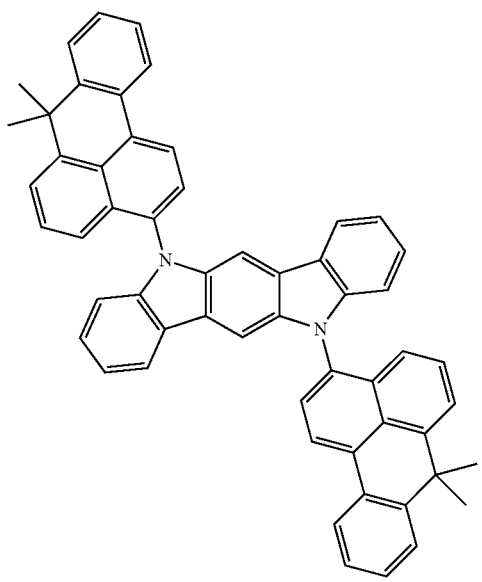
Compound III-6
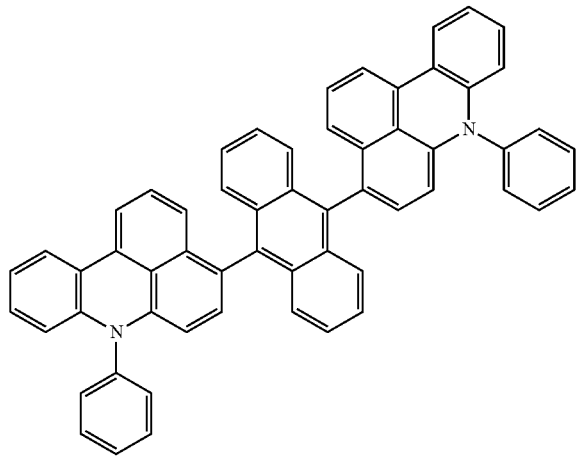
Compound III-7
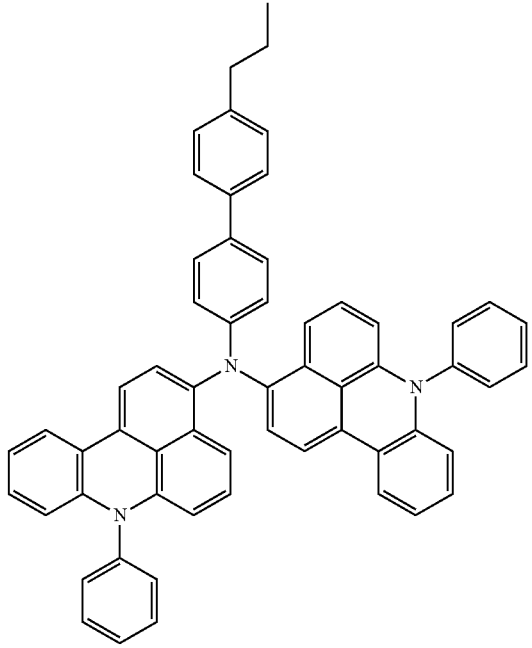
Compound III-8
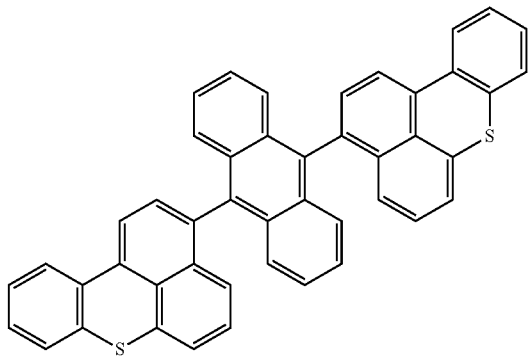
Compound III-9
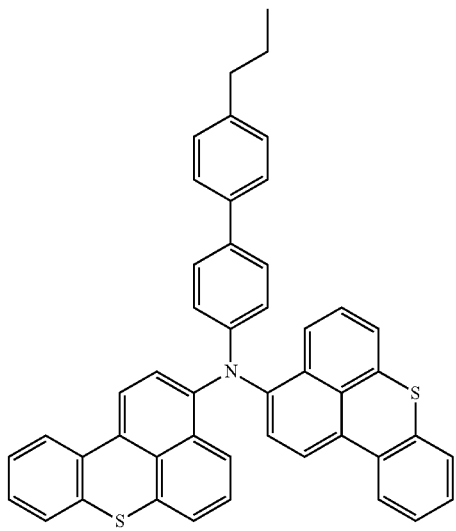

-continued

Compound III-10

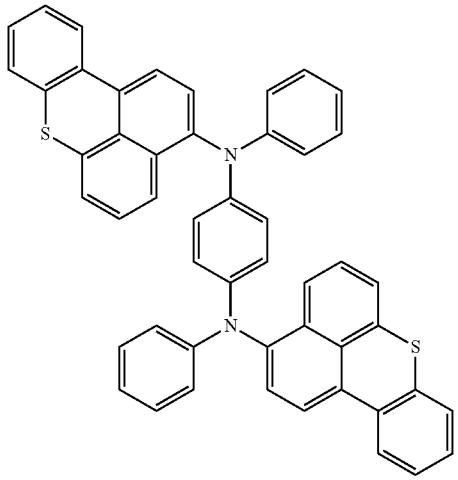

The compounds can be formed into layers for electronic devices, as described above.

In some embodiments, the new compounds having Formula III-a, Formula III-b, or Formula III-c can be used as hole transport materials in devices.

In some embodiments, the new compounds having Formula III-a, Formula III-b, or Formula III-c are electroluminescent and can be used as emissive materials in devices. In some embodiments, the compounds are blue light-emitting.

In some embodiments, the compounds having Formula III-a, Formula III-b, or Formula III-c have a photoluminescence y-coordinate of less than 0.15, according to the C.I.E. chromaticity scale; in some embodiments, less than 0.10; in some embodiments, less than 0.090.

In some embodiments, electroluminescent devices including the compounds of Formula III-a, Formula III-b, or Formula III-c as emissive materials have deep blue color. In some embodiments, the blue emission has an x-coordinate less than 0.15 and a y-coordinate less than 0.10, according to the C.I.E. chromaticity scale; in some embodiments, the y-coordinate is less than 0.090.

In some embodiments, the new compounds having Formula III-a, Formula III-b, or Formula III-c can be used as hosts for electroluminescent materials.

In some embodiments, the new compounds having Formula III-a, Formula III-b, or Formula III-c can be used as electron transport materials in devices.

5. Compound Having Formula IV-a, Formula IV-b, or Formula IV-c

In some embodiments, the compound having Formula IV-a, Formula IV-b, or Formula IV-c is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula IV-a, Formula IV-b, and Formula IV-c there are no amino groups.

In some embodiments of Formula IV-a, Formula IV-b, and Formula IV-c, there are at least two amino groups. The amino groups can be attached directly to the core group as $R^1$, $R^2$, or $R^3$, or the amino groups can be substituents on $R^1$, $R^2$, or $R^3$.

In some embodiments, the electroactive compound has Formula IV-a

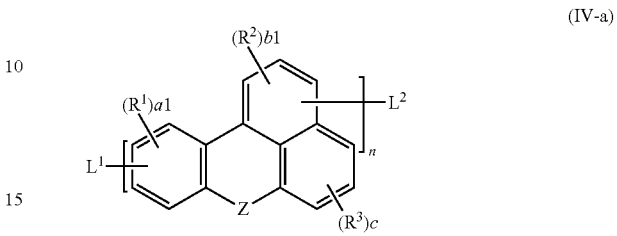

(IV-a)

wherein;
Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;
$L^1$ and $L^2$ are the same or different and are selected from the group consisting of H, D, halogen, aryl, arylamino, crosslinkable groups, deuterated aryl, deuterated arylamino, and deuterated crosslinkable groups;
$R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;
$R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
$R^{4a}$ is selected from the group consisting of alkyl, silyl, germyl, aryl, and deuterated analogs thereof;
alkyl, deuterated amino, and deuterated silyl;
a1 and c are the same or different and are an integer from 0-3;
b1 is an integer from 0-2; and
n is an integer greater than 0.

In some embodiments of Formula IV-a, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic.

In some embodiments of Formula IV-a, at least one $R^2$ is present at position 7, as defined above, and at least one $R^3$ is present at position 8, as defined above.

In some embodiments of Formula IV-a, $R^2$ at position 7 and $R^3$ at position 8 are joined together to form a fused ring group. In some embodiments, the fused ring group comprises a single fused ring. In some embodiments, the fused ring group comprises more than one fused ring.

In some embodiments, the fused ring group is a hydrocarbon aromatic. In some embodiments, the fused ring group is a heteroaromatic. In some embodiments, the fused ring group is non-aromatic.

In some embodiments, the fused ring group has 5-15 ring carbons; in some embodiments, 6-10 ring carbons.

In some embodiments, the fused ring group is unsubstituted.

In some embodiments, the fused ring group is substituted. In some embodiments, the substituents are selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

The compound having Formula IV-a can be a small molecule with n=1, an oligomer, or a polymer. As used herein, the term "compound having Formula IV-a" is intended to include small molecules, oligomers and polymers.

In some embodiments of Formula IV-a, n=1 and $L^1$ is halogen. Such compounds can be useful as monomers for the formation of polymeric compounds.

In some embodiments, the halogen is Cl or Br; in some embodiments, Br.

In some embodiments of Formula IV-a, n=1 and $L^2$ is halogen.

In some embodiments of Formula IV-a, n=1 and $L^1$ is a crosslinking group or deuterated crosslinking group.

In some embodiments of Formula IV-a, n=1 and $L^2$ is a crosslinking group or deuterated crosslinking group.

In some embodiments of Formula IV-a, n=1 and $L^1$ is H or D.

In some embodiments of Formula IV-a, n=1 and $L^2$ is H or D.

In some embodiments of Formula IV-a, n=2-10.

In some embodiments of Formula IV-a, the compound is a polymer with n>10. In some embodiments, the compound is a polymer with $M_n$>20,000; in some embodiments, $M_n$>50,000.

In some embodiments of Formula IV-a, n>10 and $L^1$ is selected from aryl, arylamino, crosslinkable groups, and deuterated analogs thereof.

In some embodiments of Formula IV-a, n>10 and $L^2$ is selected from aryl, arylamino, crosslinkable groups, and deuterated analogs thereof.

In some embodiments of Formula IV-a, n>10 and $L^1$ is selected from phenyl, biphenyl, diphenylamino, and deuterated analogs thereof.

In some embodiments of Formula IV-a, n>10 and $L^2$ is selected from phenyl, biphenyl, diphenylamino, and deuterated analogs thereof.

In some embodiments of Formula IV-a, $L^1$ is bonded to position 1 on the fused ring core, as defined above.

In some embodiments of Formula IV-a, $L^1$ is bonded to position 2 on the fused ring core, as defined above.

In some embodiments of Formula IV-a, $L^1$ is bonded to position 3 on the fused ring core, as defined above.

In some embodiments of Formula IV-a, $L^1$ is bonded to position 4 on the fused ring core, as defined above.

In some embodiments of Formula IV-a, $L^2$ is bonded to position 5 on the fused ring core, as defined above.

In some embodiments of Formula IV-a, $L^2$ is bonded to position 6 on the fused ring core, as defined above.

In some embodiments of Formula IV-a, $L^2$ is bonded to position 7 on the fused ring core, as defined above.

The embodiments for Z, $R^1$, $R^2$, $R^3$, $R^4$, $R^{4a}$, $R^5$, a1, b1, and c described above for Formula I-a, apply equally to Formula IV-a.

In some embodiments, the electroactive compound has Formula IV-b

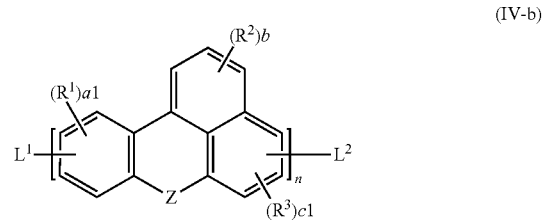

(IV-b)

wherein;
Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;

$L^1$ and $L^2$ are the same or different and are selected from the group consisting of H, D, halogen, aryl, arylamino, crosslinkable groups, deuterated aryl, deuterated arylamino, and deuterated crosslinkable groups;

$R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;

$R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;

$R^{4a}$ is selected from the group consisting of alkyl, silyl, germyl, aryl, and deuterated analogs thereof;

a1 and b are the same or different and are an integer from 0-3;

c1 is an integer from 0-2; and n is an integer greater than 0.

In some embodiments of Formula IV-b, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic.

In some embodiments of Formula IV-b, at least one $R^2$ is present at position 7, as defined above, and at least one $R^3$ is present at position 8, as defined above.

In some embodiments of Formula IV-b, $R^2$ at position 7 and $R^3$ at position 8 are joined together to form a fused ring group. In some embodiments, the fused ring group comprises a single fused ring. In some embodiments, the fused ring group comprises more than one fused ring.

In some embodiments, the fused ring group is a hydrocarbon aromatic. In some embodiments, the fused ring group is a heteroaromatic. In some embodiments, the fused ring group is non-aromatic.

In some embodiments, the fused ring group has 5-15 ring carbons; in some embodiments, 6-10 ring carbons.

In some embodiments, the fused ring group is unsubstituted.

In some embodiments, the fused ring group is substituted. In some embodiments, the substituents are selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

The compound having Formula IV-b can be a small molecule with n=1, an oligomer, or a polymer. As used herein, the term "compound having Formula IV-b" is intended to include small molecules, oligomers and polymers.

In some embodiments of Formula IV-b, $L^1$ is bonded to position 1 on the fused ring core, as defined above.

In some embodiments of Formula IV-b, $L^1$ is bonded to position 2 on the fused ring core, as defined above.

In some embodiments of Formula IV-b, $L^1$ is bonded to position 3 on the fused ring core, as defined above.

In some embodiments of Formula IV-b, $L^1$ is bonded to position 4 on the fused ring core, as defined above.

In some embodiments of Formula IV-b, $L^2$ is bonded to position 8 on the fused ring core, as defined above.

In some embodiments of Formula IV-b, $L^2$ is bonded to position 9 on the fused ring core, as defined above.

In some embodiments of Formula IV-b, $L^2$ is bonded to position 10 on the fused ring core, as defined above.

The embodiments for Z, $R^1$, $R^2$, $R^3$, $R^4$, $R^{4a}$, $R^5$, a1, b, and c1 described above for Formula II-b, apply equally to Formula IV-b.

The embodiments for $L^1$, $L^2$, and n described above for Formula IV-a, apply equally to Formula IV-b.

In some embodiments, the electroactive compound has Formula IV-c

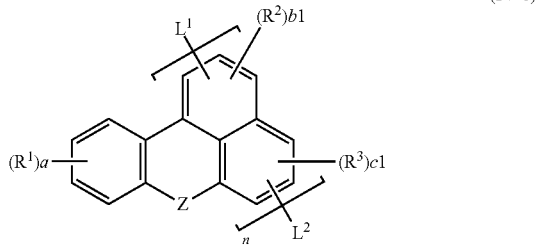

(IV-c)

wherein:
Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;
$L^1$ and $L^2$ are the same or different and are selected from the group consisting of H, D, halogen, aryl, arylamino, crosslinkable groups, deuterated aryl, deuterated arylamino, and deuterated crosslinkable groups;
$R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;
$R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
$R^{4a}$ is selected from the group consisting of alkyl, silyl, germyl, aryl, and deuterated analogs thereof;
a is an integer from 0-4;
b1 and c1 are the same or different and are an integer from 0-2; and
n is an integer greater than 0.

In some embodiments of Formula IV-c, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic.

In some embodiments of Formula IV-c, at least one $R^2$ is present at position 7, as defined above, and at least one $R^3$ is present at position 8, as defined above.

In some embodiments of Formula IV-c, $R^2$ at position 7 and $R^3$ at position 8 are joined together to form a fused ring group. In some embodiments, the fused ring group comprises a single fused ring. In some embodiments, the fused ring group comprises more than one fused ring.

In some embodiments, the fused ring group is a hydrocarbon aromatic. In some embodiments, the fused ring group is a heteroaromatic. In some embodiments, the fused ring group is non-aromatic.

In some embodiments, the fused ring group has 5-15 ring carbons; in some embodiments, 6-10 ring carbons.

In some embodiments, the fused ring group is unsubstituted.

In some embodiments, the fused ring group is substituted. In some embodiments, the substituents are selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

The compound having Formula IV-c can be a small molecule with n=1, an oligomer, or a polymer. As used herein, the term "compound having Formula IV-c" is intended to include small molecules, oligomers and polymers.

In some embodiments of Formula IV-c, $L^1$ is bonded to position 5 on the fused ring core, as defined above.

In some embodiments of Formula IV-c, $L^1$ is bonded to position 6 on the fused ring core, as defined above.

In some embodiments of Formula IV-c, $L^1$ is bonded to position 7 on the fused ring core, as defined above.

In some embodiments of Formula IV-c, $L^2$ is bonded to position 8 on the fused ring core, as defined above.

In some embodiments of Formula IV-c, $L^2$ is bonded to position 9 on the fused ring core, as defined above.

In some embodiments of Formula IV-c, $L^2$ is bonded to position 10 on the fused ring core, as defined above.

The embodiments for Z, $L^1$, $L^2$, $R^1$, $R^2$, $R^3$, $R^4$, $R^{4a}$, $R^5$, b1, and n described above for Formula IV-a, apply equally to Formula IV-c.

The embodiments for a and c1 described above for Formula III-c, apply equally to Formula IV-c.

Any of the above embodiments for Formula IV-a, Formula IV-b, or Formula IV-c can be combined with one or more of the other embodiments, so long as they are not mutually exclusive. For example, the embodiment in which $L^1$=$L^2$ can be combined with the embodiment in which $L^2$ is selected from phenyl, biphenyl, diphenylamino, and deuterated analogs thereof. The same is true for the other non-mutually-exclusive embodiments discussed above. The skilled person would understand which embodiments were mutually exclusive and would thus readily be able to determine the combinations of embodiments that are contemplated by the present application.

The compounds of Formula IV-a, Formula IV-b, or Formula IV-c can be made using any technique that will yield a C—C or C—N bond and known polymerization techniques. A variety of such techniques are known, such as Suzuki, Yamamoto, Stille, and Pd- or Ni-catalyzed C—N couplings, Synthetic methods similar to those used in the preparation of compounds of Formula I above may be used to produce compounds of Formula IV-a and Formula IV-b.

Deuterated compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum dichloride.

Exemplary preparations are given in the Examples.

Some non-limiting examples of compounds having Formula IV-a, Formula IV-b, or Formula IV-c are shown below.

In some embodiments, the new compounds having Formula IV-a, Formula IV-b, or Formula IV-c are electroluminescent and can be used as emissive materials in devices. In some embodiments, the compounds are blue light-emitting.

In some embodiments, the compounds having Formula IV-a, Formula IV-b, or Formula IV-c have a photoluminescence y-coordinate of less than 0.15, according to the C.I.E. chromaticity scale; in some embodiments, less than 0.10; in some embodiments, less than 0.090.

Compound III-1

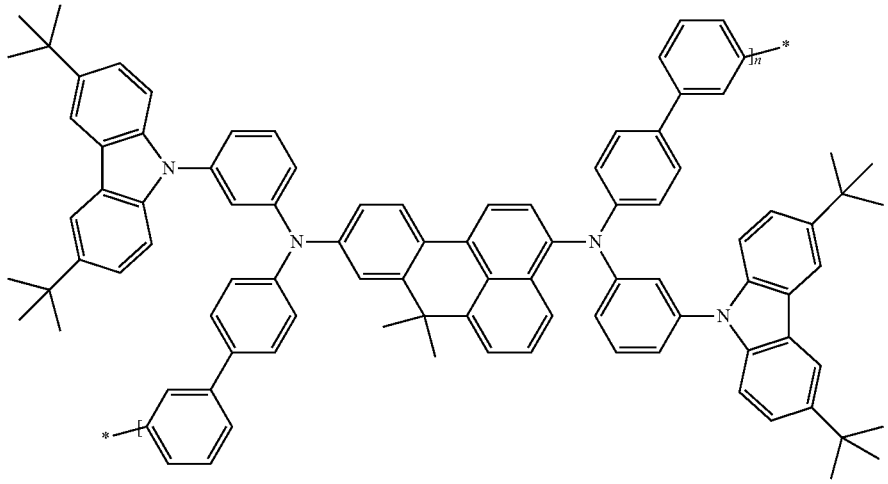

Compound III-2

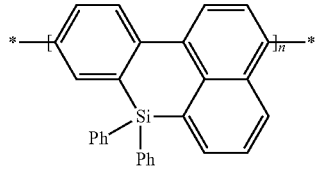

Ph = phenyl

Compound III-3

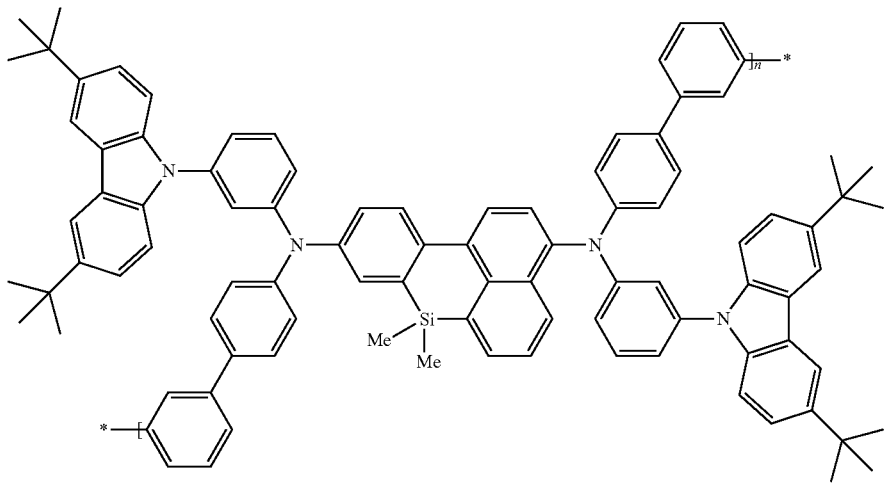

Me = methyl

In Compounds III-1 to III-3, n>5.

The compounds can be formed into layers for electronic devices, as described above.

In some embodiments, the new compounds having Formula IV-a, Formula IV-b, or Formula IV-c can be used as hole transport materials in devices.

In some embodiments, electroluminescent devices including the compounds of Formula IV-a, Formula IV-b, or Formula IV-c as emissive materials have deep blue color. In some embodiments, the blue emission has an x-coordinate less than 0.15 and a y-coordinate less than 0.10, according to the C.I.E. chromaticity scale; in some embodiments, the y-coordinate is less than 0.090.

In some embodiments, the new compounds having Formula IV-a, Formula IV-b, or Formula IV-c can be used as hosts for electroluminescent materials.

In some embodiments, the new compounds having Formula IV-a, Formula IV-b, or Formula IV-c can be used as electron transport materials in devices.

6. Copolymer Having Monomeric Unit of Formula V-a, Formula V-b, or Formula V-c

In some embodiments, the monomeric unit having Formula V-a, Formula V-b, or Formula V-c is deuterated. In some embodiments, the monomeric unit is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula V-a, Formula V-b, and Formula V-c there are no amino groups.

In some embodiments of Formula V-a, Formula V-b, and Formula V-c, there are at least two amino groups. The amino groups can be attached directly to the core group as $R^1$, $R^2$, or $R^3$, or the amino groups can be substituents on $R^1$, $R^2$, or $R^3$.

In some embodiments, the electroactive compound is a copolymer having at least one monomeric unit of Formula V-a

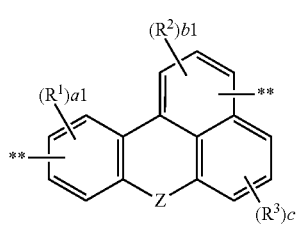
(V-a)

wherein:
- Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;
- $R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;
- $R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
- $R^{4a}$ is selected from the group consisting of alkyl, silyl, germyl, aryl, and deuterated analogs thereof;
- a1 and c are the same or different and are an integer from 0-3;
- b1 is an integer from 0-2; and
- ** indicates the point of attachment in the copolymer.

In some embodiments of Formula V-a, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic.

In some embodiments of Formula V-a, at least one $R^2$ is present at position 7, as defined above, and at least one $R^3$ is present at position 8, as defined above.

In some embodiments of Formula V-a, $R^2$ at position 7 and $R^3$ at position 8 are joined together to form a fused ring group. In some embodiments, the fused ring group comprises a single fused ring. In some embodiments, the fused ring group comprises more than one fused ring.

In some embodiments, the fused ring group is a hydrocarbon aromatic. In some embodiments, the fused ring group is a heteroaromatic. In some embodiments, the fused ring group is non-aromatic.

In some embodiments, the fused ring group has 5-15 ring carbons; in some embodiments, 6-10 ring carbons.

In some embodiments, the fused ring group is unsubstituted.

In some embodiments, the fused ring group is substituted. In some embodiments, the substituents are selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula V-a, one point of attachment is at position 1 on the fused ring core, as defined above.

In some embodiments of Formula V-a, one point of attachment is at position 2 on the fused ring core, as defined above.

In some embodiments of Formula V-a, one point of attachment is at position 3 on the fused ring core, as defined above.

In some embodiments of Formula V-a, one point of attachment is at position 4 on the fused ring core, as defined above.

In some embodiments of Formula V-a, one point of attachment is at position 5 on the fused ring core, as defined above.

In some embodiments of Formula V-a, one point of attachment is at position 6 on the fused ring core, as defined above.

In some embodiments of Formula V-a, one point of attachment is at position 7 on the fused ring core, as defined above.

The embodiments for Z, $R^1$, $R^2$, $R^3$, $R^4$, $R^{4a}$, a1, b1, and c described above for Formula II-a, apply equally to Formula V-a.

In some embodiments, the electroactive compound is a copolymer having at least one monomeric unit of Formula V-b

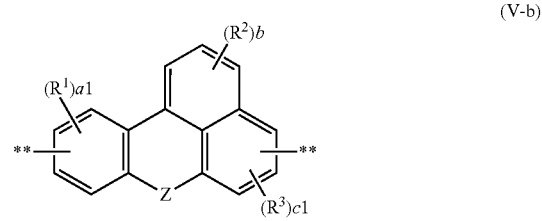
(V-b)

wherein:
Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;
$R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;
$R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
$R^{4a}$ is selected from the group consisting of alkyl, silyl, germyl, aryl, and deuterated analogs thereof;
a1 and b are the same or different and are an integer from 0-3;
c1 is an integer from 0-2; and
** indicates the point of attachment in the copolymer.

In some embodiments of Formula V-b, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic.

In some embodiments of Formula V-b, at least one $R^2$ is present at position 7, as defined above, and at least one $R^3$ is present at position 8, as defined above.

In some embodiments of Formula V-b, $R^2$ at position 7 and $R^3$ at position 8 are joined together to form a fused ring group. In some embodiments, the fused ring group comprises a single fused ring. In some embodiments, the fused ring group comprises more than one fused ring.

In some embodiments, the fused ring group is a hydrocarbon aromatic. In some embodiments, the fused ring group is a heteroaromatic. In some embodiments, the fused ring group is non-aromatic.

In some embodiments, the fused ring group has 5-15 ring carbons; in some embodiments, 6-10 ring carbons.

In some embodiments, the fused ring group is unsubstituted.

In some embodiments, the fused ring group is substituted. In some embodiments, the substituents are selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula V-b, one point of attachment is at position 1 on the fused ring core, as defined above.

In some embodiments of Formula V-b, one point of attachment is at position 2 on the fused ring core, as defined above.

In some embodiments of Formula V-b, one point of attachment is at position 3 on the fused ring core, as defined above.

In some embodiments of Formula V-b, one point of attachment is at position 4 on the fused ring core, as defined above.

In some embodiments of Formula V-b, one point of attachment is at position 8 on the fused ring core, as defined above.

In some embodiments of Formula V-b, one point of attachment is at position 9 on the fused ring core, as defined above.

In some embodiments of Formula V-b, one point of attachment is at position 10 on the fused ring core, as defined above.

The embodiments for Z, $R^1$, $R^2$, $R^3$, $R^4$, $R^{4a}$, $R^5$, a1, b, and c1 described above for Formula II-b, apply equally to Formula V-b.

In some embodiments, the electroactive compound is a copolymer having at least one monomeric unit of Formula V-c

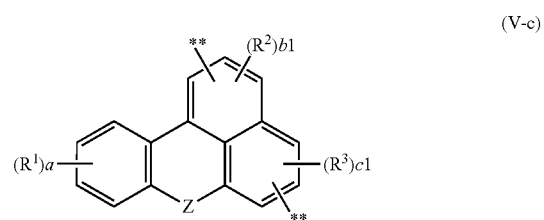

(V-c)

wherein:
Z is selected from the group consisting of $CR^4R^5$, $C=CR^4R^5$, $SiR^4R^5$, $GeR^4R^5$, $NR^{4a}$, $PR^{4a}$, $P(O)R^{4a}$, O, S, SO, $SO_2$, Se; SeO, $SeO_2$, Te, TeO, and $TeO_2$;
$R^1$-$R^3$ are the same or different at each occurrence and are selected from the group consisting of D, aryl, heteroaryl, alkyl, amino, silyl, germyl, deuterated aryl, deuterated heteroaryl, deuterated alkyl, deuterated amino, deuterated silyl, and deuterated germyl, where two groups selected from $R^1$, $R^2$, and $R^3$ can be joined together to form a fused ring;
$R^4$-$R^5$ are the same or different at each occurrence and are selected from the group consisting of H, D, aryl, heteroaryl, alkyl, amino, silyl, germyl, deuterated aryl, deuterated heteroaryl, deuterated alkyl, deuterated amino, deuterated silyl, and deuterated germyl;
$R^4a$ is selected from the group consisting of alkyl, silyl, germyl, aryl, and deuterated analogs thereof;
a in an integer from 0-4;
b1 and c1 are the same or different and are an integer from 0-2; and
** indicates the point of attachment in the copolymer.

In some embodiments of Formula V-c, adjacent $R^1$ or adjacent $R^2$ or adjacent $R^3$ groups can be joined together to form a fused ring. In some embodiments, the fused ring is aromatic. In some embodiments, the fused ring is a hydrocarbon aromatic. In some embodiments, the fused ring is a heteroaromatic.

In some embodiments of Formula V-c, at least one $R^2$ is present at position 7, as defined above, and at least one $R^3$ is present at position 8, as defined above.

In some embodiments of Formula V-c, $R^2$ at position 7 and $R^3$ at position 8 are joined together to form a fused ring group. In some embodiments, the fused ring group comprises a single fused ring. In some embodiments, the fused ring group comprises more than one fused ring.

In some embodiments, the fused ring group is a hydrocarbon aromatic. In some embodiments, the fused ring group is a heteroaromatic. In some embodiments, the fused ring group is non-aromatic.

In some embodiments, the fused ring group has 5-15 ring carbons; in some embodiments, 6-10 ring In some embodiments, the fused ring group is unsubstituted.

In some embodiments, the fused ring group is substituted. In some embodiments, the substituents are selected from the group consisting of D, F, CN, alkyl, alkoxy, silyl, siloxy, siloxane, aryl, heteroaryl, diarylamino, carbazolyl, deuterated alkyl, deuterated alkoxy, deuterated silyl, deuterated siloxy, deuterated siloxane, deuterated aryl, deuterated heteroaryl, deuterated diarylamino, deuterated carbazolyl, and combinations thereof.

In some embodiments of Formula V-c, one point of attachment is at position 1 on the fused ring core, as defined above.

In some embodiments of Formula V-c, one point of attachment is at position 6 on the fused ring core, as defined above.

In some embodiments of Formula V-c, one point of attachment is at position 7 on the fused ring core, as defined above.

In some embodiments of Formula V-c, one point of attachment is at position 8 on the fused ring core, as defined above.

In some embodiments of Formula V-c, one point of attachment is at position 9 on the fused ring core, as defined above.

In some embodiments of Formula V-c, one point of attachment is at position 10 on the fused ring core, as defined above.

The embodiments for Z, $R^1$, $R^2$, $R^3$, $R^4$, $R^{4a}$, $R^5$, a, b1, and c1 described above for Formula II-c, apply equally to Formula V-c.

The copolymers having at least one monomeric unit of Formula V-a, Formula V-b or Formula V-c can be made using any technique that will yield a C—C or C—N bond and known polymerization techniques. A variety of such techniques are known, such as Suzuki, Yamamoto, Stifle, and Pd- or Ni-catalyzed C—N couplings. Synthetic methods similar to those used in the preparation of compounds of Formula I above may be used to produce monomers having a unit of Formula V-a, Formula V-b, or Formula V-c.

In some embodiments, the copolymer has Formula VI

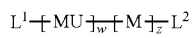

Formula VI wherein:
  $L^1$ and $L^2$ are the same or different and are selected from the group consisting of H, D, halogen, aryl, arylamino, crosslinkable groups, deuterated aryl, deuterated arylamino, and deuterated crosslinkable groups;
  M is a conjugated moiety;
  MU is a monomeric unit having Formula V-a, Formula V-b, or Formula V-c; and
  w and z represent non-zero mole fractions such that w+z=1.

In some embodiments of Formula VI, the "MU" and "M" units are ordered in a regular alternating pattern.

In some embodiments of Formula VI, the "MU" and "M" units are ordered in blocks of like monomers.

In some embodiments of Formula VI, the "MU" and "M" units are randomly arranged.

In some embodiments of Formula VI, $L^1$ is selected from aryl, arylamino, crosslinkable groups, and deuterated analogs thereof.

In some embodiments of Formula VI, $L^1$ is selected from phenyl, triphenylamino, and deuterated analogs thereof.

In some embodiments of Formula VI, $L^2$ is selected from aryl, arylamino, crosslinkable groups, and deuterated analogs thereof.

In some embodiments of Formula VI, $L^2$ is selected from phenyl, triphenylamino, and deuterated analogs thereof.

In some embodiments of Formula VI, M is a deuterated aromatic moiety.

In some embodiments of Formula VI, M is a monomeric unit derived from an olefin, an acetylenic compound, a styrene, a stilbene, a substituted derivative thereof, or a deuterated analog thereof.

In some embodiments of Formula VI, M has Formula c1

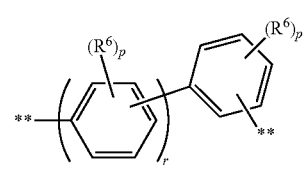

Formula c1 where "**" indicates the point of attachment in the copolymer and where $R^6$, p, and r are as in Formula a.

In some embodiments, M has Formula d1

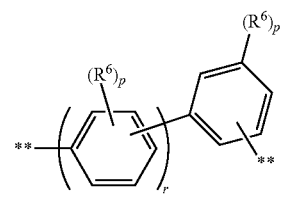

Formula d1 where $R^6$, p, r and ** are as in Formula b.

In some embodiments of Formula VI, M is a monomeric unit derived from a hydrocarbon aryl having two or more fused rings or a deuterated analog thereof.

In some embodiments of Formula VI, M is a monomeric unit derived from the group consisting of naphthalene, anthracene, fluorene, phenanthrene, triphenylene, substituted derivatives thereof, and deuterated analogs thereof.

In some embodiments of Formula VI, M is a monomeric unit derived from a triarylamino group or deuterated analog thereof.

In some embodiments of Formula VI, M is a monomeric unit derived from a heteroaromatic compound having at least one ring atom which is selected from the group consisting of N, O, and S.

In some embodiments of Formula VI, M is a monomeric unit derived from an N-heteroaryl.

In some embodiments, the N-heteroaryl is a carbazole or deuterated carbazole.

In some embodiments of Formula VI, M is a monomeric unit derived from an S-heteroaryl having at least one ring atom which is S.

In some embodiments of Formula VI, M is a monomeric unit derived from an O-heteroaryl having at least one ring atom that is O.

In some embodiments of Formula VI, M is a monomeric unit derived from an N,O-heteroaryl having at least one ring atom that is N and at least one ring atom that is O.

In some embodiments of Formula VI, M is a monomeric unit derived from an N,S-heteroaryl having at least one ring atom that is N and at least one ring atom that is S.
In some embodiments of Formula VI, M has one of the formulae given below.
M1
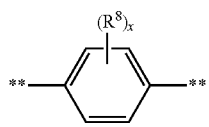
M2
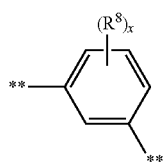
M3
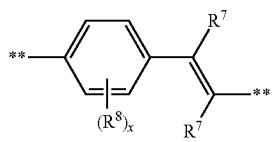
M4
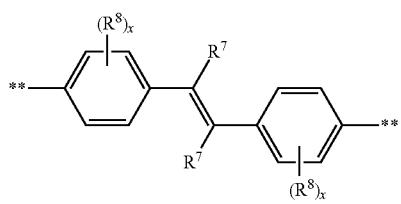
M5
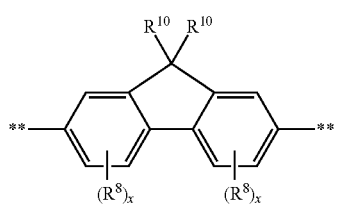
M6
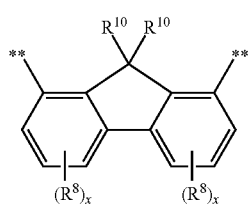
M7
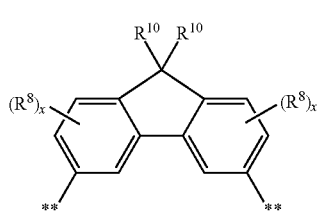
-continued
M8
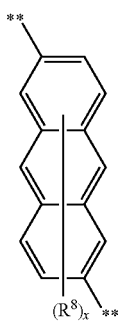
M9
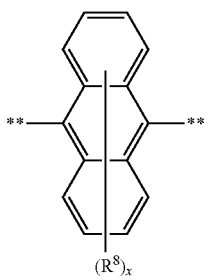
M10
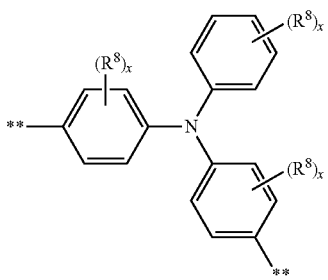
M11
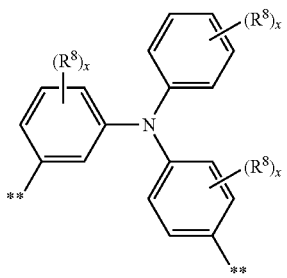
M12
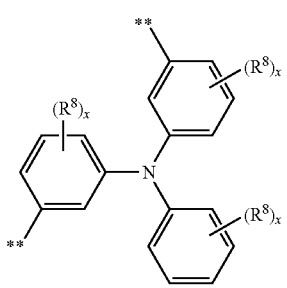

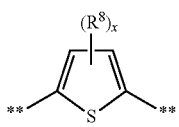

M13

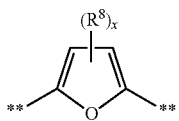

M14

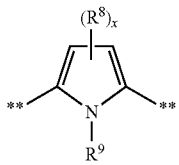

M15

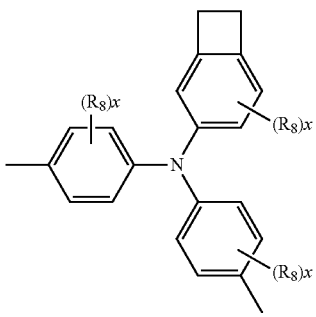

M16

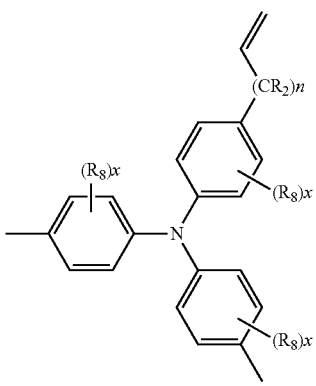

M17

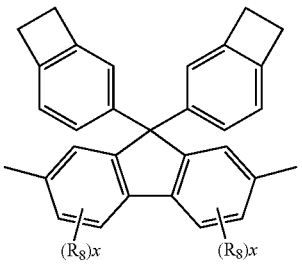

M18

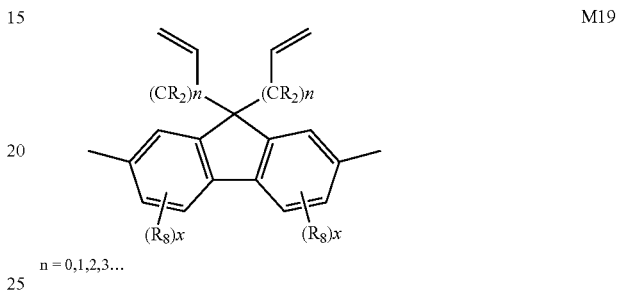

M19 n = 0,1,2,3...

In M1 through M19:

$R^7$ is the same or different at each occurrence and is selected from the group consisting of H, D, alkyl, and deuterated alkyl;

$R^8$ is the same or different at each occurrence and is selected from the group consisting of D, alkyl, silyl, aryl, deuterated alkyl, deuterated silyl, and deuterated aryl;

$R^9$ is the same or different at each occurrence and is selected from the group consisting of aryl and deuterated aryl;

$R^{10}$ is the same or different at each occurrence and is selected from the group consisting of alkyl, aryl, and deuterated analogs thereof;

x is the same or different at each occurrence and is an integer from 0 to the maximum number of positions available for substituents; and

** represents the point of attachment in the copolymer.

In some embodiments of M1 through M15, x is 0-2.

In some embodiments of Formula VI, w is in the range of 0.5-0.99; in some embodiments, 0.6-0.95; in some embodiments, 0.75-0.95.

Any of the above embodiments for Formula VI can be combined with one or more of the other embodiments, so long as they are not mutually exclusive. For example, the embodiment in which MU has Formula V-a can be combined with the embodiment in which M has formula M1. The same is true for the other non-mutually-exclusive embodiments discussed above. The skilled person would understand which embodiments were mutually exclusive and would thus readily be able to determine the combinations of embodiments that are contemplated by the present application.

The copolymer having Formula VI can be made using known coupling techniques and polymerization techniques.

Some non-limiting examples of copolymers having Formula VI are shown below.

Compound VI-1

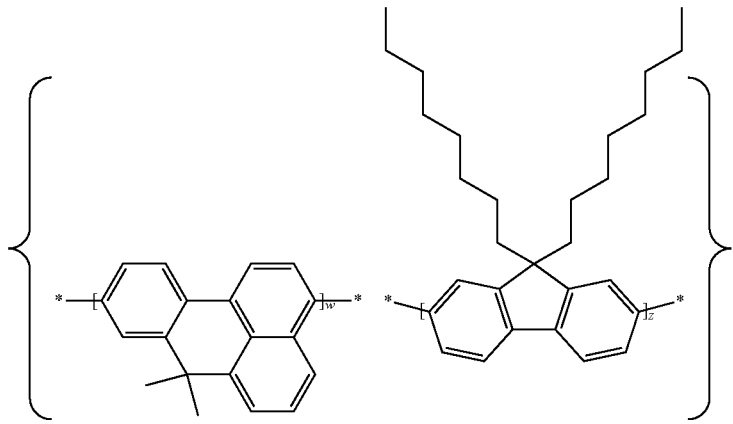

Compound VI-2

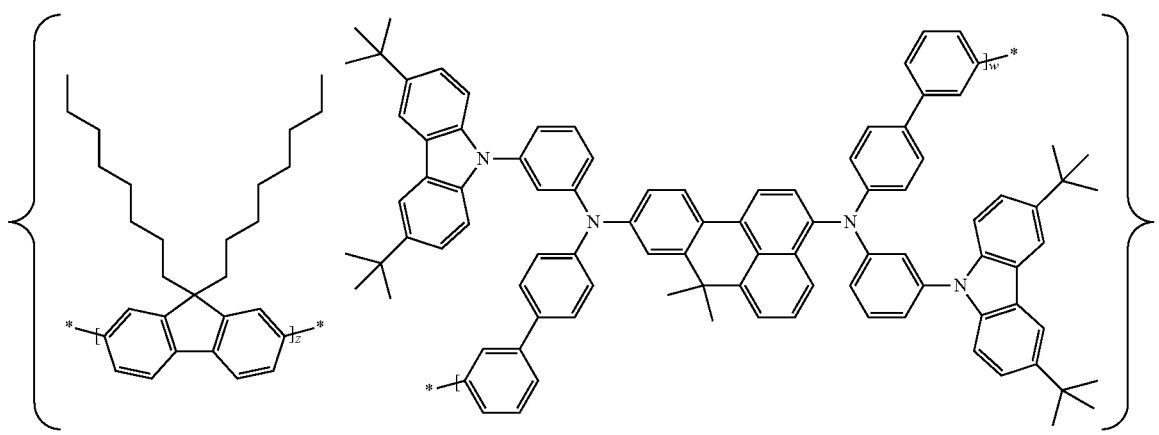

Compound VI-3

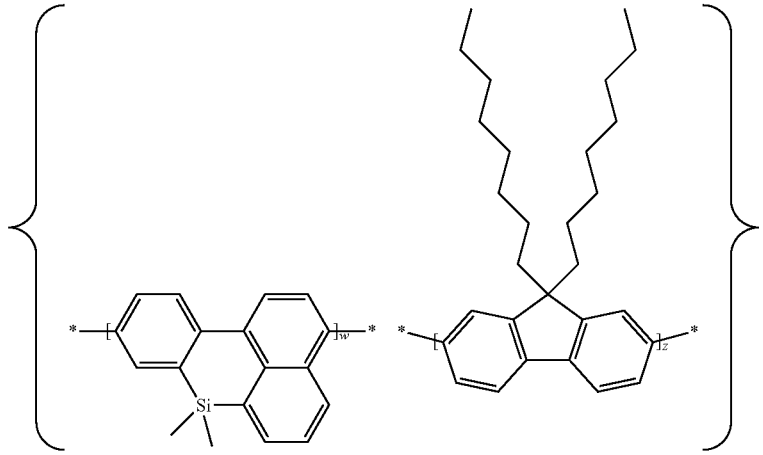

In some embodiments of Compounds VI-1 to VI-3, w=0.6, z=0.4; in some embodiments, w=0.8, z=0.2.

7. Electronic Devices

Organic electronic devices that may benefit from having one or more layers including at least one compound, polymer or copolymer as described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), (4) devices that convert light of one wavelength to light of a longer wavelength, (e.g., a down-converting phosphor device); and (5) devices that include one or more electronic components that include one or more organic semi-conductor layers (e.g., a transistor or diode). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

One illustration of an organic electronic device structure including at least one compound, polymer or copolymer as described herein is shown in FIG. 1. The device 100 has a first electrical contact layer, an anode layer 110 and a second electrical contact layer, a cathode layer 160, and a photoactive layer 140 between them. Additional layers may optionally be present. Adjacent to the anode may be a hole injection layer 120, sometimes referred to as a buffer layer. Adjacent to the hole injection layer may be a hole transport layer 130, including hole transport material. Adjacent to the cathode may be an electron transport layer 150, including an electron transport material. As an option, devices may use one or more additional hole injection or hole transport layers (not shown) next to the anode 110 and/or one or more additional electron injection or electron transport layers (not shown) next to the cathode 160. Layers 120 through 150 are individually and collectively referred to as the organic active layers.

In some embodiments, in order to achieve full color, the light-emitting layer is pixellated, with subpixel units for each of the different colors. An illustration of a pixellated device is shown in FIG. 2. The device 200 has anode 110, hole injection layer 120, hole transport layer 130, photoactive layer 140, electron transport layer 150, and cathode 160. The photoactive layer is divided into subpixels 141, 142, 143, which are repeated across the layer. In some embodiments, the subpixels represent red, blue and green color emission. Although three different subpixel units are depicted in FIG. 2, two or more than three subpixel units may be used.

The different layers will be discussed further herein with reference to FIG. 1. However, the discussion applies to FIG. 2 and other configurations as well.

In some embodiments, the different layers have the following range of thicknesses: anode 110, 500-5000 Å, in some embodiments, 1000-2000 Å; hole injection layer 120, 50-2000 Å, in some embodiments, 200-1000 Å; hole transport layer 130, 50-3000 Å, in some embodiments, 200-2000 Å; photoactive layer 140, 10-2000 Å, in some embodiments, 100-1000 Å; electron transport layer 150, 50-2000 Å, in some embodiments, 100-1000 Å; cathode 160, 200-10000 Å, in some embodiments, 300-5000 Å. The desired ratio of layer thicknesses will depend on the exact nature of the materials used.

One or more of the new compounds having Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c described herein may be present in one or more of the electroactive layers of a device.

In some embodiments, the new compounds having Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c are useful as hole transport materials in layer 130.

In some embodiments, the new compounds having Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c are useful as photoactive materials in layer 140. In some embodiments, the new compounds are present as photoactive dopant materials in one or more host materials. The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material. The term "host material" is intended to mean a material to which a dopant is added. The host material may or may not have electronic characteristic(s) or the ability to emit, receive, or filter radiation. In some embodiments, the host material is present in higher concentration.

In some embodiments, the new compounds having Formula II-a, Formula II-b, or Formula II-c, are useful as photoactive materials in layer 140.

In some embodiments, the new compounds having Formula I, Formula III-a, Formula III-b, Formula III-c, Formula IV-a, Formula IV-b, or Formula IV-c or a copolymer having at least one monomeric unit of Formula V-a, Formula V-b, or Formula V-c, where the compounds and monomeric units have at least two amino groups, are useful as photoactive materials in layer 140.

In some embodiments, the new compounds having Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c are useful as host materials for photoactive dopant materials in photoactive layer 140.

In some embodiments, the new compounds having Formula I, Formula III-a, Formula III-b, Formula III-c, Formula IV-a, Formula IV-b, or Formula IV-c or a copolymer having at least one monomeric unit of Formula V-a, Formula V-b, or Formula V-c, where the compounds and monomeric units have no amino groups, are useful as host materials for photoactive dopant materials in photoactive layer 140.

In some embodiments, an organic electronic device includes an anode, a cathode, and at least one organic active layer therebetween, where the organic active layer includes a compound of Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c.

In some embodiments, an organic electronic device includes an anode, a cathode, and a photoactive layer therebetween, where the photoactive layer includes a compound of Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c.

In some embodiments, an organic electronic device includes an anode, a cathode, and a photoactive layer therebetween, and further includes an additional organic active layer including a compound of Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c. In some embodiments, the additional organic active layer is a hole transport layer.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also include an organic material such as polyaniline as described in "Flexible light-emitting diodes made from soluble conducting polymer," Nature vol. 357, pp 477 479 (11 June 1992). At least one of the anode and cathode should be at least partially transparent to allow the generated light to be observed.

Optional hole injection layer 120 includes hole injection materials. The term "hole injection layer" or "hole injection material" is intended to mean electrically conductive or semiconductive materials and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules, and may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like. The hole injection layer 120 can include charge transfer compounds, and the like, such as copper phthalocyanine and the tetrathiafulvalene-tetracyanoquinodimethane system (TTF-TCNQ). In some embodiments, the hole injection layer 120 is made from a dispersion of a conducting polymer and a colloid-forming polymeric acid. Such materials have been described in, for example, published U.S. patent applications 2004-0102577, 2004-0127637, and 2005-0205860.

Layer 130 includes hole transport material.

In some embodiments, layer 130 includes a compound having Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c. In some embodiments, layer 130 includes only a compound having Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c, where additional materials that would materially alter the principle of operation or the distinguishing characteristics of the layer are not present.

In some embodiments, layer 130 includes other hole transport materials. Examples of hole transport materials for the hole transport layer have been summarized for example, in Kirk-Othmer Encyclopedia of Chemical Technology, Fourth Edition, Vol. 18, p. 837-860, 1996, by Y. Wang. Both hole transporting small molecules and polymers can be used. Commonly used hole transporting molecules include, but are not limited to: 4,4',4"-tris(N,N-diphenyl-amino)-triphenylamine (TDATA); 4,4',4"-tris(N-3-methylphenyl-N-phenyl-amino)-triphenylamine (MTDATA); N,N'-diphenyl-N,N'-bis(3-methylphenyl)-[1,1'-biphenyl]-4,4'-diamine (TPD); 4,4'-bis(carbazol-9-yl)biphenyl (CBP); 1,3-bis(carbazol-9-yl)benzene (mCP); 1,1-bis[(di-4-tolylamino) phenyl]cyclohexane (TAPC); N,N'-bis(4-methylphenyl)-N,N'-bis(4-ethylphenyl)-[1,1'-(3,3'-dimethyl)biphenyl]-4,4'-diamine (ETPD); tetrakis-(3-methylphenyl)-N,N,N',N'-2,5-phenylenediamine (PDA); α-phenyl-4-N,N-diphenylaminostyrene (TPS); p-(diethylamino)benzaldehyde diphenylhydrazone (DEH); triphenylamine (TPA); bis[4-(N,N-diethylamine)-2-methylphenyl](4-methylphenyl)methane (MPMP); 1-phenyl-3-[p-(diethylamino)styryl]-5-[p-(diethylamino)phenyl] pyrazoline (PPR or DEASP); 1,2-trans-bis(9H-carbazol-9-yl)cyclobutane (DCZB); N,N,N',N'-tetrakis(4-methylphenyl)-(1,1'-biphenyl)-4,4'-diamine (TTB); N,N'-bis(naphthalen-1-yl)-N,N'-bis-(phenyl)benzidine (α-NPB); and porphyrinic compounds, such as copper phthalocyanine. Commonly used hole transporting polymers include, but are not limited to, polyvinylcarbazole, (phenylmethyl)polysilane, poly(dioxythiophenes), polyanilines, and polypyrroles. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable, Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4,9,10-dianhydride.

Depending upon the application of the device, the photoactive layer 140 can be a light-emitting layer that is activated by an applied voltage (such as in a light-emitting diode or light-emitting electrochemical cell), a layer of material that absorbs light and emits light having a longer wavelength (such as in a down-converting phosphor device), or a layer of material that responds to radiant energy and generates a signal with or without an applied bias voltage (such as in a photodetector or photovoltaic device).

In some embodiments, the photoactive layer includes a compound having Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c as a photoactive dopant material. In some embodiments, the photoactive layer further comprises a host material. Examples of host materials include, but are not limited to, chrysenes, phenanthrenes, triphenylenes, phenanthrolines, naphthalenes, anthracenes, quinolines, isoquinolines, quinoxalines, phenylpyridines, indolocarbazoles, furans, benzofurans, dibenzofurans, benzodifurans, and metal quinolinate complexes. In some embodiments, the host materials are deuterated.

In some embodiments, the photoactive layer includes a compound having Formula II-a, Formula II-b, or Formula II-c as a photoactive dopant, and further includes a host material.

In some embodiments, the photoactive layer includes only a compound having Formula II-a, Formula II-b, or Formula II-c as a photoactive dopant, and a host material, where additional materials that would materially alter the principle of operation or the distinguishing characteristics of the layer are not present.

In some embodiments, the photoactive layer includes only a compound having Formula II-a, Formula II-b, or Formula II-c as a photoactive dopant, a first host material, and a second host material, where additional materials that would materially alter the principle of operation or the distinguishing characteristics of the layer are not present.

In some embodiments, the photoactive layer includes a compound having Formula I, Formula III-a, Formula III-b, Formula III-c, Formula IV-a, Formula IV-b, or Formula IV-c or a copolymer having at least one monomeric unit of Formula V-a, Formula V-b, or Formula V-c, where the compounds and monomeric units have at least two amino groups, as a photoactive dopant, and further includes a host material.

In some embodiments, the photoactive layer includes only a compound having Formula I, Formula III-a, Formula III-b, Formula III-c, Formula IV-a, Formula IV-b, or Formula IV-c or a copolymer having at least one monomeric unit of Formula V-a, Formula V-b, or Formula V-c, where the compounds and monomeric units have at least two amino groups, as a photoactive dopant, and a host material, where additional materials that would materially alter the principle of operation or the distinguishing characteristics of the layer are not present.

In some embodiments, the photoactive layer includes only a compound having Formula I, Formula III-a, Formula III-b, Formula III-c, Formula IV-a, Formula IV-b, or Formula IV-c or a copolymer having at least one monomeric unit of Formula V-a, Formula V-b, or Formula V-c, where the compounds and monomeric units have at least two amino groups, as a photoactive dopant, a first host material, and a second host material, where additional materials that would materially alter the principle of operation or the distinguishing characteristics of the layer are not present.

In some embodiments, the photoactive layer includes a compound having Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c as host material and additionally includes a photoactive dopant. The photoactive dopant can be an organic electroluminescent ("EL") material. Any EL material can be used in the devices, including, but not limited to, small molecule organic fluorescent compounds, fluorescent and phosphorescent metal complexes, conjugated polymers, and mixtures thereof. Examples of fluorescent compounds include, but are not limited to, chrysenes, pyrenes, perylenes, rubrenes, coumarins, anthracenes, thiadiazoles, benzofluorenes, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. In some cases the small molecule fluorescent or organometallic materials are deposited as a dopant with a host material to improve processing and/or electronic properties. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In some embodiments, the photoactive layer further includes a second host material. Examples of second host materials include, but are not limited to, chrysenes, phenanthrenes, triphenylenes, phenanthrolines, naphthalenes, anthracenes, quinolines, isoquinolines, quinoxalines, phenylpyridines, indolocarbazoles, furans, benzofurans, dibenzofurans, benzodifurans, and metal quinolinate complexes.

In some embodiments, photoactive layer 140 includes a host compound having Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c and a photoactive dopant.

In some embodiments, photoactive layer 140 includes only a host compound having Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c, and a photoactive dopant, where additional materials that would materially alter the principle of operation or the distinguishing characteristics of the layer are not present.

In some embodiments, photoactive layer 140 includes a photoactive dopant, a host material having Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c, and a second host material.

In some embodiments, photoactive layer 140 includes only a photoactive dopant, a first host material having Formula I, Formula II-a, Formula II-b, Formula II-c, Formula III-a, Formula III-b, Formula III-c, Formula IV-a, Formula IV-b, or Formula IV-c or a copolymer having at least one monomeric unit of Formula V-a, Formula V-b, or Formula V-c, and a second host material, where additional materials that would materially alter the principle of operation or the distinguishing characteristics of the layer are not present.

In some embodiments, photoactive layer 140 includes a host compound having Formula I, Formula III-a, Formula III-b, Formula III-c, Formula IV-a, Formula IV-b, or Formula IV-c or a copolymer having at least one monomeric unit of Formula V-a, Formula V-b, or Formula V-c, where the compounds and monomeric units have no amino groups, and a photoactive dopant.

In some embodiments, photoactive layer 140 includes only a host compound having Formula I, Formula III-a, Formula III-b, Formula III-c, Formula IV-a, Formula IV-b, or Formula IV-c or a copolymer having at least one monomeric unit of Formula V-a, Formula V-b, or Formula V-c, where the compounds and monomeric units have no amino groups, and a photoactive dopant, where additional materials that would materially alter the principle of operation or the distinguishing characteristics of the layer are not present.

In some embodiments, photoactive layer 140 includes a photoactive dopant, a host material having Formula I, Formula III-a, Formula III-b, Formula III-c, Formula IV-a, Formula IV-b, or Formula IV-c or a copolymer having at least one monomeric unit of Formula V-a, Formula V-b, or Formula V-c, where the compounds and monomeric units have no amino groups, and a second host material.

In some embodiments, photoactive layer 140 includes only a photoactive dopant, a first host material having Formula I, Formula III-a, Formula III-b, Formula III-c, Formula IV-a, Formula IV-b, or Formula IV-c or a copolymer having at least one monomeric unit of Formula V-a, Formula V-b, or Formula V-c, where the compounds and monomeric units have no amino groups, and a second host material, where additional materials that would materially alter the principle of operation or the distinguishing characteristics of the layer are not present.

Optional layer 150 can function both to facilitate electron transport, and also serve as a confinement layer to prevent quenching of the exciton at layer interfaces. Preferably, this layer promotes electron mobility and reduces exciton quenching.

In some embodiments, layer 150 includes other electron transport materials. Examples of electron transport materials which can be used in the optional electron transport layer 150, include metal chelated oxinoid compounds, including metal quinolate derivatives such as tris(8-hydroxyquinolato) aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato) zirconium (ZrQ): and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); triazines; fullerenes; and mixtures thereof. In some embodiments, the electron transport material is selected from the group consisting of metal quinolates and phenanthroline derivatives. In some embodiments, the electron transport layer further includes an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

An optional electron injection layer may be deposited over the electron transport layer. Examples of electron injection materials include, but are not limited to, Li-containing organometallic compounds, LiF, $Li_2O$. Li quinolate, Cs-containing organometallic compounds, CsF, $Cs_2O$, and $Cs_2CO_3$. This layer may react with the underlying electron transport layer, the overlying cathode, or both. When an electron injection layer is present, the amount of material deposited is generally in the range of 1-100 Å, in some embodiments 1-10 Å.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device layers can be formed by any deposition technique, or combinations of techniques, including vapor deposition, liquid deposition, and thermal transfer. Substrates such as glass, plastics, and metals can be used. Conventional vapor deposition techniques can be used, such as thermal evaporation, chemical vapor deposition, and the like. The organic layers can be applied from solutions or dispersions in suitable solvents, using conventional coating or printing techniques, including but not limited to spin-coating, dip-coating, roll-to-roll techniques, ink-jet printing, continuous nozzle printing, screen-printing, gravure printing and the like.

For liquid deposition methods, a suitable solvent for a particular compound or related class of compounds can be readily determined by one skilled in the art. For some applications, it is desirable that the compounds be dissolved in non-aqueous solvents. Such non-aqueous solvents can be relatively polar, such as $C_1$ to $C_{20}$ alcohols, ethers, and acid esters, or can be relatively non-polar such as $C_1$ to $C_{12}$ alkanes or aromatics such as toluene, xylenes, trifluorotoluene and the like. Other suitable liquids for use in making the liquid composition, either as a solution or dispersion as described herein, including the new compounds, includes, but not limited to, chlorinated hydrocarbons (such as methylene chloride, chloroform, chlorobenzene), aromatic hydrocarbons (such as substituted and non-substituted toluenes and xylenes), including triflurotoluene), polar solvents (such as tetrahydrofuran (THP), N-methyl pyrrolidone) esters (such as ethylacetate) alcohols (isopropanol), ketones (cyclopentatone) and mixtures thereof. Suitable solvents for electroluminescent materials have been described in, for example, published PCT application WO 2007/145979.

In some embodiments, the device is fabricated by liquid deposition of the hole injection layer, the hole transport layer, and the photoactive layer, and by vapor deposition of the anode, the electron transport layer, an electron injection layer and the cathode.

It is understood that the efficiency of devices made with the new compositions described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

In some embodiments, the device has the following structure, in order: anode, hole injection layer, hole transport layer, photoactive layer, electron transport layer, electron injection layer, cathode.

Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

EXAMPLES

The concepts described herein will be further described in the following examples, which do not limit the scope of the invention described in the claims.

Synthesis Example 1

This example illustrates the preparation of a compound having Formula I, 3,9-bis-(2-naphthyl)-7,7-dimethyl-7H-benz[de]anthracene, which is Compound I-2.

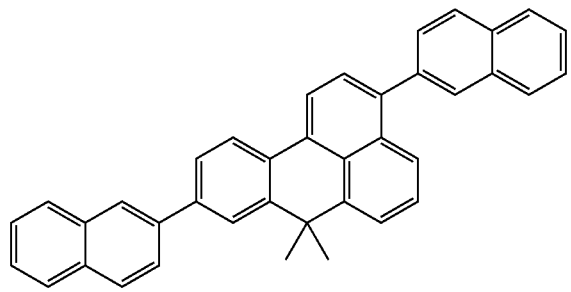

Compound I-2

1.00 grams (2.49 mmoles) of 3,9-dibromo-7,7-dimethyl-7H-benz[de]anthracene was dissolved in 50 ml of toluene under nitrogen in a 100 ml 3-neck flask. The suspension was stirred with 1.03 grams (6.0 mmoles) of naphthalene-2-boronic acid, 8.2 grams (25 mmoles) of cesium carbonate and degassed under a stream of nitrogen for 20 minutes. The mixture was then treated with 0.17 gram (0.15 mmole) of tetrakis(triphenylphosphine)palladium and heated to reflux under nitrogen for 16.5 hours. The mixture was cooled to room temperature and then filtered through a pad of celite, florisil and silica gel. The pad was washed with several portions of toluene.

The toluene filtrate was concentrated to give 0.9 gram of an off-white solid. The solid was recrystallized from 20 ml of toluene under nitrogen in a 100 ml round flask. The clear solution was allowed to stand at room temperature under nitrogen for 18 hours. The resulting white solid was filtered off, washed twice with a minimal amount of toluene, washed with hexane, air dried, and then redissolved in about 30 ml of dichloromethane with sonication. The solution was passed through a short column of basic alumina and the column was eluted with dichloromethane followed by evaporation of eluent.

The product was dissolved in 15 ml of hot toluene under nitrogen and allowed to stand for 18 hours at room temperature under nitrogen. It was filtered off, washed twice with minimal cold toluene, washed with hexane, air dried, and dried under vacuum at room temperature to give 0.56 gram of a white solid (99.9% purity by UPLC/MS in THF, m/z=497, 481). UV-VIS: $\lambda_{max}$ 226, 360 nm. $^1$H NMR (CDCl3): 8.31 (d, 1H), 8.27 (d, 1H), 8.17 (s, 1H), 8.06 (s, 1H), 8.03 (s, 1H), 7.91-8.00 (m, 6H), 7.88 (d, 2H), 7.76 (d, 2H), 7.71 (d, 1H), 7.63 (d, 1H), 7.52-7.58 (m, 5H), 1.90 (s, 6H).

Synthesis Example 2

This example illustrates the preparation of a compound having Formula II, (N³,N⁹-bis(phenyl)-7,7-dimethyl-N³,N⁹-bis(1-naphthyl)-7H-benz[de]anthracene-3,9-diamine), which is Compound II-1.

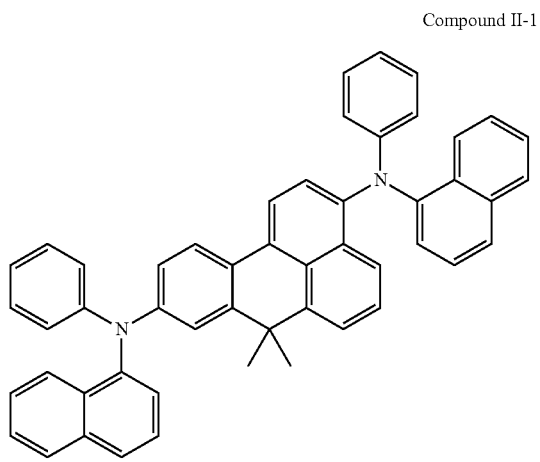 [SMILES: CC1(C)c2cc(N(c3ccccc3)c3cccc4ccccc34)ccc2-c2ccc(N(c3ccccc3)c3cccc4ccccc34)c3cccc1c23]

Compound II-1

N-Phenyl-1-naphthylamine (0.57 g, 2.61 mmol), 3,9-dibromo-7,7-dimethyl-7H-benz[de]anthracene (0.5 g, 1.24 mmol), Pd2(dba)3 (23 mg, 2 mol %), tri-tert-butylphosphine (10 mg, 4 mol %), sodium tert-butoxide (0.261 g, 2.73 mmol) were added to the 250 mL round bottom reaction flask. This mixture was stirred at room temperature for 5 min and then heated to 80° C. overnight. The reaction was shown complete by TLC/UPLC. The reaction mixture was cooled down to ambient temperature and water (100 ml) added and the reaction mixture was stirred in the air for 30 min, After that reaction mixture passed through a layer of celite, florisil and silica gel washing with toluene (100 mL). Solvent was removed on rotovap, the residue was redissolved in dichloromethane and evaporated onto celite and separated by column chromatography on silica gel eluting with hexanes-dichloromethane. All fractions containing the product were combined, solvents were removed by rotary evaporation and the residue was precipitated from toluene solution by pouring into methanol to give, after collection of the solid by filtration and drying, 0.22 g (yield 26%, 99.59% purity by UPLC).UV-VIS, $\lambda_{max}$ 219, 403 nm. MS: 679 (MH+). ¹H-NMR (dmso-d6, 500 MHz): 1.45 (s, 6H), 6.59 (d, 2H, J=8 Hz), 6.78 (dd, 1H, J=8; 2 Hz), 6.84 (t, 1H, J=7 Hz), 6.99 (t, 1H, J=7 Hz), 7.03 (dd, 2H, J=8; 1 Hz), 7.13-7.29 (m, 8H), 7.37-7.45 (m, 5H), 7.49-7.52 (m, 2H), 7.59 (t, 1H, J=7 Hz), 7.65 (d, 1H, J=7 Hz), 7.78 (d, 1H, J=8 Hz), 7.84 (t, 2H, J=2H), 7.91-8.02 (m, 5H).

Synthesis Example 3

This example illustrates the preparation of a compound having Formula II, (N,N'-bis[3-(3,6-di-tert-butyl-9H-carbazol-9-yl)phenyl]-7,7-dimethyl-N,N'-bis(4'-propylbiphenyl-4-yl)-7H-7H-benz[de]anthracene-3,9-diamine), which is Compound II-2.

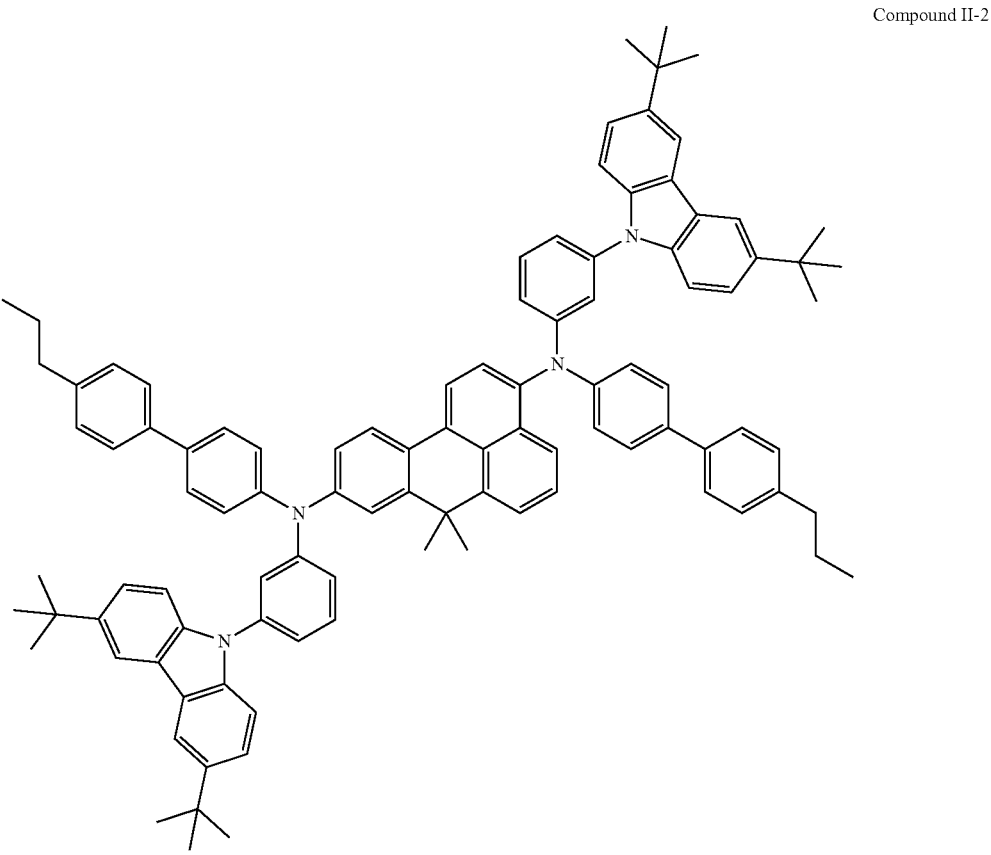 [SMILES: CCCc1ccc(-c2ccc(N(c3cccc(-n4c5ccc(C(C)(C)C)cc5c5cc(C(C)(C)C)ccc54)c3)c3ccc4c(c3)C(C)(C)c3cccc5c(N(c6ccc(-c7ccc(CCC)cc7)cc6)c6cccc(-n7c8ccc(C(C)(C)C)cc8c8cc(C(C)(C)C)ccc87)c6)ccc-4c35)cc2)cc1]

Compound II-2

3(a). Synthesis and characterization of 3-(3,6-di-tert-butyl-9H-carbazol-9-yl)phenyl]-[1,1'-biphenyl]-4-amine, N-(3-bromophenyl)2,6-di-tert-butylcarbazole (2.05 g, 4.73 mmol), 4'-(n-propyl)-4-biphenylamine (1 g, 4.73 mmol), Pd2(dba)3 (90 mg, 2 mol %), tri-tert-butylphosphine (40 mg, 4 mol %), and sodium tert-butoxide (0.5 g, 5.2 mmol) were added to the 250 mL round bottom reaction flask. This mixture was stirred at room temperature for 5 min and then heated to 33° C. overnight. The reaction was shown complete by TLC/UPLC. The reaction mixture was cooled down to ambient temperature and water (100 ml) added and the reaction mixture was stirred in the air for 30 min. After that reaction mixture passed through a layer of celite, florisil and silica gel washing with toluene (100 mL). Solvent was removed by rotary evaporation, the residue was redissolved in dichloromethane and evaporated onto celite and separated by column chromatography on silica gel eluting with hexanes-dichloromethane. All fractions containing the product were combined, solvents were removed by rotary evaporation and the residue was precipitated from toluene solution by pouring into methanol to give, after collection of the solid by filtration and drying, 2.3 g, 86% yield of the product.MS: 565 (MH+). $^1$H-NMR (CDCl3, 500 MHz): 0.97 (t, 3H, J=7 Hz), 1.47 (s, 18H), 1.63-1.71 (m, 1H), 2.62 (t, J=8 Hz), 5.91 (br s, 1H), 7.10-7.27 (m, 8H), 7.40-7.52 (m, 8H), 8.13 (d, 2H, J=2 Hz).

3(b). 3-(3,6-di-tert-butyl-9H-carbazol-9-yl)phenyl]-[1,1'-biphenyl]-4-amine (1.06, 1.88 mmol), 3,9-dibromo-7,7-dimethyl-7H-benz[de]anthracene (0.343 g, 0.85 mmol), Pd$_2$(dba)$_3$ (34 mg, 2 mol %), tri-tert-butylphosphine (15 mg, 4 mol %), and sodium tert-butoxide (0.43 g, 4.51 mmol) were added to the 250 mL round bottom reaction flask. This mixture was stirred at room temperature for 5 min and then heated to 80 C overnight. The reaction was shown complete by TLC/UPLC. The reaction mixture was cooled down to ambient temperature and water (100 ml) added and the reaction mixture was stirred in the air for 30 min. Next, the reaction mixture was passed through a layer of celite, florisil and silica gel washing with toluene (100 mL).

Solvent was removed on rotovap, the residue was redissolved in dichloromethane and evaporated onto celite and separated by column chromatography on silica gel eluting with hexanes-dichloromethane. All fractions containing the product combined, solvents evaporated and the residue was precipitated from toluene solution onto methanol to give 0.52 g (yield 45%, 99.9% purity by UPLC). UV-VIS, $\lambda_{max}$ 205, 241, 296, 326, 405 nm. MS: 1372 (MH+). $^1$H-NMR (CDCl3, 500 MHz): 0.95-0.99 (m, 6H), 1.40 (s, 18H), 1.44 (s, 18H), 1.65-1.70 (m, 10H), 2.60-2.65 (m, 4H), 7.11-7.55 (m, 37H), 7.67 (d, 1H, J=8 Hz), 7.95 (d, 1H, J=8 Hz), 8.00 (d, 1H, J=8 Hz), 8.03 (d, 2H, J=2 Hz), 8.09 (d, 2H, J=2 Hz).

Synthesis Example 4

This example illustrates the preparation of a compound having Formula H, 7,7-dimethyl-N,N,N',N',N'',N''-hexaphenyl-7H-benzo[e]naphtho[1,8-bc]siline-2,5,9-triamine, which is Compound II-12.

Compound II-12

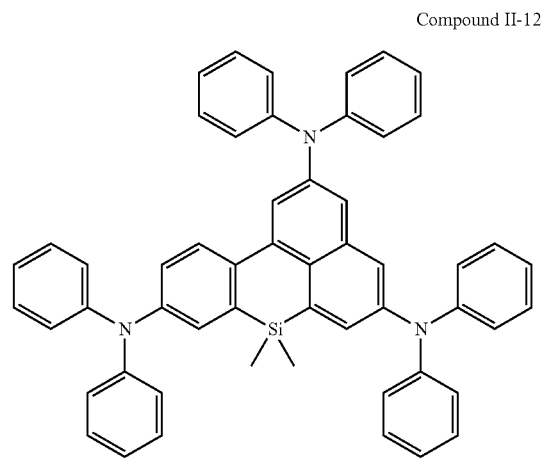 [SMILES: C[Si]1(C)c2cc(N(c3ccccc3)c3ccccc3)ccc2-c2cc(N(c3ccccc3)c3ccccc3)cc3cc(N(c4ccccc4)c4ccccc4)cc1c23]

Into a 100-mL round-bottom flask was added 2,5,9-tribromo-7,7-dimethyl-7H-benzo[e]naphtho[1,8-bc]siline (0.521 g, 1.05 mmol). diphenylamine (0.682 g, 4.03 mmol) and sodium tert-butoxide (0.415 g, 4.32 mmol). Toluene (30 mL) was then added, and the mixture was sparged with N$_2$ for 20 minutes. Inside the glovebox, Pd$_2$(dba)$_3$ (0.105 g, 0.115 mmol) and tri-tert-butyl-phosphine (0.051 g, 0.25 mmol) were mixed with toluene (20 mL) in a sealed 100-mL flask and stirred for 20 minutes. The catalyst mixture was then transferred to the reaction flask via cannula, and the reaction mixture was stirred at 120 ° C. for 14 h. The reaction mixture was allowed to cool to room temperature and then diluted with ethyl acetate(100 mL).The mixture was then passed through a plug of silica and Celite®. The product was purified by flash silica chromatography followed by recrystallization in hexanes to afford 0.40 g of a yellow solid (0.40 g, 50%). $^1$H NMR (CD$_2$Cl$_2$, 499.8 MHz) δ 8.20 (m, 1H), 7.68 (m, 3H), 7.53 (m, 1H), 7.33 (m, 1H). 7.2-7.0 (m, 17H), 6.87-6.82 (m, 14H), 0.41 (s, 6H). UPLC-MS APCI$^+$ (m/z) Calcd for C$_{54}$H$_{43}$N$_3$Si ([M+H]$^+$) 762.3299. Found 762.60.

Synthesis Example 5

This example illustrates the preparation of a compound having Formula II, N,N,n',N',N'',N''-hexa(biphenyl-4-yl)-7,7-dimethyl-7H-benzo[e]naphtho[1,8-bc]siline-2,5,9-triamine, which is Compound II-13.

Compound II-13

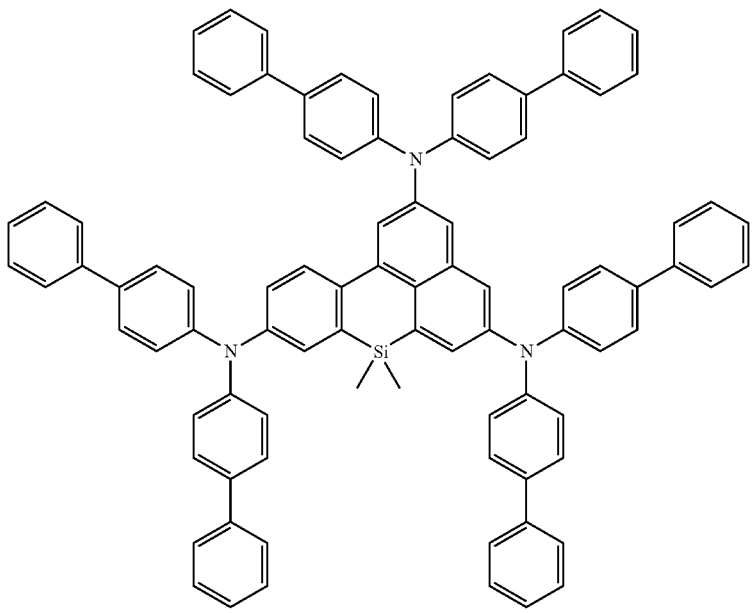

Into a 100-mL round-bottom flask was added 2,5,9-tribromo-7,7-dimethyl-7H-benzo[e]naphtho[1,8-bc]siline (0.500 g, 1.01 mmol). N-(biphenyl-4-yl)biphenyl-4-amine (1.08 g, 3.36 mmol) and sodium tert-butoxide (0.394 g, 4.10 mmol). Toluene (30 mL) was then added, and the mixture was sparged with $N_2$ for 20 minutes. Inside the glovebox, $Pd_2(dba)_3$ (0.092 g, 0.10 mmol) and tri-tert-butyl-phosphine (0.044 g, 0.20 mmol) were mixed with toluene (20 mL) in a sealed 100-mL flask and stirred for 20 minutes. The catalyst mixture was then transferred to the reaction flask via cannula, and the reaction mixture was stirred at 120° C. for 16 h. The reaction mixture was allowed to cool to room temperature and then diluted with ethyl acetate(100 mL).The mixture was then passed through a plug of silica and Celite®. The product was purified by flash silica chromatography followed by recrystallization from toluene/hexanes to afford a yellow solid 1.0 g, 81%). UPLC-MS APCI$^+$ (m/z) Calcd for $C_{90}H_{67}N_3Si$ ([M+H]$^+$) 1218.5177. Found 1219.44

Synthesis Example 6

This example illustrates the preparation of a compound having Formula I, 4,4',4"-(7,7-dimethyl-7H-benzo[e]naphtho[1,8-bc]siline-2,5,9-triyl)tris(N,N-diphenylaniline), which is Compound I-28.

Compound I-28

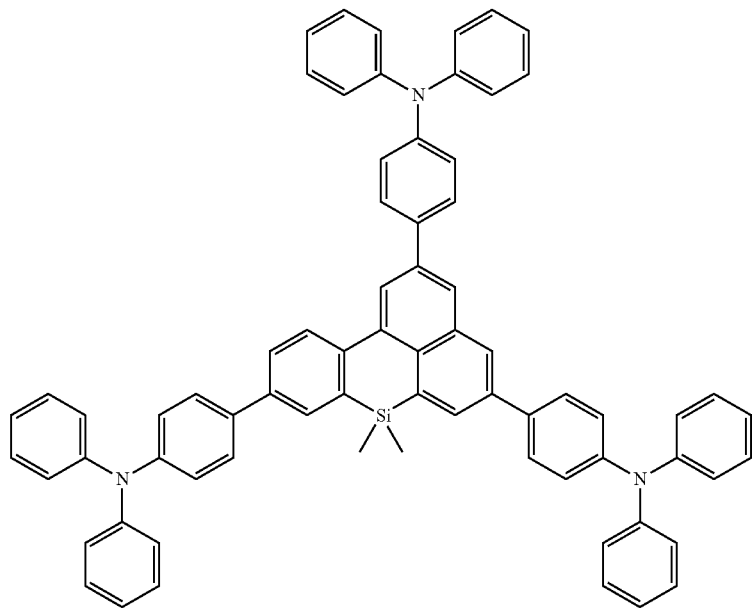

Into an oven-dried, 100-mL round-bottom flask, fitted with a condenser, was added [4-(diphenylamino)phenyl] boronic acid (0.959 g, 3.32 mmol), 2,5,9-tribromo-7,7-dimethyl-7H-benzo[e]naphtho[1,8-bc] siline (0.500 g, 1.01 mmol) and powdered $K_3PO_4 \cdot H_2O$ (1.38 g, 3.62 mmol). Toluene (18 mL) was then added, and the mixture was sparged with $N_2$ for 20 minutes. Inside a glove box, an oven dried, 50-mL flask equipped with a stir bar and rubber septum was charged with $Pd_2(dba)_3$ (92 mg, 0.060 mmol), 2-dicyclohexylphosphino-2',6'-dimethoxybiphenyl, S-phos, (165 mg, 0.24 mmol) and toluene (12 mL); the catalyst mixture was stirred for 30 minutes. The catalyst mixture was transferred to the 100-mL flask via cannula. and the reaction mixture was stirred at 130° C. for 8 h under $N_2$. The reaction mixture was diluted with 100 mL of ethyl acetae and washed with brine (2×100 mL), dried over $MgSO_4$ filtered, and purified by flash chromatography eluting with 4:1 hexanes/DCM to yield a yellow solid (240 mg, 20%). UPLC-MS APCI$^+$ (m/z) Calcd for $C_{72}H_{55}N_3Si$ ([M+H]$^+$) 990.4238. Found 990.98.

Synthesis Example 7

This example illustrates the preparation of a compound having Formula I, $N^3,N^9$-bis(3-(9H-carbazol-9-yl)phenyl)-7,7-dimethyl-N3,N9-diphenyl-7H-benzo[de]anthracene-3,9-diamine, which is Compound I-1.

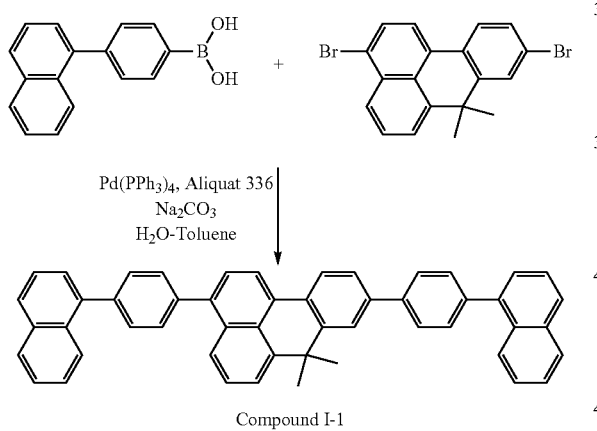

Compound I-1

To a 250 mL mL three-necked round bottom flask were added 3,9-dibromo-7,7-dimethyl-7H-benzo[de]anthracene (2.85 g, 7.08 mmol), (4-(naphthalen-1-yl)phenyl)boronic acid (3.69 g, 14.88 mmol), toluene (100 ml), aqueous sodium carbonate (2 M, 22 mL) and Aliquat 336 (1.00 g). With stirring, the system was purged with nitrogen for 20 min. Pd(PPh$_3$)$_4$ (245 mg, 0.21 mmol), was added and the system was purged for another 10 min. The reaction was stirred and refluxed under nitrogen overnight. During the time, some solid was formed. After cooling to ambient temperature, the solid was filtered off, dried in air and washed with DCM to give 3.5 g of crude product in 99.32% purity by UPLC analysis. The material was dissolved in chloroform (200 mL) and adsorbed onto Celite (22 g) and dried in the vacuum oven overnight. This was separated on preparative chromatography (CombiFlash) eluted with chloroform/hexanes gradient. Fractions were identified by UPLC analysis and the solvent was evaporated. The product was recrystallized from toluene /ethanol under heating, collected, rinsed with toluene/ethanol (3/2), and dried in the vacuum oven at 50° C. for 5 hours. The desired product was obtained as a white powder, 1.15 g in >99.9% purity by UPLC analysis, and 1.01 g was recovered in 99.85% purity. The structure of the product was confirmed by NMR analysis.

Synthesis Example 8

This example illustrates the preparation of a compound having Formula II, $N^3,N^9$-bis(3-(9H-carbazol-9-yl)phenyl)-7,7-dimethyl-N3,N9-diphenyl-7H-benzo[de]anthracene-3,9-diamine, which is Compound II-3.

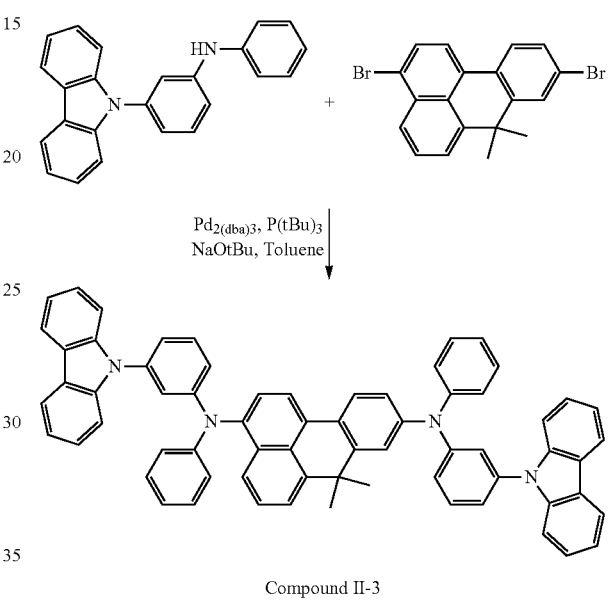

Compound II-3

In drybox, 3,9-dibromo-7,7-dimethyl-7H-benzo[de]anthracene (2.00 g, 4.97 mmol), 3-(9H-carbazol-9-yl)-N-phenylaniline (3.44 g, 10.19 mmol), Pd$_2$(DBA)$_3$ (92 mg, 0.10 mmol) and anhydrous toluene (90 ml) were taken in a 250 mL flask under nitrogen and stirred for 5 min. NaOtBu (1.00 g, 10.43 mmol) was added in small portions. The reaction was continued to stir at RT for one hour. The reaction was shown complete by UPLC analysis. It was removed from the drybox, and passed through a Celite plug to remove the insoluble. The solvent was removed by rotary evaporation and the residue was chromatographed on a Florosil* column (5×15 cm) eluted with DCM/hexane gradient (10%, 20% and 50%). The product containing fractions were collected and the solvent was evaporated. Two major collections were obtained, 2.4 g in 99.9% purity and 2.0 g in 95.0% purity. The former was dissolved in DCM (40 mL) and adsorbed onto Celite (8 g), and dried in the vacuum oven for an hour before separating on the preparative chromatography (CombiFlash) eluted with DCM/hexanes gradient. The product containing fractions were identified by UPLC analysis, collected, and precipitated from toluene (5 mL) into methanol (200 mL). The precipitate was collected, rinsed with methanol, and dried in the vacuum oven at 50° C. for 4 hours to give 276 mg of yellow amorphous solid in >99.9% purity by UPLC analysis. Less pure fractions and above 2.01 g of material were combined to give 3.46 g of product in 97.6% purity. The structure of the product was confirmed by NMR analysis.

Synthesis Example 9

This example illustrates the preparation of a compound having Formula II, $N^3,N^9$-bis(phenyl)-7,7-dimethyl-$N^3,N^9$-bis(4-carbazolyl-naphth-1-yl)-7H-benzo[de]anthracene-1,3-diamine, which is Compound II-14.

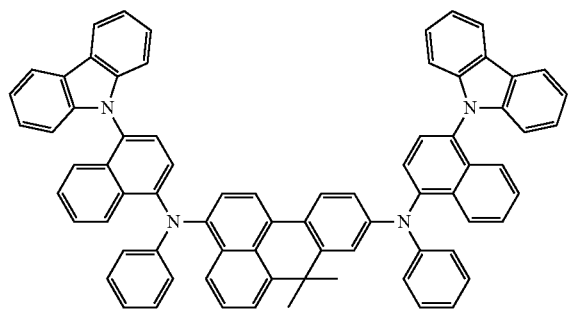 [SMILES: CC1(C)c2cc(N(c3ccccc3)c3ccc(-n4c5ccccc5c5ccccc54)c4ccccc34)ccc2-c2ccc(N(c3ccccc3)c3ccc(-n4c5ccccc5c5ccccc54)c4ccccc34)c3cccc1c23]

$N^3,N^9$-bis(phenyl)-7,7-dimethyl-$N^3,N^9$-bis(4-carbazolyl-naphth-1-yl)-7H-benzo[de]anthracene-1,3-diamine. 3,9-Dibromo-7,7-dimethyl-7H-benz[de]anthracene (0.986 g, 2.45 mmol), N-phenyl-1-(4-carbazolyl-naphthyl)amine (1.99 g, 5.18 mmol), Pd2(dba)3 (45 mg, 0.049 mmol), tri-tert-butylphosphine (20 mg, 0.098 mmol), sodium tert-butoxide (0.588 g, 6.13 mmol) and toluene (100 ml) were added to the 250 mL round bottom reaction flask. This mixture was stirred at room temperature for 5 min and then heated to 80° C. for 3 hours. The reaction was shown complete by TLCIUPLC. The reaction mixture was cooled down, water (100 ml) added and the reaction mixture was stirred in the air for 30 min. After that reaction mixture passed through a layer of celite, florisil and silica gel washing with toluene (100 mL). Solvent was removed by rotary evaporation, the residue was redissolved in dichloromethane and evaporated onto celite and purified by column chromatography on silica gel eluting with hexanes-dichloromethane. All fractions containing the product were combined, solvents were removed by rotary evaporation and the residue was passed through column filled with basic alumina. Fractions containing the product combined, eluent distilled off by using rotary evaporator, the residue redissolved in toluene and precipitated into methanol. Yield—1.22 g (1.21 mmol, 49%). MS: MH+=1010. UV-vis (toluene), lambda$_{max}$: 413 nm ($\epsilon$=40600). Photoluminescence (toluene): lambda$_{max}$: 451 nm

Synthesis Example 10

This example illustrates the preparation of a compound having Formula II, $N^1,N^4$-bis(4'-propyl-4-biphenyl)-$N^1,N^4$-bis(N-3-(2,6-di-tert-butylcarbazolyl)phenyl-)-7-phenyl-7H-benz[kl]acridine-1,4-diamine, which is Compound II-15.

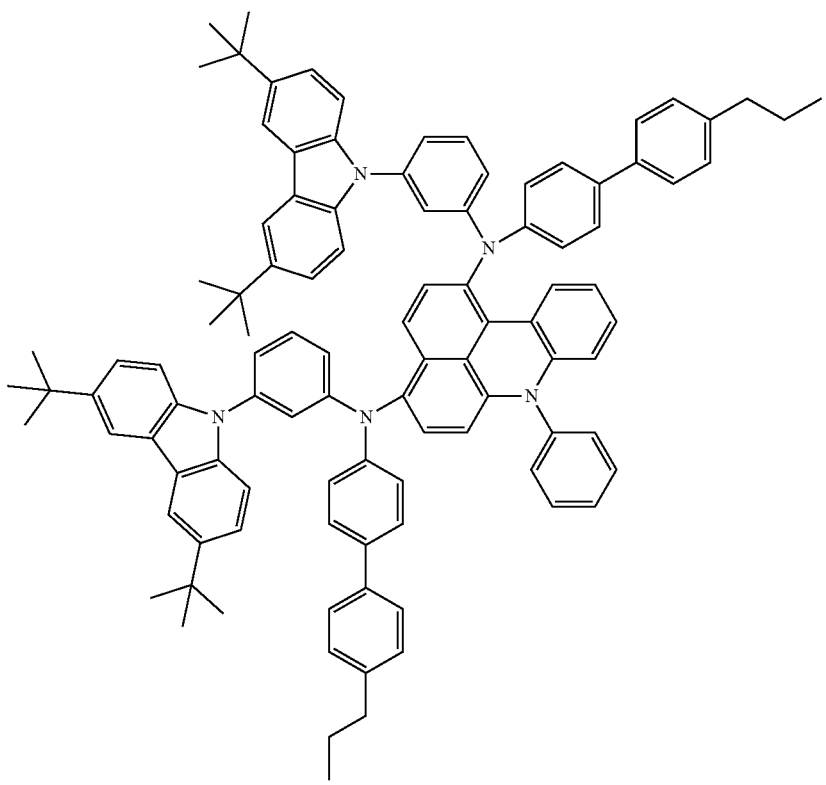 [SMILES: CCCc1ccc(-c2ccc(N(c3cccc(-n4c5ccc(C(C)(C)C)cc5c5cc(C(C)(C)C)ccc54)c3)c3ccc4c(N(c5ccc(-c6ccc(CCC)cc6)cc5)c5cccc(-n6c7ccc(C(C)(C)C)cc7c7cc(C(C)(C)C)ccc76)c5)ccc5c4c3-c3ccccc3N5c3ccccc3)cc2)cc1]

1,4-Dibromo-7-phenyl-7H-benz[kl]acridine (0.064 g, 0.141 mmol), 3-(3,6-di-tert-butyl-9H-carbazol-9-yl)phenyl]-[1,1'-biphenyl]-4-amine (0.167 g, 0.296 mmol), Pd2 (dba)3 (5 mg, 0.06 mmol), tri-tert-butylphosphine (2.3 mg, 0.011 mmol), sodium tert-butoxide (0.34 mg, 0.353 mmol) and toluene (25 ml) were added to the 250 mL round bottom reaction flask. This mixture was stirred at room temperature for 5 min and then heated to 80° C. for 1.5 hours. The reaction was shown complete by TLC/UPLC. The reaction mixture was cooled down, water (100 ml) added and the reaction mixture was stirred in the air for 30 min. After that reaction mixture passed through a layer of celite, florisil and silica gel washing with toluene (100 mL). Solvent was removed by rotary evaporation, the residue was redissolved in dichloromethane and evaporated onto celite and purified by column chromatography on silica gel eluting with hexanes-dichloromethane. Fractions containing product combined to give 154 mg of the product (0.1085 mmol, 77%). MS: MH+=1419. UV-vis (toluene), lambda$_{max}$: 440 nm ($\epsilon$=9510), 334 nm ($\epsilon$=59100). Photoluminescence (toluene): lambda$_{max}$: 524 nm.

Synthesis Example 11

This example illustrates the preparation of a compound having Formula II, $N^1,N^3$-bis(phenyl)-7,7-dimethyl-$N^1,N^3$-bis(4-biphenyl)-7H-benz[de]anthracene-1,3-diamine, which is Compound II-16.

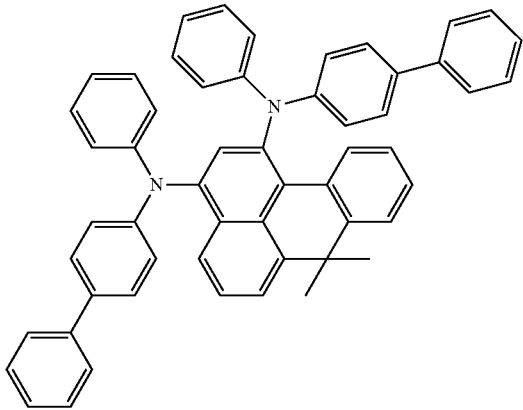 [SMILES: CC1(C)c2ccccc2-c2c(N(c3ccccc3)c3ccc(-c4ccccc4)cc3)cc(N(c3ccccc3)c3ccc(-c4ccccc4)cc3)c3cccc1c23]

1,3-dibromo-7,7-dimethyl-7H-benzo[de]anthracene (0.5 g, 1.24 mmol), N-phenyl-N-(4-biphenylamine) (0.57 g, 2.73 mmol), Pd2(dba)3 (25 mg, 0.25 mmol), tri-tert-butylphosphine (10 mg, 0.05 mmol), sodium tert-butoxide (0.261 mg, 2.73 mmol) and toluene (50 ml) were added to the 250 mL round bottom reaction flask. This mixture was stirred at room temperature for 5 min and then heated to 80° C. for 4 hours. The reaction was shown complete by TLC/UPLC. Reaction mixture was cooled down, transferred to fumehood, passed through filter filled with silica gel, florisil, basic alumina and celite washing with toluene. The crude product was placed on celite and subjected to ISCO column chromatography purification on silica gel by using hexanes—dichloromethane mixtures as eluent. Fractions containing desired product combined, solvent evaporated and the residue subjected to column filled with basic alumina using mixtures of hexanes and dichloromethane as eluent. Fractions containing desired product combined, eluent evaporated to volume approx. 5 ml and precipitate collected by filtration. The product was redissolved in toluene and precipitated into methanol to give 325 mg of the desired product. Additional 40 mg of product was obtained by evaporation of eluent to volume approx. 1 ml and collecting precipitate by filtration. Yield—365 mg (0.5 mmol, 40%). MS: MH+=731. $^1$H-NMR (toluene-d8, 500 MHz): 8.71 (d, 1H, J=9 Hz), 8.12 (d, 1H, J=9 Hz), 7.58 (s, 1H), 7.47 (d, 2H, J=8 Hz), 7.47-7.04 (m, 34H), 6.86 (t, 1H, J=7 Hz), 6.75 (t, 1H, J=7 Hz). UV-vis (toluene), lambda$_{max}$: 429 nm ($\epsilon$=22400). Photoluminescence (toluene): lambda$_{max}$: 469 nm.

DEVICE EXAMPLES (1) Materials

D-1 is a blue benzofluorene dopant. Such materials have been described, for example, in U.S. Pat. No. 8,465,848.

ET-1 is shown below

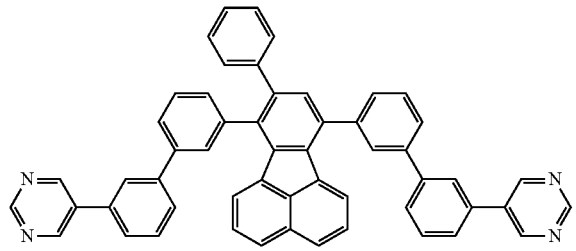 [SMILES: c1ccc(-c2cc(-c3cccc(-c4cccc(-c5cncnc5)c4)c3)c3c(c2-c2cccc(-c4cccc(-c5cncnc5)c4)c2)-c2cccc4cccc-3c24)cc1]

ET-2 is lithium quinolate.

ET-3 is an aryl phosphine oxide.

HIJ-1 is a hole injection material which is made from an aqueous dispersion of an electrically conductive polymer and a polymeric fluorinated sulfonic acid. Such materials have been described in, for example, U.S. Pat. No. 7,351,358.

HIJ-2 is 1,4,5,8,9,12-hexaazatriphenylenehexacarbonitrile.

Host H1 is a deuterated aryl-anthracene compound.

Host H2 is a deuterated aryl-anthracene compound.

HTM-1 is a hole transport material which is a triarylamine polymer. Such materials have been described in, for example, published US Application 2013-0082251.

HTM-2 is N,N'-bis(naphthalen-1-yl)-N,N'-bis-(phenyl)benzidine.

HTM-3 is a mono-arylamino phenanthrene compound.

(2) Device Fabrication

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Device Type 1: Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent. After cooling, the substrates were then spin-coated with a solution of hole transport material in a solvent of anisole:toluene (9:1, by volume), and then heated to remove solvent. After cooling the substrates were spin-coated with a methyl benzoate solution of the host and dopant, and heated to remove solvent. The substrates were masked and placed in a vacuum chamber. A layer of electron transport material was deposited by thermal evaporation, followed by a layer of electron injection material. Masks were then changed in vacuo and a layer of Al was deposited by thermal evaporation. The chamber was vented, and the devices were encapsulated using a glass lid, dessicant, and UV curable epoxy.

Device Type 2: Immediately before device fabrication the cleaned, patterned ITO substrates were treated with UV ozone for 10 minutes, Immediately after cooling, an aqueous dispersion of HIJ-1 was spin-coated over the ITO surface and heated to remove solvent, to form a short reduction layer ("SRL"). The workpieces were then placed in a vacuum chamber. Layers of hole injection material, hole transport materials, the photoactive and host materials, electron transport materials, and the Al cathode were then deposited sequentially by thermal evaporation using the appropriate masks. The chamber was vented, and the devices were encapsulated using a glass lid, desiccant, and UV curable epoxy.

(3) Device Characterization

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W. The color coordinates were determined using either a Minolta CS-100 meter or a Photoresearch PR-705 meter.

Device Examples 1 and 2

These examples illustrate the device performance of a device having a photoactive layer including the new composition described above. The devices were made according to Device Type 1. Device structure, in order (all percentages are by weight, based on the total weight of the layer):
Glass substrate
Anode: ITO (50 nm)
Hole injection layer: HIJ-1 (100 nm)
Hole transport layer: HTM-1 (100 nm)
Photoactive layer: 7% of dopant D-1+93% of host (38 nm); the host material is given below in Table 1
Electron transport layer: ET-1 (20 nm)
Electron injection layer: ET-2 (3.5 nm)
Cathode: Al (100 nm)

TABLE 1

Device results

| Example | Host | CE Cd/A | EQE (%) @1000 nits | Voltage @ 15 mA/cm$^2$ | CIE (x, y) |
|---|---|---|---|---|---|
| 1 | Compound I-1 | 4.4 | 5.0% | 5.0 | (0.138, 0.102) |
| 2 | Compound I-2 | 2.7 | 3.0% | 3.7 | (0.140, 0.099) |

CE is the current efficiency;
EQE = external quantum efficiency;
CIEx and CIEy are the x and y color coordinates according to the C.I.E. chromaticity scale (Commission Internationale de L'Eclairage, 1931).

Table 1 illustrates the use of Compounds I-1 and I-2 as hosts in the emissive layers of organic electronic devices.

Device Examples 3-7

These examples illustrate the device performance of a device having a photoactive layer including the new composition described above. The devices were made according to Device Type 1. Device structure, in order (all percentages are by weight, based on the total weight of the layer):
Glass substrate
Anode: ITO (50 nm)
Hole injection layer: HIJ-1 (100 nm)
Hole transport layer: HTM-1 (100 nm)
Photoactive layer: host H1 and dopant (38 nm), the dopant and host/dopant ratio are given below in Table 2
Electron transport layer: ET-1 (20 nm)
Electron injection layer: ET-2 (3.5 nm)
Cathode: Al (100 nm)

TABLE 2

Device results

| Ex | Dopant | Ratio | CE Cd/A | EQE % | CIE (x, y) | Voltage @ 15 mA/cm$^2$ | T90 (h) | Lum. | Curr. Dens. |
|---|---|---|---|---|---|---|---|---|---|
| 3 | Compound II-1 | 99:1 | 4.4 | 5.1 | (0.143, 0.094) | 4.7 | 122 | 963 | 22.0 |
| 4 | Compound II-1 | 93:7 | 5.1 | 5.3 | (0.144, 0.111) | 4.7 | 122 | 1125 | 22.0 |
| 5 | Compound II-1 | 96.5:3.5 | 4.9 | 5.5 | (0.144, 0.101) | 4.8 | 128 | 1076 | 22.0 |
| 6 | Compound II-2 | 93:7 | 5.4 | 6.2 | (0.140, 0.099) | 4.4 | 151 | 1184 | 22.0 |
| 7 | Compound II-3 | 93:7 | 4.4 | 5.7 | (0.143, 0.084) | 4.3 | 40 | 970 | 22.0 |

Ratio is the weight ratio of host:dopant;
CE is the current efficiency;
EQE = external quantum efficiency;
CIEx and CIEy are the x and y color coordinates according to the C.I.E. chromaticity scale (Commission Internationale de L'Eclairage, 1931).
T90 is the time in hours for a device to reach 90% of the initial luminance at the current density (Curr. Dens.; mA/cm2) given and temperature = 50° C.

Device Examples 8-16

These examples illustrate the device performance of a device having a photoactive layer including the new composition described above. The devices were made according to Device Type 2. Device structure, in order (all percentages are by weight, based on the total weight of the layer):

Glass substrate
Anode: ITO (50 nm)
Short reduction layer: HIJ-1 (100 nm)
Hole injection layer: HIJ-2 (7 nm)
Hole transport layer 1: HTM-2 (90 nm)
Hole transport layer 2: HTM-3 (20 nm)
Photoactive layer: the host, the dopant, and the host/dopant ratio are given below in Table 3 (25 nm)
Electron transport layer: ET-2:ET-3 (1:1 by weight) (26.2 nm)
Electron injection layer: ET-2 (3.5 nm)
Cathode: Al (100 nm)

TABLE 3

Device results

| Ex | Host | Dopant | Ratio | CE Cd/A | EQE % | CIE (x, y) | Voltage @ 15 mA/cm² |
|---|---|---|---|---|---|---|---|
| 8 | H1 | Compound II-12 | 20:1 | 3.9 | 6.4 | 0.149, 0.059 | 5.4 |
| 9 | H1 | Compound II-12 | 32:1 | 3.9 | 6.5 | 0.149, 0.058 | 5.4 |
| 10 | H2 | Compound II-12 | 32:1 | 4.1 | 7.0 | 0.149, 0.056 | 5.7 |
| 11 | H1 | Compound II-13 | 20:1 | 5.5 | 7.0 | 0.141, 0.085 | 5.6 |
| 12 | H1 | Compound II-13 | 13:1 | 5.4 | 6.6 | 0.139, 0.091 | 5.5 |
| 13 | H2 | Compound II-13 | 32:1 | 5.6 | 7.1 | 0.141, 0.085 | 5.6 |
| 14 | H1 | Compound II-16 | 20:1 | 6.7 | 6.1 | 0.137, 0.138 | 5.3 |
| 15 | H1 | Compound II-16 | 32:1 | 6.7 | 6.2 | 0.138, 0.131 | 5.3 |
| 16 | H2 | Compound II-16 | 20:1 | 7.1 | 6.4 | 0.137, 0.135 | 5.5 |

Ratio is the weight ratio of host:dopant;
CE is the current efficiency;
EQE = external quantum efficiency;
CIEx and CIEy are the x and y color coordinates according to the C.I.E. chromaticity scale (Commission Internationale de L'Eclairage, 1931).

Table 3 illustrates the use of Compounds II-12 and II-13, and II-16 as dopants in the emissive layers of organic electronic devices, Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. An electroactive material having Formula I

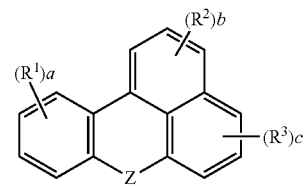

wherein:
Z is selected from the group consisting of C=CR⁴R⁵, PR⁴ᵃ, P(O)R⁴ᵃ, Se,SeO,SeO₂, Te, TeO and TeO₂;
$R^1$, $R^2$, and $R^3$ are each a hydrocarbon aryl having 6-36 ring carbons;
$R^4$-$R^5$ are the same or different at each occurrence and are H, D, aryl, heteroaryl, alkyl, amino, silyl, germyl, deuterated aryl, deuterated heteroaryl, deuterated alkyl, deuterated amino, deuterated silyl, or deuterated germyl;
$R^{4a}$ is selected from the group consisting of alkyl, silyl, germyl, aryl, and deuterated analogs thereof, wherein $R^4$, $R^5$, and $R^{4a}$ do not form a fused ring with $R^1$ to $R^3$;
a=b=c=1.

2. An electroactive material having Formula I

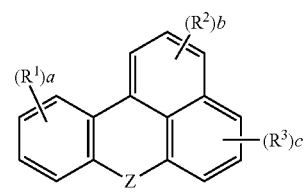

wherein:
Z is selected from the group consisting of C=CR⁴R⁵, PR⁴ᵃ, P(O)R⁴ᵃ, S, SO, SO₂, Se, SeO, SeO₂, Te, TeO, and TeO₂;

$R^2$ and $R^3$ are the same or different at each occurrence and are D, aryl, heteroaryl, alkyl, amino, silyl, germyl, deuterated aryl, deuterated heteroaryl, deuterated alkyl, deuterated amino, deuterated silyl, or deuterated germyl, wherein $R^2$ does not form a fused ring with $R^3$;

$R^4$-$R^5$ are the same or different at each occurrence and are H, D, aryl, heteroaryl, alkyl, amino, silyl, germyl, deuterated aryl, deuterated heteroaryl, deuterated alkyl, deuterated amino, deuterated silyl, or deuterated germyl;

$R^{4a}$ is selected from the group consisting of alkyl, silyl, germyl, aryl, and deuterated analogs thereof;

a=2;

b and c are the same or different and are an integer from 0-3; and $R^1$ groups at positions 1 and 2 are joined to form a 6-membered fused aromatic ring.

3. An electroactive material having Formula I

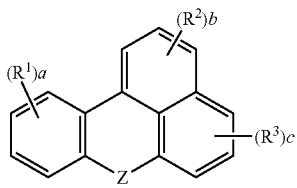

wherein:

Z is selected from the group consisting of $PR^{4a}$, $P(O)R^{4a}$, S, SO, $SO_2$, Se, SeO, $SeO_2$, Te, TeO, and $TeO_2$;

$R^2$ and $R^3$ are the same or different at each occurrence and are D, aryl, heteroaryl, alkyl, amino, silyl, germyl, deuterated aryl, deuterated heteroaryl, deuterated alkyl, deuterated amino, deuterated silyl, or deuterated germyl, wherein $R^2$ does not form a fused ring with $R^3$;

$R^{4a}$ is selected from the group consisting of alkyl, silyl, germyl, aryl, and deuterated analogs thereof;

a=2;

b and c are the same or different and are an integer from 0-3; and $R^1$ groups at positions 2 and 3 are joined to form a 6-membered fused aromatic ring.

4. An electroactive material having Formula I

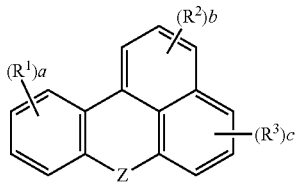

wherein:

Z is selected from the group consisting of SO, $SO_2$, Se, SeO, $SeO_2$, Te, TeO, and $TeO_2$;

$R^1$-$R^3$ are the same or different at each occurrence and are D, aryl, heteroaryl, alkyl, amino, silyl, germyl, deuterated aryl, deuterated heteroaryl, deuterated alkyl, deuterated amino, deuterated silyl, or deuterated germyl, where two groups selected from $R^1$, $R^2$ and $R^3$ can be joined together to form a fused ring;

a=2;

b and c are the same or different and are an integer from 0-3; and $R^1$ groups at positions 3 and 4 are joined to form a 6-membered fused aromatic ring.

5. An electroactive material having Formula I

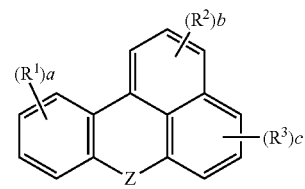

wherein:

Z is selected from the group consisting of $PR^{4a}$, $P(O)R^{4a}$, Se, SeO, $SeO_2$, Te, TeO, and $TeO_2$;

$R^1$-$R^3$ are the same or different at each occurrence and are D, aryl, heteroaryl, alkyl, amino, silyl, germyl, deuterated aryl, deuterated heteroaryl, deuterated alkyl, deuterated amino, deuterated silyl, or deuterated germyl, where two groups selected from $R^1$, $R^2$, and $R^3$ can be joined together to form a fused ring;

$R^{4a}$ is selected from the group consisting of alkyl, silyl, germyl, aryl, and deuterated analogs thereof;

a is an integer from 0-4;

b=2;

c is an integer from 0-3; and $R^2$ groups at positions 5 and 6 are joined to form a 6-membered fused aromatic ring.

6. An electroactive material having Formula I

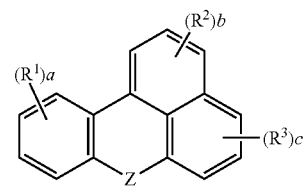

wherein:

Z is selected from the group consisting of $PR^{4a}$, $P(O)R^{4a}$, S, SO, $SO_2$, Se, SeO, $SeO_2$, Te, TeO, and $TeO_2$;

$R^1$-$R^3$ are the same or different at each occurrence and are D, aryl, heteroaryl, alkyl, amino, silyl, germyl, deuterated aryl, deuterated heteroaryl, deuterated alkyl, deuterated amino, deuterated silyl, or deuterated germyl, where two groups selected from $R^1$ and $R^2$ can be joined together to form a fused ring;

$R^{4a}$ is selected from the group consisting of alkyl, silyl, germyl, aryl, and deuterated analogs thereof, wherein $R^{4a}$ does not form a fused ring with $R^1$ to $R^3$;

a is an integer from 0-4;

b is an integer from 0-3;

c=2; and $R^3$ groups at positions 9 and 10 are joined to form a 6-membered fused aromatic ring.

* * * * *